US009962530B2

(12) United States Patent
Johnson et al.

(10) Patent No.: US 9,962,530 B2
(45) Date of Patent: May 8, 2018

(54) INFLATOR FOR DILATION OF ANATOMICAL PASSAGEWAY

(71) Applicant: Acclarent, Inc., Menlo Park, CA (US)

(72) Inventors: Gregory W. Johnson, Milford, OH (US); Emron J. Henry, Cincinnati, OH (US); Jeffrey S. Swayze, Hamilton, OH (US); Cory G. Kimball, Cincinnati, OH (US); Kenneth E. Carper, Cincinnati, OH (US); Daniel L. Geiger, Ft. Thomas, KY (US); Kyle A. Lehr, Cincinnati, OH (US); Matthew B. Newell, Redwood City, CA (US); Luke W. Clauson, Redwood City, CA (US)

(73) Assignee: ACCLARENT, INC., Irvine, CA (US)

( * ) Notice: Subject to any disclaimer, the term of this patent is extended or adjusted under 35 U.S.C. 154(b) by 664 days.

(21) Appl. No.: 14/020,924

(22) Filed: Sep. 9, 2013

(65) Prior Publication Data

US 2014/0074141 A1    Mar. 13, 2014

Related U.S. Application Data

(63) Continuation-in-part of application No. 13/837,577, filed on Mar. 15, 2013.
(Continued)

(51) Int. Cl.
*A61M 29/00* (2006.01)
*A61B 17/24* (2006.01)
*A61M 25/10* (2013.01)

(52) U.S. Cl.
CPC .............. *A61M 29/00* (2013.01); *A61B 17/24* (2013.01); *A61M 25/10182* (2013.11); *A61M 25/10188* (2013.11); *A61M 2025/1022* (2013.01)

(58) Field of Classification Search
CPC .... A61M 2025/1022; A61M 25/10182; A61M 25/1018; A61M 5/31535; A61M 5/31541;
(Continued)

(56) References Cited

U.S. PATENT DOCUMENTS 4,655,749 A    4/1987 Fischione
4,723,938 A *  2/1988 Goodin ............. A61M 25/1018
                                                    604/108
(Continued)

FOREIGN PATENT DOCUMENTS

JP    2008-099917 A    5/2008
WO    WO 92/006735 A1  4/1992
(Continued)

OTHER PUBLICATIONS

Design U.S. Appl. No. 29/466,466, filed Sep. 9, 2013.
(Continued)

*Primary Examiner* — Christopher L Templeton
*Assistant Examiner* — Majid Jamialahmadi
(74) *Attorney, Agent, or Firm* — Frost Brown Todd LLC

(57) ABSTRACT

A dilation catheter system is provided to dilate the ostium of a paranasal sinus or some other anatomical passageway (e.g., within the ear, nose, or throat, etc.). The system may include a dilation catheter, a dilator, a guide catheter, and an inflator. The dilation catheter may be positioned between the dilator and the inflator. The guide catheter is configured to guide the dilator into the affected passageway. The inflator may then be actuated to transfer fluid from the inflator, through the dilation catheter, and into the dilator. The transfer of fluid may inflate the dilator to an expanded state to open or dilate the affected passageway. The inflator may include a body, a plunger assembly, and locking features that selectively secure the position of the plunger assembly (Continued)

relative to the body by moving along a path that is transverse to a longitudinal axis defined by the plunger assembly.

18 Claims, 50 Drawing Sheets

Related U.S. Application Data

(60) Provisional application No. 61/725,523, filed on Nov. 13, 2012, provisional application No. 61/698,788, filed on Sep. 10, 2012.

(58) Field of Classification Search
CPC ............ A61M 5/31551; A61M 5/3155; A61M 5/31555; A61M 5/31501; A61M 2005/31508; A61M 2005/3151; A61M 5/31528; A61M 5/31548; A61M 2005/2073; A61M 25/10181; A61M 25/10184
USPC ....... 604/207–211, 224, 920, 220, 219, 218; 606/191, 920, 219, 97.02, 97.03, 224, 606/220; 152/415
See application file for complete search history.

(56) References Cited

U.S. PATENT DOCUMENTS

| | | | |
|---|---|---|---|
| 4,919,121 A | 4/1990 | Rydell et al. | |
| 5,213,115 A | 5/1993 | Zytkovicz et al. | |
| 5,242,430 A | 9/1993 | Arenas et al. | |
| 5,279,563 A * | 1/1994 | Brucker ............ | A61M 25/1018 604/100.03 |
| 5,324,265 A * | 6/1994 | Murray ............... | A61M 5/3234 604/110 |
| 5,743,889 A * | 4/1998 | Sams ................ | A61M 5/31551 604/207 |
| 6,689,102 B2 | 2/2004 | Greene | |
| 7,207,971 B2 | 4/2007 | Hart et al. | |
| 7,630,676 B2 | 12/2009 | Pirwitz | |
| 7,654,997 B2 | 2/2010 | Makower et al. | |
| 7,803,150 B2 | 9/2010 | Chang et al. | |
| 7,959,607 B2 | 6/2011 | Smith | |
| D746,977 S | 1/2016 | Johnson et al. | |
| 2006/0004323 A1 | 1/2006 | Chang et al. | |
| 2007/0112299 A1* | 5/2007 | Smit ................... | A61M 5/1456 604/67 |
| 2007/0129751 A1 | 6/2007 | Muni et al. | |
| 2007/0208301 A1 | 9/2007 | Evard et al. | |
| 2008/0183128 A1 | 7/2008 | Morriss et al. | |
| 2010/0030031 A1 | 2/2010 | Goldfarb et al. | |
| 2011/0004057 A1 | 1/2011 | Goldfarb et al. | |
| 2012/0078118 A1 | 3/2012 | Jenkins et al. | |

FOREIGN PATENT DOCUMENTS

| | | |
|---|---|---|
| WO | WO 94/015120 A1 | 7/1994 |
| WO | WO 97/044077 A1 | 11/1997 |
| WO | WO 2006/0130491 A2 | 12/2006 |

OTHER PUBLICATIONS

U.S. Appl. No. 13/837,577, filed Mar. 15, 2013.
U.S. Appl. No. 61/698,788, filed Sep. 10, 2012.
U.S. Appl. No. 61/725,523, filed Nov. 13, 2012.
Chinese Office Action, First Office Action, dated Sep. 5, 2016 for Application No. CN 201380058551.7, 5 pgs.
Chinese Search Report, First Search, dated Aug. 24, 2016 for Application No. CN 201380058551.7, 3 pgs.
European Search Report dated Apr. 4, 2016 re Application No. 13 762 706.3.
International Search Report and Written Opinion dated Dec. 2, 2013 re Application No. PCT/US2013/058699, 12 pgs.
International Preliminary Report on Patentability dated Mar. 10, 2015 re Application No. PCT/US2013/058699, 7 pgs.
International Search Report and Written Opinion dated Dec. 2, 2013 re Application No. PCT/US2013/058702, 14 pgs.
International Preliminary Report on Patentability dated Mar. 10, 2015 re Application No. PCT/US2013/058702, 9 pgs.
Japanese Office Action, Notification of Reasons for Refusal, dated Aug. 1, 2017 for Application No. JP 2015-531274, 5 pgs.
U.S. Appl. No. 13/837,577.

* cited by examiner

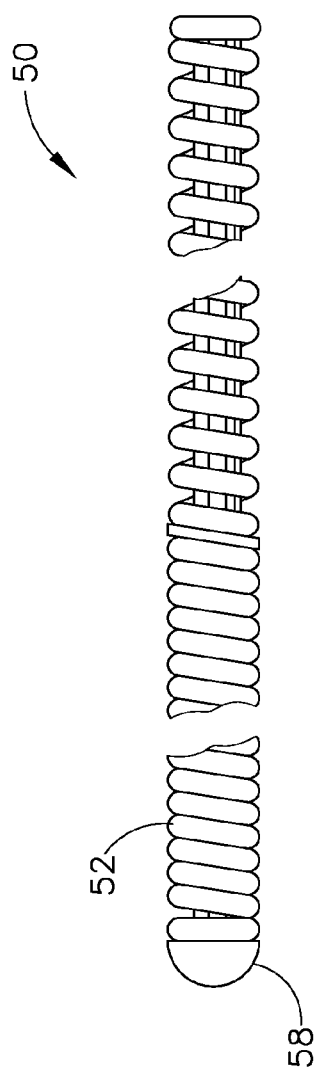
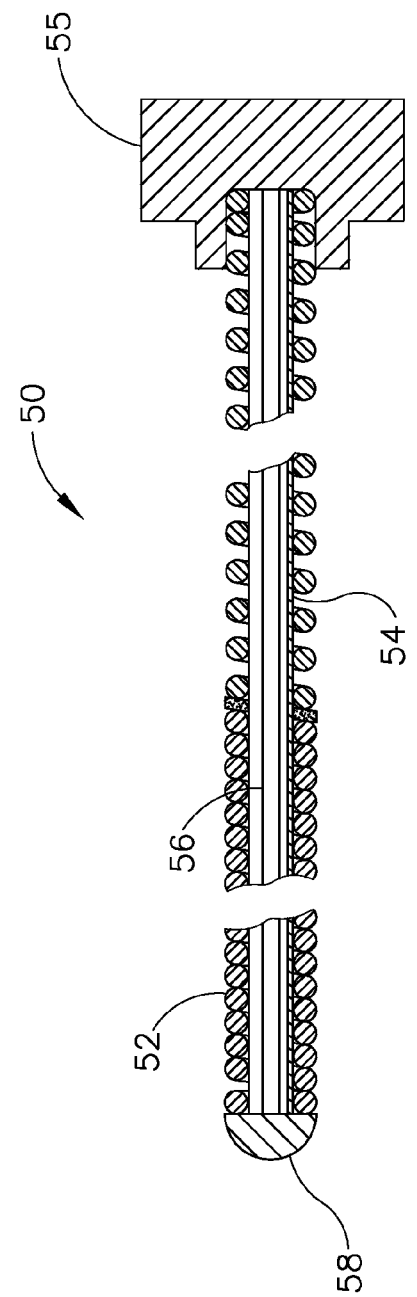

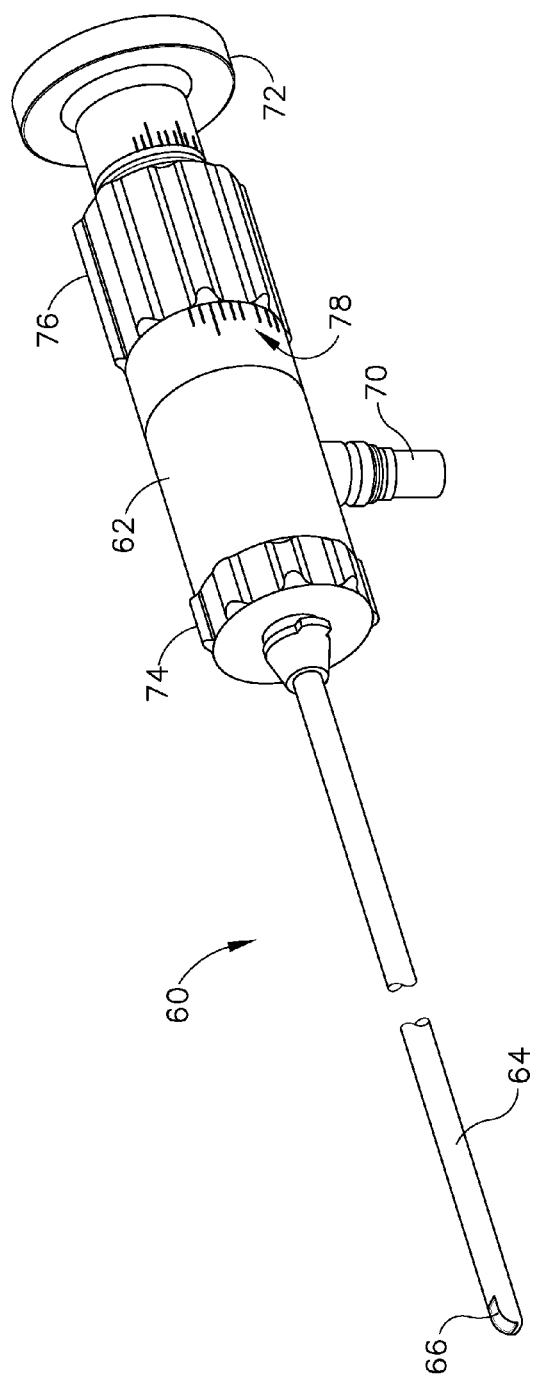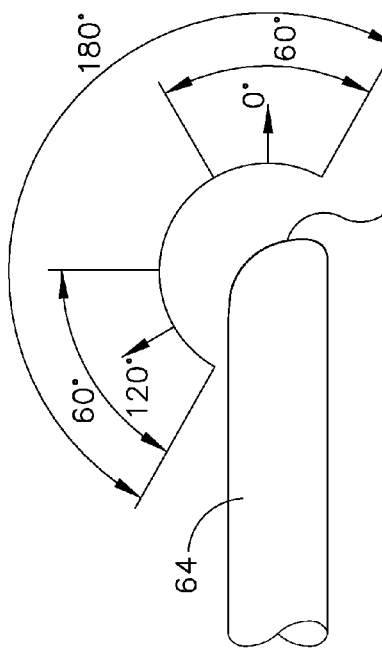

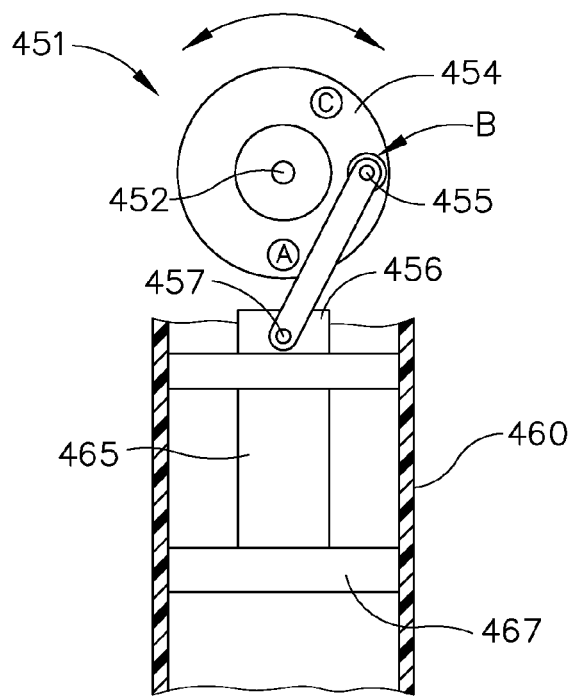
Fig.10
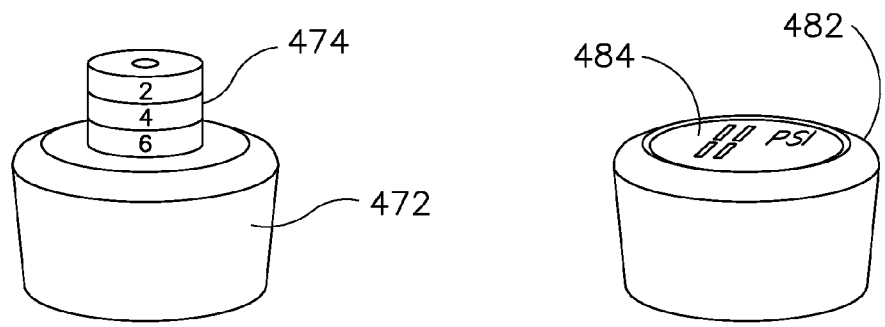
Fig.11
Fig.12

INFLATOR FOR DILATION OF ANATOMICAL PASSAGEWAY

PRIORITY

This application is a continuation-in-part of U.S. patent application Ser. No. 13/837,577, entitled "Inflator for Dilation of Anatomical Passageway," filed Mar. 15, 2013, the disclosure of which is incorporated by reference herein.

U.S. patent application Ser. No. 13/837,577 claims priority to U.S. Provisional Pat. App. No. 61/725,523, entitled "Inflator for Dilation of Anatomical Passageway," filed Nov. 13, 2012, the disclosure of which is incorporated by reference herein.

U.S. patent application Ser. No. 13/837,577 also claims priority to U.S. Provisional Pat. App. No. 61/698,788, entitled "Inflator for Dilation of Anatomical Passageway," filed Sep. 10, 2012, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

FIG. 4 depicts a perspective view of an exemplary endoscope suitable for use with the dilation catheter system of FIG. 1;

FIG. 5 depicts a side elevational view of the distal end of the endoscope of FIG. 5, showing an exemplary range of viewing angles;

FIG. 10 depicts a side view of the crank shaft assembly from the inflator of FIG. 9;

FIG. 11 depicts a perspective view of an exemplary pressure gauge;

FIG. 12 depicts a perspective view of another exemplary pressure gauge;

Figure 1:
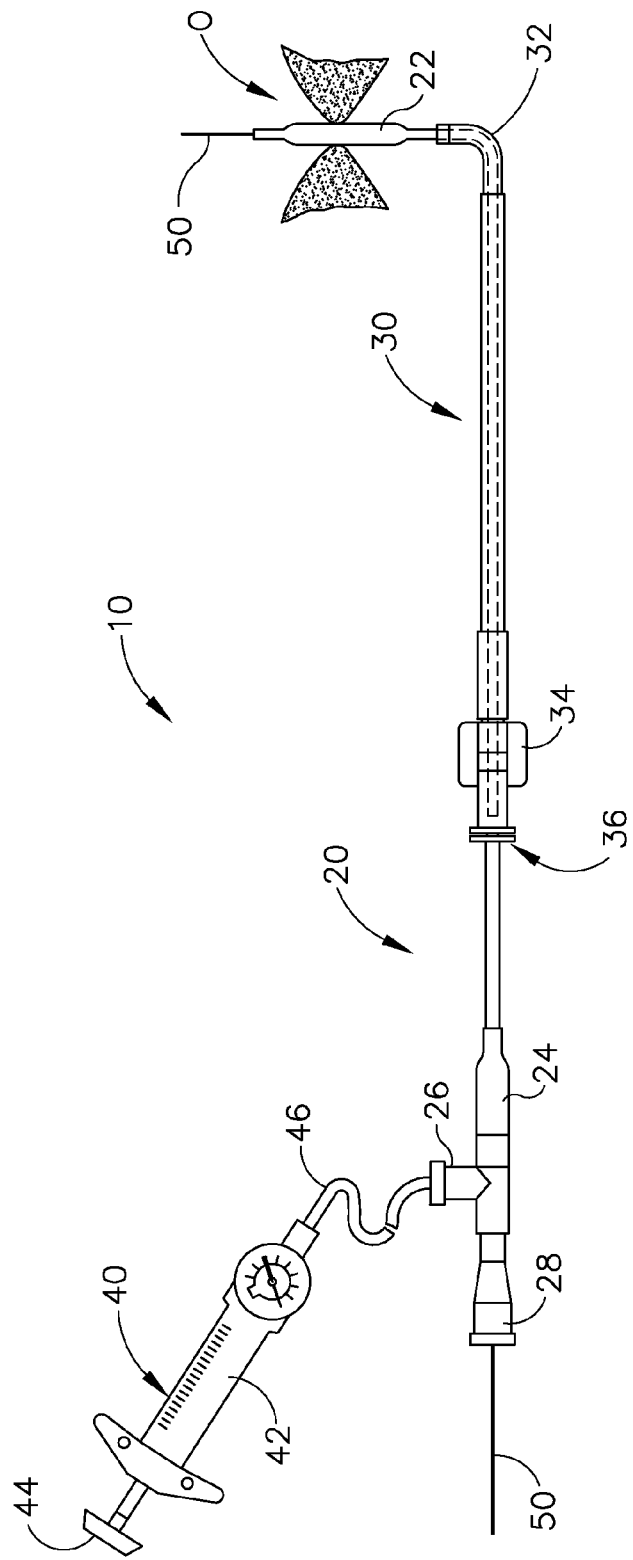
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. OVERVIEW OF EXEMPLARY DILATION CATHETER SYSTEM

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26).

As best seen in FIGS. 2-3, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination fiber (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the sinus and paranasal cavity after dilation catheter (20) has been used to dilate an ostium (O). Such irrigation may be performed to flush out blood, etc. that may be present after the dilation procedure. By way of example only, such irrigation may be carried out in accordance with at least some of the teachings of U.S. Pub. No. 2008/0138128, entitled "Methods, Devices and Systems for Treatment and/or Diagnosis of Disorders of the Ear, Nose and Throat," published Jul. 31, 2008, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

II. OVERVIEW OF EXEMPLARY ENDOSCOPE

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein

III. EXEMPLARY ALTERNATIVE INFLATORS

Inflator (40) shown in FIG. 1 and described above is just one example of an inflator that may be incorporated into dilator catheter system (10). Additional merely illustrative examples of alternative forms that inflator (40) may take will be described in greater detail below. It should be understood that these exemplary alternative inflators may be readily coupled with flexible tube (46) in place of inflator (40) described above, for use in dilator catheter system (10). In some versions, the exemplary alternative inflators described below may be directly coupled with lateral port (26), such that flexible tube (46) is simply omitted. Other suitable configurations and arrangements will be apparent to those of ordinary skill in the art in view of the teachings herein.

A. Exemplary Alternative Inflator with Knob and Pushbutton Thread Release

Figure 6:
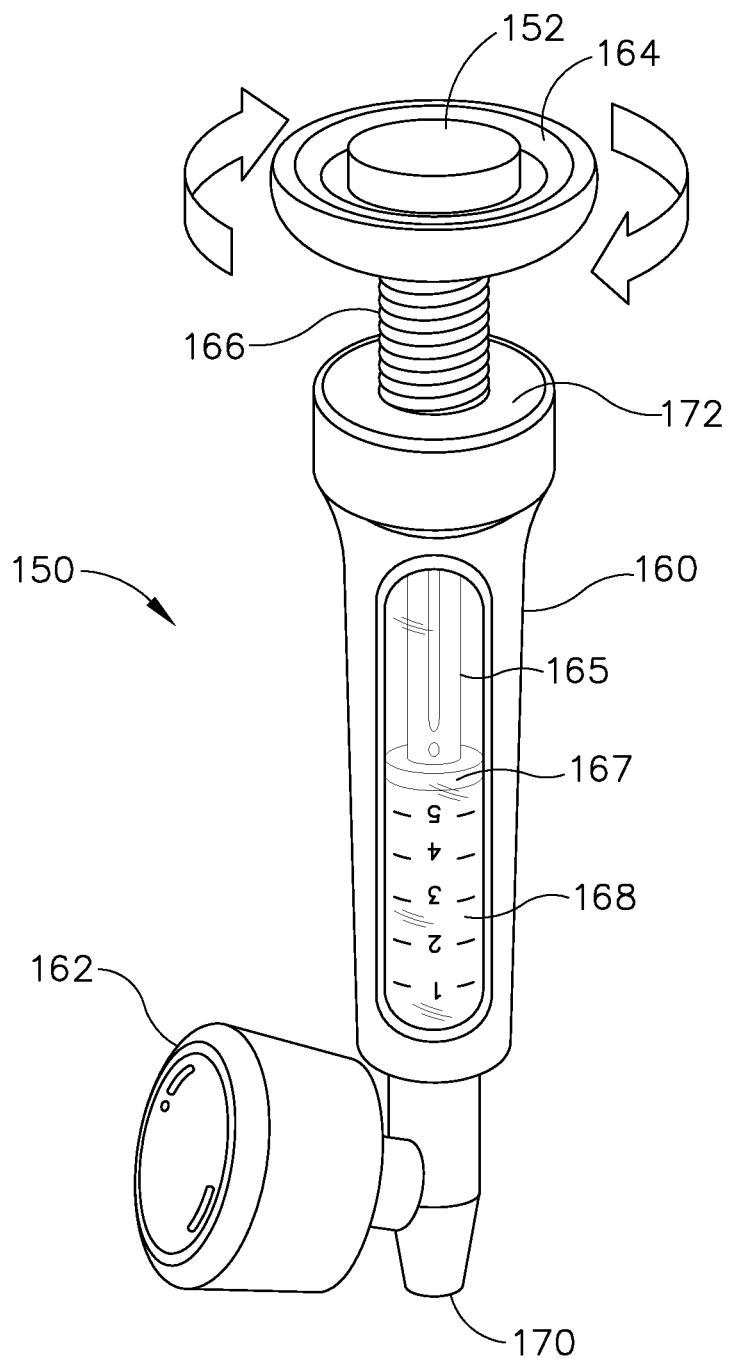
FIG. 6 depicts a perspective view of an exemplary inflator suited for use with the dilator catheter system of FIG. 1.

FIG. 6 shows an exemplary inflator (150) that comprises a body (160), an actuator knob (164), and a pressure gauge (162). Body (160) of the present example is formed as a substantially hollow cylinder, similar to syringe barrel (42) described above, although other suitable configurations may be used. Body (160) comprises a reservoir (168), a distal port (170), and a proximal cap (172). A rod (165) extends into body (160). Plunger (167) is coupled to a distal end of rod (165) and extends outwardly to the inner diameter of body (160) to form a substantially fluid tight seal with body (160). The volume between plunger (167) and the distal end of body (160) forms reservoir (168). Reservoir (168) may be configured to hold about 3 to about 5 cc of fluid (e.g., saline). Rod (165) and plunger (167) may translate proximally and distally to adjust the size of reservoir (168). When rod (165) and plunger (167) translate proximally, the volume of reservoir (168) increases. When rod (165) and plunger (167) translate distally, the volume of reservoir (168) decreases. Port (170) at the distal end of body (160) is in fluid communication with reservoir (168) such that fluid may flow into and out of reservoir (168) via port (170). Port (170) may be coupled with flexible tube (46) of dilator catheter system (10).

Actuator knob (164) is coupled to body (160) via a threaded shaft (166), which is in selective threaded engagement with proximal cap (172) of body (160). Threaded shaft (166) is configured to rotate unitarily with actuator knob (164). Thus, rotation of actuator knob (164) relative to body (160) will cause threaded shaft (166) to translate relative to body (160) when the threading of threaded shaft (166) is engaged with proximal cap (172). Threaded shaft (166) is further coupled with rod (165) such that when actuator knob (164) is rotated relative to body (160), rod (165) and plunger (167) translate proximally or distally relative to body (165) based on the direction in which actuator knob (164) and threaded shaft (166) are rotated. In some versions, threaded shaft (166) and rod (165) are the same structure, such that threaded shaft (166) extends all the way to plunger (167). In some such versions, threaded shaft (166) rotates freely relative to plunger (167).

In the present example, push button (152) is operable to disengage the threading of threaded shaft (166) relative to proximal cap (172), to thereby permit threaded shaft (166) to translate freely relative to body (160) when push button (152) is in a depressed position. Various suitable features that may be used to provide such operability will be apparent to those of ordinary skill in the art in view of the teachings herein. By way of example only, the threading of threaded shaft (166) may be selectively retractable inwardly relative to the longitudinal axis of threaded shaft (166). A translating cam component (not shown) that is coupled with push button (152) may be operable to extend and/or retract the threading of threaded shaft (166) based on the position of push button (152). For instance, when push button (152) is not being depressed, the cam component may be biased to a position where it urges the threading outwardly and holds the threading in the outward position, into engagement with threaded cap (172). The threading may itself be resiliently biased to retract inwardly, such that when push button (152) is depressed, the cam component disengages the threading and the threading retracts inwardly to disengage body (160). It should also be understood that push button (152) may be resiliently biased toward the non-depressed position. Still other suitable components and configurations that may be used to provide the above-described selective engagement between threaded shaft (166) and proximal cap (172) will be apparent to those of ordinary skill in the art in view of the teachings herein.

Gauge (162) of the present example is positioned distal of reservoir (168) to measure the pressure within dilator catheter system (10). Gauge (162) may include a pivoting pin that indicates fluid pressure based on the angular position of the pin. Alternatively, gauge (162) may provide any other suitable type of indication of fluid pressure, including but not limited to the other types of fluid pressure indication described below. In the present example, gauge (162) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (162) may thus provide the operator with real time feedback indicating the fluid pressure within dilator (22) to enable the operator to determine whether the desired pressure level has been achieved.

In an exemplary use of inflator (150), a operator may start with plunger (167) advanced to a distal position in body (160). The operator may then position port (170) in a bowl or other container of saline to draw fluid from. In instances where port (170) is coupled with one end of flexible tube (46), the operator may position the other end of flexible tube (46) in the saline. In either case, the operator may then retract plunger (167) relative to body (160) to draw the saline (or other fluid) into reservoir (168). In some instances, the operator depresses button (152) to disengage threading of threaded shaft (166) from proximal cap (172), thereby permitting the operator to freely pull plunger (167) proximally without having to rotate actuator knob (164). The operator may nevertheless grasp actuator knob (164) in order to translate plunger (167) proximally. The operator may observe the position of plunger (167) relative to indicia on body (160) and may initially draw in more fluid than the operator expects to need in order to sufficiently inflate dilator (22). The operator may then remove port (170) or flexible tube (46) from the saline container and advance plunger (167) distally in order to purge air from reservoir (168). For instance, the operator may orient inflator (150) such that port (170) is positioned upwardly to gather air at the top of reservoir (168) before advancing plunger (167) distally in order to purge air from reservoir (168).

Once reservoir (168) has been sufficiently filled with fluid and air has been purged, the operator may couple inflator (150) with dilation catheter (20), such as by coupling port (170) with lateral port (26) via a flexible tube (46). With dilator (22) being suitably positioned within an anatomical passageway (e.g., an ostium (O), etc.), the operator may then advance plunger (167) distally in order to transfer fluid from reservoir (168) to dilator (22). In some instances, this act may begin with free translation of threaded shaft (166) relative to proximal cap (172), with the operator depressing push button (152) to disengage the threading, and with the operator gripping actuator knob (164) to translate threaded shaft (166) and plunger (167) distally. At some point, however, the operator may release push button (152) to engage the threading of threaded shaft (166) with proximal cap (172), and may finish the final stages of distal translation of plunger (167) by rotating actuator knob (164). This may enable the operator to more precisely "dial in" the appropriate amount of pressure in dilator (22), observing the pressure reading at gauge (162) while rotating actuator knob (164).

In some instances, the operator simply relies on tactile feedback in the form of physical resistance to pushing of actuator knob (164) in order to determine the appropriate time to transition from pushing of actuator knob (164) (with push button (152) depressed) to rotating of actuator knob (164) (with push button (152) released). In addition or in the alternative, the operator may determine the appropriate time to transition from pushing of actuator knob (164) to rotating of actuator knob (164) based on the position of plunger (167) relative to one or more markings on body (160). Other suitable forms of feedback that may be used to determine an appropriate transition time from pushing of actuator knob (164) to rotating of actuator knob (164) will be apparent to those of ordinary skill in the art in view of the teachings herein.

Once the operator has attained the desired level of pressure in dilator (22) within the anatomical passageway to dilate the anatomical passageway, the operator may pause for an approximate, predetermined period of time (e.g., approximately three seconds, etc.). The operator may then once again depress push button (152) and pull knob (164) proximally relative to body (160), to thereby retract plunger (167) for withdrawal of fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (168) may be used repeatedly to dilate a plurality of anatomical passageways, without having to withdraw dilator (22) from the patient, and without having to decouple inflator (150) from the rest of dilator catheter system (10), until all of the desired dilations have been completed.

In the foregoing example, the threading of threaded shaft (166) is engaged with proximal cap (172) when push button (152) is not being depressed. In some other versions, the threading of threaded shaft (166) is engaged with proximal cap (172) only when push button (152) is being depressed. Other suitable variations of inflator (150) will be apparent to those of ordinary skill in the art in view of the teachings herein. Similarly, other suitable ways in which inflator (150) may be used will be apparent to those of ordinary skill in the art in view of the teachings herein.

B. Exemplary Alternative Inflator with Knob and Rotary Thread Release

Figure 7:
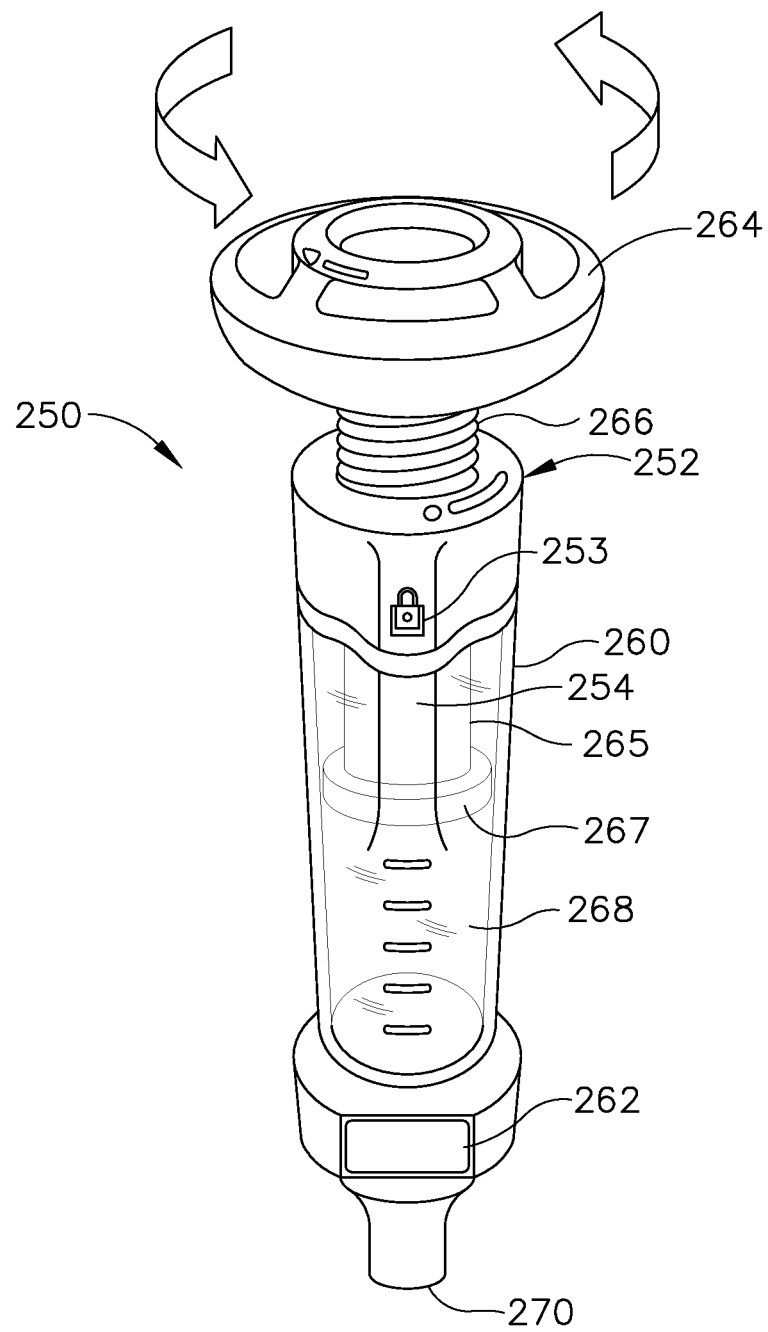
FIG. 7 depicts a perspective view of another exemplary inflator suited for use with the dilator catheter system of FIG. 1.

FIG. 7 shows another exemplary inflator (250). Inflator (250) of this example is substantially similar to inflator (150) described above with reference to FIG. 6. In particular, inflator (250) comprises a body (260), an actuator knob (264), and a pressure gauge (262). Body (260) of the present example is formed as a substantially hollow cylinder, similar to syringe barrel (42) described above, although other suitable configurations may be used. Body (260) comprises a reservoir (268), a distal port (270), and a rotary locking feature (252) at the proximal end of body (260). A rod (265) extends into body (260). Plunger (267) is coupled to a distal end of rod (265) and extends outwardly to the inner diameter of body (260) to form a substantially fluid tight seal with body (260). The volume between plunger (267) and the distal end of body (260) forms reservoir (268). Reservoir (268) may be configured to hold about 3 to about 5 cc of fluid (e.g., saline). Rod (265) and plunger (267) may translate proximally and distally to adjust the size of reservoir (268). When rod (265) and plunger (267) translate proximally, the volume of reservoir (268) increases. When rod (265) and plunger (267) translate distally, the volume of reservoir (268) decreases. Port (270) at the distal end of body (260) is in fluid communication with reservoir (268) such that fluid may flow into and out of reservoir (268) via port (270). Port (270) may be coupled with flexible tube (46) of dilator catheter system (10).

Actuator knob (264) is coupled to body (260) via a threaded shaft (266), which is in selective threaded engagement with rotary locking feature (252) of body (260). Threaded shaft (266) is configured to rotate unitarily with actuator knob (264). Thus, rotation of actuator knob (264) relative to body (260) will cause threaded shaft (266) to translate relative to body (260) when the threading of threaded shaft (266) is engaged with rotary locking feature (252). Threaded shaft (266) is further coupled with rod (265) such that when actuator knob (264) is rotated relative to body (260), rod (265) and plunger (267) translate proximally or distally relative to body (265) based on the direction in which actuator knob (264) and threaded shaft (266) are rotated. In some versions, threaded shaft (266) and rod (265) are the same structure, such that threaded shaft (266) extends all the way to plunger (267). In some such versions, threaded shaft (266) rotates freely relative to plunger (267).

In the present example, rotary locking feature (252) comprises an annular component that is rotatable relative to body (260) to selectively engage/disengage the threading of threaded shaft (266). In particular, rotary locking feature (252) is operable to selectively disengage the threading of threaded shaft (266), to thereby permit threaded shaft (266) to translate freely relative to body (260) when rotary locking feature (252) is rotated to an unlocked position. Various suitable features that may be used to provide such operability will be apparent to those of ordinary skill in the art in view of the teachings herein. By way of example only, rotary locking feature (252) may include retractable internal threading that is selectively engaged with the external threading of threaded shaft (266) based on the rotational position of rotary locking feature (252) relative to body (260). As another merely illustrative example, an internally threaded member may be positioned within rotary locking feature (252), and rotary locking feature (252) may be configured to selectively secure the rotational position of this internally threaded member relative to body (260) based on the rotational position of rotary locking feature (252) relative to body (260). For instance, the internally threaded member may be rotationally fixed relative to body (260) when rotary locking feature (252) is rotated to a locked position; while the internally threaded member may rotate freely relative to body (260) when rotary locking feature (252) is rotated to an unlocked position. Still other suitable components and configurations that may be used to provide the above-described selective engagement between threaded shaft (266) and body (260) will be apparent to those of ordinary skill in the art in view of the teachings herein.

In addition, body (260) and rotary locking feature (252) of the present example include complementary features to provide feedback to the operator indicating whether rotary locking feature (252) is in the locked or unlocked position. In particular, rotary locking feature (252) includes a graphical representation (253) of a padlock that aligns with a complementary indicator on body (260) when rotary locking feature (252) is in the locked position. In addition, body (260) and rotary locking feature (252) have the same asymmetric cross-sectional shape. When rotary locking feature (252) is rotated to the locked position, these cross-sections align such that the outer surfaces of body and rotary locking feature (252) are substantially flush with each other. When rotary locking feature (252) is rotated to the unlocked position, the cross-sections are not aligned and their non-alignment is visually pronounced by the asymmetry of their cross-sections. In other words, the non-alignment of the cross-sections is easy to observe visually and tactilely. Other suitable ways in which the locked/unlocked state of rotary locking feature (252) may be indicated will be apparent to those of ordinary skill in the art in view of the teachings herein.

Gauge (262) of the present example is positioned distal of reservoir (268) to measure the pressure within dilator catheter system (10). Gauge (262) of this example comprises a digital pressure gauge with an LCD or LED screen providing the numerical value of the fluid pressure. Alternatively, gauge (262) may provide any other suitable type of indication of fluid pressure, including but not limited to the other types of fluid pressure indication described herein. In the present example, gauge (262) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (262) may thus provide the operator with real time feedback indicating the fluid pressure within dilator (22) to enable the operator to determine whether the desired pressure level has been achieved.

In an exemplary use of inflator (250), a operator may start with plunger (267) advanced to a distal position in body (260). The operator may then position port (270) in a bowl or other container of saline to draw fluid from. In instances where port (270) is coupled with one end of flexible tube (46), the operator may position the other end of flexible tube (46) in the saline. In either case, the operator may then retract plunger (267) relative to body (260) to draw the saline (or other fluid) into reservoir (268). In some instances, rotary locking feature (252) is rotated to the unlocked position at this stage, to disengage threading of threaded shaft (266) relative to body (260), thereby permitting the operator to freely pull plunger (267) proximally without having to rotate actuator knob (264). The operator may nevertheless grasp actuator knob (264) in order to translate plunger (267) proximally. The operator may observe the position of plunger (267) relative to indicia on body (260) and may initially draw in more fluid than the operator expects to need in order to sufficiently inflate dilator (22). The operator may then remove port (270) or flexible tube (46) from the saline container and advance plunger (267) distally in order to purge air from reservoir (268). For instance, the operator may orient inflator (250) such that port (270) is positioned upwardly to gather air at the top of reservoir (268) before advancing plunger (267) distally in order to purge air from reservoir (268).

Once reservoir (268) has been sufficiently filled with fluid and air has been purged, the operator may couple inflator (250) with dilation catheter (20), such as by coupling port (270) with lateral port (26) via a flexible tube (46). With dilator (22) being suitably positioned within an anatomical passageway (e.g., an ostium (O), etc.), the operator may then advance plunger (267) distally in order to transfer fluid from reservoir (268) to dilator (22). In some instances, this act may begin with free translation of threaded shaft (266) relative to body (260), with rotary locking feature (252) being rotated to the unlocked position to disengage the threading, and with the operator gripping actuator knob (264) to translate threaded shaft (266) and plunger (267) distally. At some point, however, the operator may rotate rotary locking feature (252) to the locked position, to engage the threading of threaded shaft (266) with body (260), and may finish the final stages of distal translation of plunger (267) by rotating actuator knob (264). This may enable the operator to more precisely "dial in" the appropriate amount of pressure in dilator (22), observing the pressure reading at gauge (262) while rotating actuator knob (264).

In some instances, the operator simply relies on tactile feedback in the form of physical resistance to pushing of actuator knob (264) in order to determine the appropriate time to transition from pushing of actuator knob (264) (with rotary locking feature (252) in the unlocked position) to rotating of actuator knob (264) (with rotary locking feature (252) in the locked position). In addition or in the alternative, the operator may determine the appropriate time to transition from pushing of actuator knob (264) to rotating of actuator knob (264) based on the position of plunger (267) relative to one or more markings on body (260). Other suitable forms of feedback that may be used to determine an appropriate transition time from pushing of actuator knob (264) to rotating of actuator knob (264) will be apparent to those of ordinary skill in the art in view of the teachings herein.

Once the operator has attained the desired level of pressure in dilator (22) within the anatomical passageway to dilate the anatomical passageway, the operator may pause for an approximate, predetermined period of time (e.g., approximately three seconds, etc.). The operator may then once again rotate rotary locking feature (252) back to the unlocked position and pull knob (264) proximally relative to body (260), to thereby retract plunger (267) for withdrawal of fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (268) may be used repeatedly to dilate a plurality of anatomical passageways, without having to withdraw dilator (22) from the patient, and without having to decouple inflator (250) from the rest of dilator catheter system (10), until all of the desired dilations have been completed.

Other suitable variations of inflator (250) will be apparent to those of ordinary skill in the art in view of the teachings herein. Similarly, other suitable ways in which inflator (250) may be used will be apparent to those of ordinary skill in the art in view of the teachings herein.

C. Exemplary Alternative Inflator with Resiliently Biased Plunger

Figure 8:
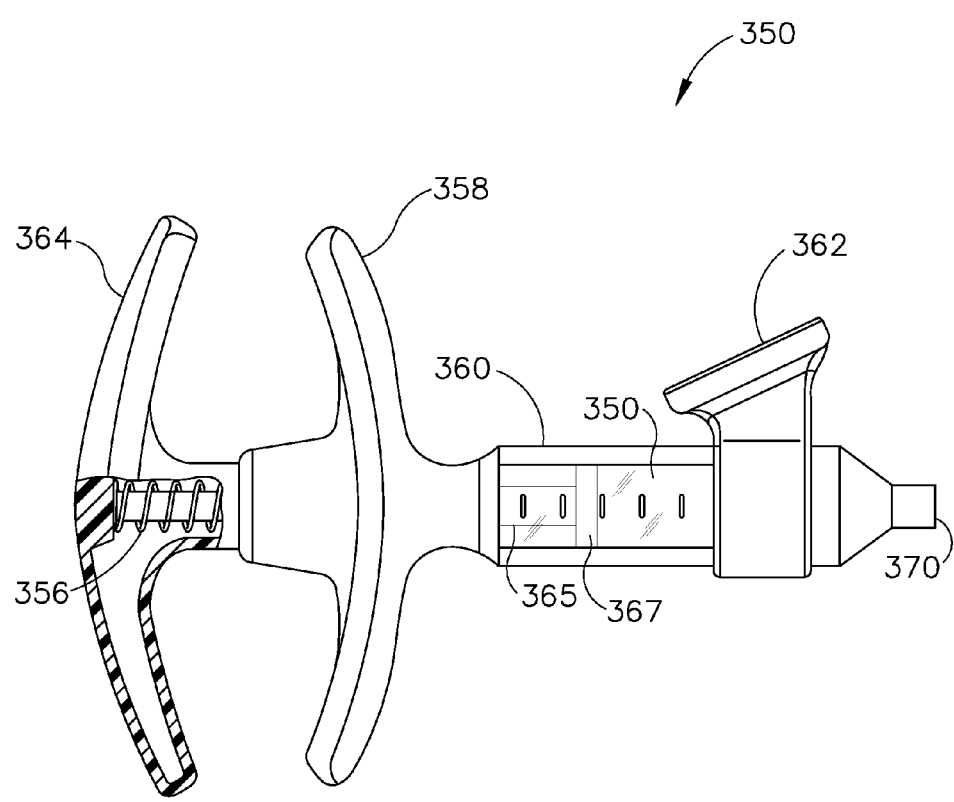
FIG. 8 depicts a side view of another exemplary inflator, with a portion removed, suited for use with the dilator catheter system of FIG. 1.

FIG. 8 shows another exemplary inflator (350). Inflator (350) of this example is configured for one-handed operation. Inflator (350) of this example comprises a body (360), an actuator (364), and a pressure gauge (362). Body (360) of the present example is formed as a substantially hollow cylinder, similar to syringe barrel (42) described above, although other suitable configurations may be used. Body (360) comprises a reservoir (368), a distal port (370), and a handle (358) at the proximal end of body (360). A rod (365) extends into body (360). Plunger (367) is coupled to a distal end of rod (365) and extends outwardly to the inner diameter of body (360) to form a substantially fluid tight seal with body (360). The volume between plunger (367) and the distal end of body (360) forms reservoir (368). Reservoir (368) may be configured to hold about 3 to about 5 cc of fluid (e.g., saline). Rod (365) and plunger (367) may translate proximally and distally to adjust the size of reservoir (368). When rod (365) and plunger (367) translate proximally, the volume of reservoir (368) increases. When rod (365) and plunger (367) translate distally, the volume of reservoir (368) decreases. Port (370) at the distal end of body (360) is in fluid communication with reservoir (368) such that fluid may flow into and out of reservoir (368) via port (370). Port (370) may be coupled with flexible tube (46) of dilator catheter system (10).

Actuator (364) is unitarily secured to rod (365), such that actuator (364) and rod (365) (and, hence, plunger (367)) translate unitarily relative to body (360). A coil spring (356) is coaxially disposed about rod (365) and bears against both actuator (364) and body (360). Coil spring (356) thus resiliently biases actuator (364) proximally. Of course, any other suitable type of resilient member may be used. Actuator (364) has a "T" shape that is configured to rest in the palm of the operator's hand. Handle (358) of body (360) is configured such that a operator may wrap his or her fingers around handle (358) with actuator (364) in the palm of the same hand. The operator may thus drive actuator (364) distally relative to handle (358) by squeezing with that single hand. As the operator thereafter releases their grip, the resilient bias of coil spring (356) returns actuator (364) proximally relative to handle (358). Plunger (367) translates relative to body (360) accordingly.

Gauge (362) of the present example is positioned distal of reservoir (368) to measure the pressure within dilator catheter system (10). Gauge (362) of this example comprises a digital pressure gauge with an LCD or LED screen providing the numerical value of the fluid pressure. Alternatively, gauge (362) may provide any other suitable type of indication of fluid pressure, including but not limited to the other types of fluid pressure indication described herein. In the present example, gauge (362) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (362) may thus provide the operator with real time feedback indicating the fluid pressure within dilator (22) to enable the operator to determine whether the desired pressure level has been achieved.

In an exemplary use of inflator (350), a operator may start with plunger (367) advanced to a distal position in body (360). This may be accomplished by squeezing actuator (364) toward handle (358) with a single hand. The operator may then position port (370) in a bowl or other container of saline to draw fluid from. In instances where port (370) is coupled with one end of flexible tube (46), the operator may position the other end of flexible tube (46) in the saline. In either case, the operator may then release actuator (364) relative to handle (358). The resilient bias of coil spring (356) may cause actuator (364) and rod (365) to retract relative to body (360), which may in turn retract plunger (367) relative to body (360) to draw the saline (or other fluid) into reservoir (368). The operator may then remove port (370) or flexible tube (46) from the saline container and advance plunger (367) distally in order to purge air from reservoir (368). For instance, the operator may orient inflator (350) such that port (370) is positioned upwardly to gather air at the top of reservoir (368) before advancing plunger (367) distally in order to purge air from reservoir (368).

Once reservoir (368) has been sufficiently filled with fluid and air has been purged, the operator may couple inflator (350) with dilation catheter (20), such as by coupling port (370) with lateral port (26) via a flexible tube (46). With dilator (22) being suitably positioned within an anatomical passageway (e.g., an ostium (O), etc.), the operator may then advance actuator (364) distally by squeezing actuator (364) and handle (358) with a single hand, in order to transfer fluid from reservoir (368) to dilator (22). The operator may observe the pressure reading at gauge (362) while advancing actuator (364) distally in order to determine when the appropriate fluid pressure level has been reached.

Once the operator has attained the desired level of pressure in dilator (22) within the anatomical passageway to dilate the anatomical passageway, the operator may pause for an approximate, predetermined period of time (e.g., approximately three seconds, etc.). The operator may then release their grip on actuator (364) to allow coil spring (356) to translate actuator (364) and rod (365) proximally, to thereby retract plunger (267) for withdrawal of fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (368) may be used repeatedly to dilate a plurality of anatomical passageways, without having to withdraw dilator (22) from the patient, and without having to decouple inflator (350) from the rest of dilator catheter system (10), until all of the desired dilations have been completed.

In some instances, rod (365) and body (360) include complementary detent features (and/or some other type of feature(s)) that provide the operator with audible and/or tactile feedback. For instance, such features may provide the operator with feedback to indicate longitudinal positions of plunger (367) that are predeterminedly associated with an appropriate pressure level in dilator (22). In addition or in the alternative, such features may provide the operator with feedback to indicate that the longitudinal position of plunger (367) is getting close to a position that is predeterminedly associated with an appropriate pressure level in dilator (22), thereby alerting the operator to slow their distal advancement of actuator (364) and carefully watch gauge (362). Detent features (and/or some other type of feature(s)) may also provide the operator with audible and/or tactile feedback to indicate when plunger (367) has reached a position that is predeterminedly associated with air being purged from reservoir (368) before port (370) is coupled with lateral port (26). As yet another merely illustrative variation, some versions may provide a manual locking feature that enables the operator to selectively secure the position of actuator (364) relative to body—either at one or more predetermined positions and/or at positions selected ad hoc by the operator. Other suitable variations of inflator (350) will be apparent to those of ordinary skill in the art in view of the teachings herein. Similarly, other suitable ways in which inflator (350) may be used will be apparent to those of ordinary skill in the art in view of the teachings herein.

D. Exemplary Alternative Inflator with Lever Actuated Crankshaft Assembly

Figure 9:
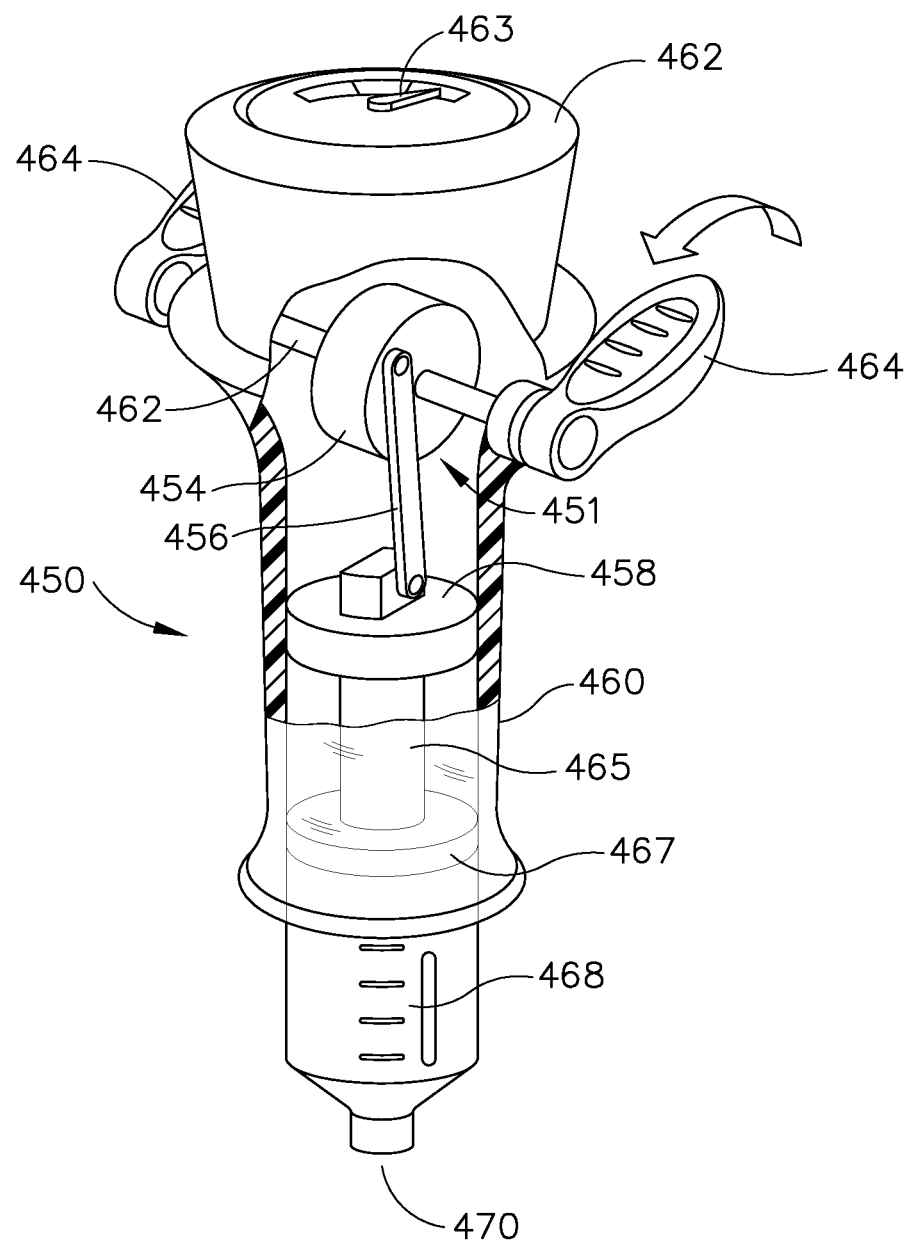
FIG. 9 depicts a perspective view of another exemplary inflator suited for use with the dilator catheter system of FIG. 1.

FIG. 9 shows another exemplary inflator (450). Inflator (450) of this example comprises a body (460), a pair of actuator levers (464), and a pressure gauge (462). Body (460) of the present example is formed as a substantially hollow cylinder, similar to syringe barrel (42) described above, although other suitable configurations may be used. Body (460) comprises a reservoir (468), a distal port (470), and a crank shaft assembly (451) at the proximal end of body (460). A rod (465) is longitudinally driven by crank shaft assembly (451) as described in greater detail below. Plunger (467) is coupled to a distal end of rod (465) and extends outwardly to the inner diameter of body (460) to form a substantially fluid tight seal with body (460). The volume between plunger (467) and the distal end of body (460) forms reservoir (468). Reservoir (468) may be configured to hold about 3 to about 5 cc of fluid (e.g., saline). Rod (465) and plunger (467) may translate proximally and distally to adjust the size of reservoir (468). When rod (465) and plunger (467) translate proximally, the volume of reservoir (468) increases. When rod (465) and plunger (467) translate distally, the volume of reservoir (468) decreases. Port (470) at the distal end of body (460) is in fluid communication with reservoir (468) such that fluid may flow into and out of reservoir (468) via port (470). Port (470) may be coupled with flexible tube (46) of dilator catheter system (10).

Crank shaft assembly (451) comprises a crank shaft (452) and a crank wheel (454). Crank shaft (452) and crank wheel (454) are coaxial with each other and rotate unitarily with each other. Actuator levers (464) are secured to opposing ends of crank shaft (452). Actuator levers (464) are operable to rotate crank shaft (452) and crank wheel (454) relative to body (460), about the axis shared by crank shaft (452) and crank wheel (454). As best seen in FIG. 10, crank wheel (454) includes an integral crank pin (455) that extends along an axis that is offset from the axis shared by crank shaft (452) and crank wheel (454). In other words, crank pin (455) is off center relative to crank wheel (454). One end of a connecting rod (456) is pivotally coupled with crank pin (455), while the other end of connecting rod (456) is pivotally coupled with a pin (457) at the head (458) of rod (465). These couplings may include bushings, bearings, and/or other features to provide smooth pivoting movement of connecting rod (456) relative to crank wheel (454) and head (458). It should be understood that the configuration of crank shaft assembly (451) will provide reciprocation of rod (465) and plunger (467) in response to rotation of actuator levers (464) relative to body (460). It should also be understood that positioning of actuator levers (464) on both sides of body (460) may facilitate use by both left-handed and right-handed operators.

In the present example, actuator levers (464), crank shaft (452), and crank wheel (454) are operable to rotate through a range of approximately 150°. Alternatively, any other suitable angular range may be provided. In instances providing a limited angular range, the limits may be imposed by bosses or other features that provide hard stops preventing rotation of actuator levers (464), crank shaft (452), and crank wheel (454) beyond the predetermined range. As shown in FIG. 10, there are three predetermined angular positions within the range—position "A," position "B," and position "C." These angular positions are associated with the location of crank pin (455) at particular stages of use of inflator (450) as will be described in greater detail below. It should be understood that inflator (450) may include detent features (and/or some other type of feature(s)) that provide the operator with audible and/or tactile feedback to indicate arrival at position "A," position "B," and/or position "C." In some other versions, a detent feature is only used to indicate arrival at position "B," while hard stops indicate arrival at position "A" and position "B." Other suitable forms of feedback will be apparent to those of ordinary skill in the art in view of the teachings herein.

Gauge (462) of the present example is positioned at the proximal end of body (460), and includes a pivoting pin (463) that indicates fluid pressure based on the angular position of the pin. Alternatively, gauge (462) may provide any other suitable type of indication of fluid pressure. By way of example only, gauge (462) may be substituted with the gauge (472) shown in FIG. 11, which includes a longitudinally sliding pressure indicator (474) similar to a conventional tire pressure gauge. As another merely illustrative alternative, gauge (462) may be substituted with the gauge (482) shown in FIG. 12, which includes a digital display (484) showing the pressure reading in numerical form. Other suitable forms that gauge (462) may take will be apparent to those of ordinary skill in the art in view of the teachings herein. In the present example, gauge (462) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (462) may thus provide the operator with real time feedback indicating the fluid pressure within dilator (22) to enable the operator to determine whether the desired pressure level has been achieved.

In an exemplary use of inflator (450), a operator may start with actuator levers (464) at a position corresponding to crank pin (455) being located at position "A," which further corresponds to plunger (467) being at a distal position in body (460). The operator may then position port (470) in a bowl or other container of saline to draw fluid from. In instances where port (470) is coupled with one end of flexible tube (46), the operator may position the other end of flexible tube (46) in the saline. In either case, the operator may then pivot actuator levers (464) to a position corresponding to crank pin (455) being located at position "C," which further corresponds to plunger (467) being at a proximal position in body (460). This proximal movement of plunger (467) draws the saline (or other fluid) into reservoir (468). The operator may then remove port (470) or flexible tube (46) from the saline container and pivot actuator levers (464) to a position corresponding to crank pin (455) being located at position "B," which further corresponds to plunger (467) being at an intermediate position in body (460). It should be understood that transitioning crank pin (455) from position "A" to position "C" will entail pivoting actuator levers (464) in a first direction; while transitioning crank pin (455) from position "C" to position "B" will entail pivoting actuator levers (464) in a second direction. It should also be understood that the distal movement of plunger (467) resulting from the transition of crank pin (455) from position "C" to position "B" may purge air from reservoir (468). For instance, the operator may orient inflator (450) such that port (470) is positioned upwardly to gather air at the top of reservoir (468) before advancing plunger (467) distally in order to purge air from reservoir (468).

Once reservoir (468) has been sufficiently filled with fluid and air has been purged, the operator may couple inflator (450) with dilation catheter (20), such as by coupling port (470) with lateral port (26) via a flexible tube (46). With dilator (22) being suitably positioned within an anatomical passageway (e.g., an ostium (O), etc.), the operator may then pivot actuator levers (464) to a position corresponding to crank pin (455) being located back at position "A," which again corresponds to plunger (467) being at a distal position in body (460). This drives fluid from reservoir (468) to dilator (22) to thereby inflate dilator (22). In some instances, the volumes are all known and predetermined, such that dilator (22) always reaches an appropriate pressure level as soon as plunger (467) reaches a position associated with crank pin (455) being located at position "A." Thus, in some such versions, gauge (462) may be omitted. In some other versions, inflator (450) may permit a fine level of fluid pressure adjustment, via levers (464) or otherwise, after plunger (467) reaches a position associated with crank pin (455) being located at position "A."

Once the operator has attained the desired level of pressure in dilator (22) within the anatomical passageway to dilate the anatomical passageway, the operator may pause for an approximate, predetermined period of time (e.g., approximately three seconds, etc.). The operator may then once again pivot levers (464) to move crank pin (455) back to position "B," which will cause plunger (467) to retract back to the intermediate position, which will in turn withdraw the fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (468) may be used repeatedly to dilate a plurality of anatomical passageways, without having to withdraw dilator (22) from the patient, and without having to decouple inflator (450) from the rest of dilator catheter system (10), until all of the desired dilations have been completed.

Other suitable variations of inflator (450) will be apparent to those of ordinary skill in the art in view of the teachings herein. Similarly, other suitable ways in which inflator (450) may be used will be apparent to those of ordinary skill in the art in view of the teachings herein.

E. Exemplary Alternative Inflator with Knob Actuated Crankshaft

Figure 13:
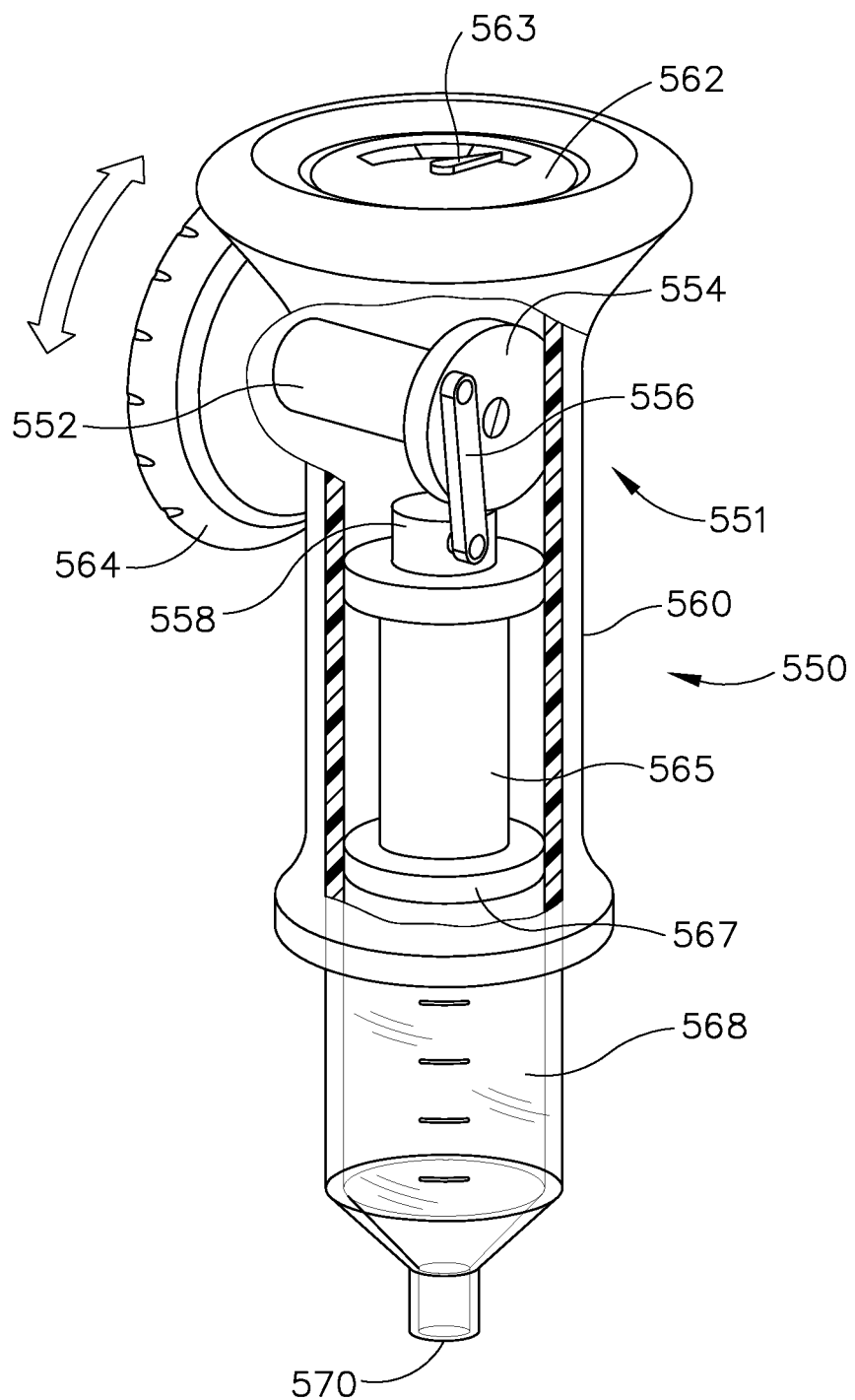
FIG. 13 depicts a perspective view of another exemplary inflator suited for use with the dilator catheter system of FIG. 1.

FIG. 13 shows another exemplary inflator (550), which is substantially similar to inflator (450) described above. Inflator (550) of this example comprises a body (560), an actuator knob (564), and a pressure gauge (562). Body (560) of the present example is formed as a substantially hollow cylinder, similar to syringe barrel (42) described above, although other suitable configurations may be used. Body (560) comprises a reservoir (568), a distal port (570), and a crank shaft assembly (551) at the proximal end of body (560). A rod (565) is longitudinally driven by crank shaft assembly (551) in a manner similar to rod (465) being driven by crank shaft assembly (451) described above. Plunger (567) is coupled to a distal end of rod (565) and extends outwardly to the inner diameter of body (560) to form a substantially fluid tight seal with body (560). The volume between plunger (567) and the distal end of body (560) forms reservoir (568). Reservoir (568) may be configured to hold about 3 to about 5 cc of fluid (e.g., saline). Rod (565) and plunger (567) may translate proximally and distally to adjust the size of reservoir (568). When rod (565) and plunger (567) translate proximally, the volume of reservoir (568) increases. When rod (565) and plunger (567) translate distally, the volume of reservoir (568) decreases. Port (570) at the distal end of body (560) is in fluid communication with reservoir (568) such that fluid may flow into and out of reservoir (568) via port (570). Port (570) may be coupled with flexible tube (46) of dilator catheter system (10).

Crank shaft assembly (551) comprises a crank shaft (552) and a crank wheel (554). Crank shaft (552) and crank wheel (554) are coaxial with each other and rotate unitarily with each other. Actuator knob (564) is secured to one end of crank shaft (552). In some other versions, an additional actuator knob (564) may be secured to the other end of crank shaft (552). Actuator knob (564) is operable to rotate crank shaft (552) and crank wheel (554) relative to body (560), about the axis shared by crank shaft (552) and crank wheel (554). A connecting rod (556) is pivotally coupled with an off center crank pin of crank wheel (554); and is further pivotally coupled with a pin at the head (558) of rod (565). These couplings may include bushings, bearings, and/or other features to provide smooth pivoting movement of connecting rod (556) relative to crank wheel (554) and head (558). It should be understood that the configuration of crank shaft assembly (551) will provide reciprocation of rod (565) and plunger (567) in response to rotation of actuator knob (564) relative to body (560).

In the present example, actuator knob (564), crank shaft (552), and crank wheel (554) are operable to rotate through a range of approximately 150°. Alternatively, any other suitable angular range may be provided. In instances providing a limited angular range, the limits may be imposed by bosses or other features that provide hard stops preventing rotation of actuator knob (564), crank shaft (552), and crank wheel (554) beyond the predetermined range. In some versions, there are three predetermined angular positions within the range—such as positions substantially similar to position "A," position "B," and position "C" shown in FIG. 10. These angular positions are associated with the location of the crank pin at particular stages of use of inflator (550) as will be described in greater detail below. It should be understood that inflator (550) may include detent features (and/or some other type of feature(s)) that provide the operator with audible and/or tactile feedback to indicate arrival at position "A," position "B," and/or position "C." In some other versions, a detent feature is only used to indicate arrival at position "B," while hard stops indicate arrival at position "A" and position "B." Other suitable forms of feedback will be apparent to those of ordinary skill in the art in view of the teachings herein.

Gauge (562) of the present example is positioned at the proximal end of body (560), and includes a pivoting pin (563) that indicates fluid pressure based on the angular position of the pin. Alternatively, gauge (562) may provide any other suitable type of indication of fluid pressure, including but not limited to the other types of fluid pressure indication described herein. In the present example, gauge (562) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (562) may thus provide the operator with real time feedback indicating the fluid pressure within dilator (22) to enable the operator to determine whether the desired pressure level has been achieved.

In an exemplary use of inflator (550), a operator may start with actuator knob (564) at a position corresponding to the crank pin being located at position "A," which further corresponds to plunger (567) being at a distal position in body (560). The operator may then position port (570) in a bowl or other container of saline to draw fluid from. In instances where port (570) is coupled with one end of flexible tube (46), the operator may position the other end of flexible tube (46) in the saline. In either case, the operator may then rotate actuator knob (564) to a position corresponding to the crank pin being located at position "C," which further corresponds to plunger (567) being at a proximal position in body (560). This proximal movement of plunger (567) draws the saline (or other fluid) into reservoir (568). The operator may then remove port (570) or flexible tube (46) from the saline container and rotate actuator knob (564) to a position corresponding to the crank pin being located at position "B," which further corresponds to plunger (567) being at an intermediate position in body (560). It should be understood that transitioning the crank pin from position "A" to position "C" will entail rotating actuator knob (564) in a first direction; while transitioning the crank pin from position "C" to position "B" will entail rotating actuator knob (564) in a second direction. It should also be understood that the distal movement of plunger (567)

resulting from the transition of the crank pin from position "C" to position "B" may purge air from reservoir (568). For instance, the operator may orient inflator (550) such that port (570) is positioned upwardly to gather air at the top of reservoir (568) before advancing plunger (567) distally in order to purge air from reservoir (568).

Once reservoir (568) has been sufficiently filled with fluid and air has been purged, the operator may couple inflator (550) with dilation catheter (20), such as by coupling port (570) with lateral port (26) via a flexible tube (46). With dilator (22) being suitably positioned within an anatomical passageway (e.g., an ostium (O), etc.), the operator may then rotate actuator knob (564) to a position corresponding to the crank pin being located back at position "A," which again corresponds to plunger (567) being at a distal position in body (560). This drives fluid from reservoir (568) to dilator (22) to thereby inflate dilator (22). In some instances, the volumes are all known and predetermined, such that dilator (22) always reaches an appropriate pressure level as soon as plunger (567) reaches a position associated with the crank pin being located at position "A." Thus, in some such versions, gauge (562) may be omitted. In some other versions, inflator (550) may permit a fine level of fluid pressure adjustment, via knob (564) or otherwise, after plunger (567) reaches a position associated with the crank pin being located at position "A."

Once the operator has attained the desired level of pressure in dilator (22) within the anatomical passageway to dilate the anatomical passageway, the operator may pause for an approximate, predetermined period of time (e.g., approximately three seconds, etc.). The operator may then once again rotate knob (564) to move the crank pin back to position "B," which will cause plunger (567) to retract back to the intermediate position, which will in turn withdraw the fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (568) may be used repeatedly to dilate a plurality of anatomical passageways, without having to withdraw dilator (22) from the patient, and without having to decouple inflator (550) from the rest of dilator catheter system (10), until all of the desired dilations have been completed.

Other suitable variations of inflator (550) will be apparent to those of ordinary skill in the art in view of the teachings herein. Similarly, other suitable ways in which inflator (550) may be used will be apparent to those of ordinary skill in the art in view of the teachings herein.

F. Exemplary Alternative Inflator with Knob Actuated Eccentric Cam

Figure 14:
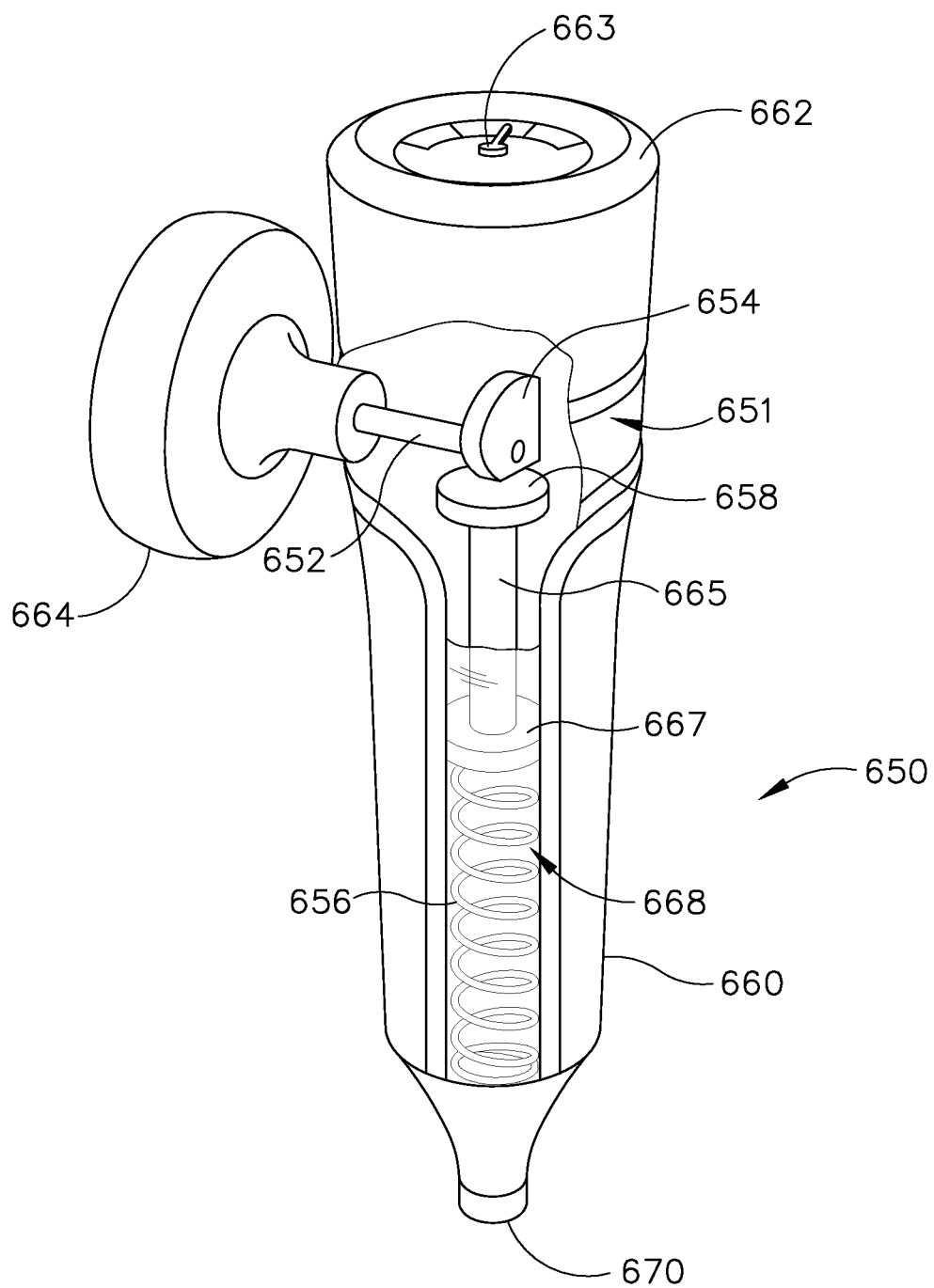
FIG. 14 depicts a perspective view of another exemplary inflator suited for use with the dilator catheter system of FIG. 1.

FIG. 14 depicts another exemplary inflator (650). Inflator (650) of this example comprises a body (660), an actuator knob (664), and a pressure gauge (662). Body (660) of the present example is formed as a substantially hollow cylinder, similar to syringe barrel (42) described above, although other suitable configurations may be used. Body (660) comprises a reservoir (668), a distal port (670), and a cam drive assembly (651) at the proximal end of body (660). A rod (665) is longitudinally driven by cam drive assembly (651) as will be described in greater detail below. Plunger (667) is coupled to a distal end of rod (665) and extends outwardly to the inner diameter of body (660) to form a substantially fluid tight seal with body (660). The volume between plunger (667) and the distal end of body (660) forms reservoir (668). Reservoir (668) may be configured to hold about 3 to about 5 cc of fluid (e.g., saline). Rod (665) and plunger (667) may translate proximally and distally to adjust the size of reservoir (668). When rod (665) and plunger (667) translate proximally, the volume of reservoir (668) increases. When rod (665) and plunger (667) translate distally, the volume of reservoir (668) decreases. Port (670) at the distal end of body (660) is in fluid communication with reservoir (668) such that fluid may flow into and out of reservoir (668) via port (670). Port (670) may be coupled with flexible tube (46) of dilator catheter system (10).

Cam drive assembly (651) comprises a cam shaft (652) and a rotary cam (654). Cam shaft (652) and rotary cam (654) rotate unitarily with each other. Actuator knob (664) is secured to one end of cam shaft (652). In some other versions, an additional actuator knob (664) may be secured to the other end of cam shaft (652). Actuator knob (664) is operable to rotate cam shaft (652) and rotary cam (654) relative to body (660), about the axis defined by cam shaft (652). Rotary cam (654) has an asymmetric profile that includes a round section and a flat section. Rotary cam (654) is also eccentrically disposed relative to the longitudinal axis of cam shaft (652). The outer perimeter of rotary cam (654) is positioned to engage a cam plate (658), which is secured to the proximal end of rod (665). A coil spring (656) resiliently biases rod (665) proximally, thereby urging cam plate (658) into engagement with rotary cam (654). While coil spring (656) is located in reservoir (668) in the present example, it should be understood that coil spring (656) may be located elsewhere. For instance, coil spring (656) may be positioned above cam plate (658), and may pull cam plate (658) into engagement with rotary cam (654) instead of pushing cam plate (658) into engagement with rotary cam (654). It should also be understood that any other suitable type of component(s) may be used to provide a resilient bias to cam plate (658), in addition to or in lieu of coil spring (656). In some other versions, a torsion spring is coupled to cam shaft (652) and coil spring (656) is omitted.

In the present example, the asymmetric profile of rotary cam (654) and the eccentric positioning of rotary cam (654) on cam shaft (652) provide translation of cam plate (658), and thereby translation of rod (665) and plunger (667), in response to rotation of knob (664). In some versions, rotary cam (654) includes flats along its perimeter, with such flats corresponding to certain stages of use of inflator (650) similar to those associated with crank pin positions "A," "B," and "C," described above with respect to inflators (450, 550). These flats may also provide tactile feedback to the operator. For instance, as the operator rotates knob (664) to transition from one stage to another, the operator may feel a slight resistance as rotary cam (654) bears against cam plate (658) during the transition from one flat of rotary cam (654) to the next flat. Once the next flat reaches cam plate (658), knob (664) may effectively come to an abrupt stop, providing a sudden change in force required for further rotation. The operator may thus sense the arrival at the next operational stage by feeling the change in force through knob (664). Other suitable forms of feedback will be apparent to those of ordinary skill in the art in view of the teachings herein.

Gauge (662) of the present example is positioned at the proximal end of body (660), and includes a pivoting pin (663) that indicates fluid pressure based on the angular position of the pin. Alternatively, gauge (662) may provide any other suitable type of indication of fluid pressure, including but not limited to the other types of fluid pressure indication described herein. In the present example, gauge (662) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (662) may thus provide the operator with real time feedback indicating the fluid pressure within dilator (22) to enable the operator to determine whether the desired pressure level has been achieved.

In an exemplary use of inflator (650), a operator may start with actuator knob (664) at a position corresponding to plunger (667) being located at a distal position in body (660). The operator may then position port (670) in a bowl or other container of saline to draw fluid from. In instances where port (670) is coupled with one end of flexible tube (46), the operator may position the other end of flexible tube (46) in the saline. In either case, the operator may then rotate actuator knob (664) to a position corresponding to plunger (667) being located at a proximal position in body (660). In particular, this rotation of knob (664) repositions rotary cam (654) such that a flat or other perimeter feature provides clearance for cam plate (658) to travel proximally, which cam plate (658) does under the resilient bias provided by spring (656). The resulting proximal movement of plunger (667) draws the saline (or other fluid) into reservoir (668). The interaction between cam plate (658) and a flat or other feature on rotary cam (654) may provide tactile feedback to the operator via knob (664), indicating that plunger (667) has reached the proximal position. The operator may then remove port (670) or flexible tube (46) from the saline container and rotate actuator knob (664) to a position corresponding to plunger (667) being located at a longitudinally intermediate position in body (660). Again, this rotation of knob (664) repositions rotary cam (654) such that a perimeter feature of rotary cam (654) drives cam plate (658) distally. The resulting distal movement of plunger (667) may purge air from reservoir (668). For instance, the operator may orient inflator (650) such that port (670) is positioned upwardly to gather air at the top of reservoir (668) before advancing plunger (667) distally in order to purge air from reservoir (668). The interaction between cam plate (658) and a flat or other feature on rotary cam (654) may provide tactile feedback to the operator via knob (664), indicating that plunger (667) has reached the intermediate position.

Once reservoir (668) has been sufficiently filled with fluid and air has been purged, the operator may couple inflator (650) with dilation catheter (20), such as by coupling port (670) with lateral port (26) via a flexible tube (46). With dilator (22) being suitably positioned within an anatomical passageway (e.g., an ostium (O), etc.), the operator may then rotate actuator knob (664) to a position corresponding to plunger (667) being at a distal position in body (660). Again, this rotation of knob (664) repositions rotary cam (654) such that a perimeter feature of rotary cam (654) drives cam plate (658) distally. The resulting distal movement of plunger (667) drives fluid from reservoir (668) to dilator (22) to thereby inflate dilator (22). The interaction between cam plate (658) and a flat or other feature on rotary cam (654) may provide tactile feedback to the operator via knob (664), indicating that plunger (667) has reached the distal position. In some instances, the volumes are all known and predetermined, such that dilator (22) always reaches an appropriate pressure level as soon as rotary cam (654) reaches a position where plunger (667) is driven to a distal-most position. Thus, in some such versions, gauge (662) may be omitted. In some other versions, inflator (650) may permit a fine level of fluid pressure adjustment, via knob (664) or otherwise, after plunger (667) is driven to a distal position associated by rotary cam (654).

Once the operator has attained the desired level of pressure in dilator (22) within the anatomical passageway to dilate the anatomical passageway, the operator may pause for an approximate, predetermined period of time (e.g., approximately three seconds, etc.). The operator may then once again rotate knob (664) to cause plunger (667) to retract back to the intermediate position, which will in turn withdraw the fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (668) may be used repeatedly to dilate a plurality of anatomical passageways, without having to withdraw dilator (22) from the patient, and without having to decouple inflator (650) from the rest of dilator catheter system (10), until all of the desired dilations have been completed.

Other suitable variations of inflator (650) will be apparent to those of ordinary skill in the art in view of the teachings herein. Similarly, other suitable ways in which inflator (650) may be used will be apparent to those of ordinary skill in the art in view of the teachings herein.

G. Exemplary Alternative Inflator with Palm Grip and Thumb Drive

Figure 15:
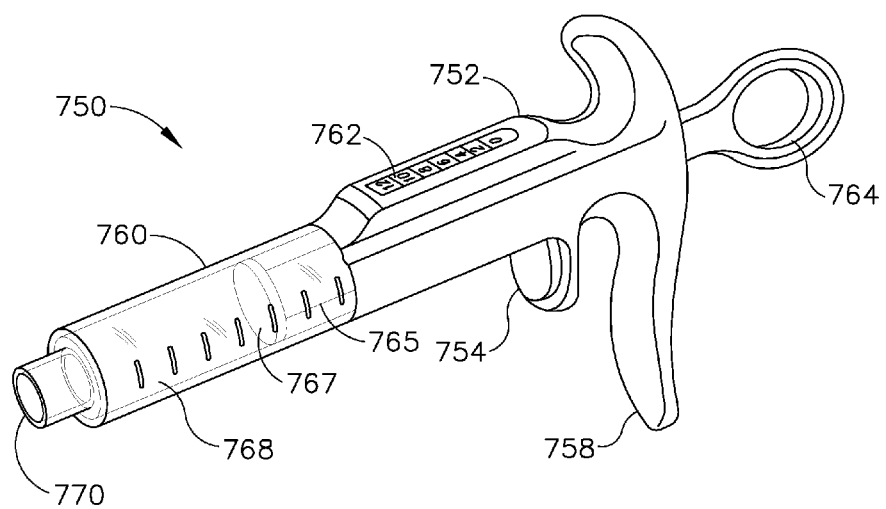
FIG. 15 depicts a perspective view of another exemplary inflator suited for use with the dilator catheter system of FIG. 1.

FIG. 15 depicts another exemplary inflator (750). Inflator (750) of this example is configured for one-handed operation. Inflator (750) of this example comprises a body (760), an actuator (764), and a pressure gauge (762). Body (760) of the present example is formed as a substantially hollow cylinder, similar to syringe barrel (42) described above, although other suitable configurations may be used. Body (760) comprises a reservoir (768), a distal port (770), and a handle (758) at the proximal end of body (760). A rod (765) extends into body (760). Plunger (767) is coupled to a distal end of rod (765) and extends outwardly to the inner diameter of body (760) to form a substantially fluid tight seal with body (760). The volume between plunger (767) and the distal end of body (760) forms reservoir (768). Reservoir (768) may be configured to hold about 3 to about 5 cc of fluid (e.g., saline). Rod (765) and plunger (767) may translate proximally and distally to adjust the size of reservoir (768). When rod (765) and plunger (767) translate proximally, the volume of reservoir (768) increases. When rod (765) and plunger (767) translate distally, the volume of reservoir (768) decreases. Port (770) at the distal end of body (760) is in fluid communication with reservoir (768) such that fluid may flow into and out of reservoir (768) via port (770). Port (770) may be coupled with flexible tube (46) of dilator catheter system (10).

Actuator (764) is unitarily secured to rod (765), such that actuator (764) and rod (765) (and, hence, plunger (767)) translate unitarily relative to body (760). In some versions, a coil spring (not shown) and/or some other type of resilient member resiliently biases actuator (764) proximally, though this is of course merely optional. Actuator (764) includes a ring that is configured to receive a operator's thumb. Handle (758) of body (760) is configured such that a operator may wrap his or her fingers around handle (758) with the thumb of the same hand being disposed in the ring of actuator (764). The operator may thus drive actuator (764) distally relative to handle (758), and retract actuator (764) proximally relative to handle (758), using just that single hand. Plunger (767) translates relative to body (760) accordingly.

Inflator (750) of this example also includes a lock/unlock button (754) positioned near handle (758). It should be understood that button (754) may be positioned such that it can be actuated by the same single hand that is being used to hold handle (758) and drive actuator (764), without that hand having to be repositioned to transition among any of those operations. In some versions, inflator (750) includes a locking assembly that will lock the longitudinal position of actuator (764), rod (765), and plunger (767) relative to body (760) unless button (754) is being depressed. For instance, at least part of rod (765) may include sawteeth and/or some other locking feature(s) that are engaged by a pawl or other type of ratcheting feature. The pawl or other type of ratcheting feature may be resiliently biased to engage that part of rod (765), such that the longitudinal position of actuator (764), rod (765), and plunger (767) relative to body (760) will be locked by default. When the operator wishes to translate actuator (764), rod (765), and plunger (767) relative to body (760), the operator presses button (754) to release the pawl or other type of ratcheting feature from the locking feature(s) of rod (765). Once the desired longitudinal position has been reached, the operator may release button (754) to selectively lock actuator (764), rod (765), and plunger (767) at the longitudinal position. As another merely illustrative example, actuator (764), rod (765), and plunger (767) may be configured to translate freely relative to body (760) by default, and button (754) may be configured to lock the longitudinal position of actuator (764), rod (765), and plunger (767) when button (754) is being depressed. Button (754) may thus serve as a brake in such instances. Various suitable ways in which button (754) may selectively lock and/or unlock the longitudinal position of actuator (764), rod (765), and plunger (767) relative to body (760) will be apparent to those of ordinary skill in the art in view of the teachings herein.

Gauge (762) of the present example is positioned proximal to reservoir (768) and is configured to measure the pressure within dilator catheter system (10). Gauge (762) of this example comprises a U-tube type of liquid column gauge or manometer. Graduated markings adjacent to the liquid column in gauge (762) indicate the numerical value of the fluid pressure. Alternatively, gauge (762) may provide any other suitable type of indication of fluid pressure, including but not limited to the other types of fluid pressure indication described herein. In the present example, gauge (762) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (762) may thus provide the operator with real time feedback indicating the fluid pressure within dilator (22) to enable the operator to determine whether the desired pressure level has been achieved.

In an exemplary use of inflator (750), a operator may start with plunger (767) advanced to a distal position in body (760). This may be accomplished by driving actuator (764) toward handle (758) with the operator's thumb. The operator may then position port (770) in a bowl or other container of saline to draw fluid from. In instances where port (770) is coupled with one end of flexible tube (46), the operator may position the other end of flexible tube (46) in the saline. In either case, the operator may then pull actuator (764) proximally relative to handle (758) with the operator's thumb. This will in turn retract plunger (767) relative to body (760) to draw the saline (or other fluid) into reservoir (768). The operator may then remove port (770) or flexible tube (46) from the saline container and advance plunger (767) distally in order to purge air from reservoir (768). For instance, the operator may orient inflator (750) such that port (770) is positioned upwardly to gather air at the top of reservoir (768) before advancing plunger (767) distally in order to purge air from reservoir (768).

Once reservoir (768) has been sufficiently filled with fluid and air has been purged, the operator may couple inflator (750) with dilation catheter (20), such as by coupling port (770) with lateral port (26) via a flexible tube (46). With dilator (22) being suitably positioned within an anatomical passageway (e.g., an ostium (O), etc.), the operator may then drive actuator (764) distally toward handle (758) with the operator's thumb, in order to transfer fluid from reservoir (768) to dilator (22). The operator may observe the pressure reading at gauge (762) while advancing actuator (764) distally in order to determine when the appropriate fluid pressure level has been reached.

Once the operator has attained the desired level of pressure in dilator (22) within the anatomical passageway to dilate the anatomical passageway, the operator may pause for an approximate, predetermined period of time (e.g., approximately three seconds, etc.). The operator may then pull actuator (764) proximally relative to handle (758) with the operator's thumb. This will in turn retract plunger (767) relative to body (760) to draw fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (768) may be used repeatedly to dilate a plurality of anatomical passageways, without having to withdraw dilator (22) from the patient, and without having to decouple inflator (750) from the rest of dilator catheter system (10), until all of the desired dilations have been completed.

In some instances, rod (765) and body (760) include complementary detent features (and/or some other type of feature(s)) that provide the operator with audible and/or tactile feedback. For instance, such features may provide the operator with feedback to indicate longitudinal positions of plunger (767) that are predeterminedly associated with an appropriate pressure level in dilator (22). In addition or in the alternative, such features may provide the operator with feedback to indicate that the longitudinal position of plunger (767) is getting close to a position that is predeterminedly associated with an appropriate pressure level in dilator (22), thereby alerting the operator to slow their distal advancement of actuator (764) and carefully watch gauge (762). Detent features (and/or some other type of feature(s)) may also provide the operator with audible and/or tactile feedback to indicate when plunger (767) has reached a position that is predeterminedly associated with air being purged from reservoir (768) before port (770) is coupled with lateral port (26). Other suitable variations of inflator (750) will be apparent to those of ordinary skill in the art in view of the teachings herein. Similarly, other suitable ways in which inflator (750) may be used will be apparent to those of ordinary skill in the art in view of the teachings herein.

H. Exemplary Alternative Inflator with Rotary Drive and Button Release

Figure 16:
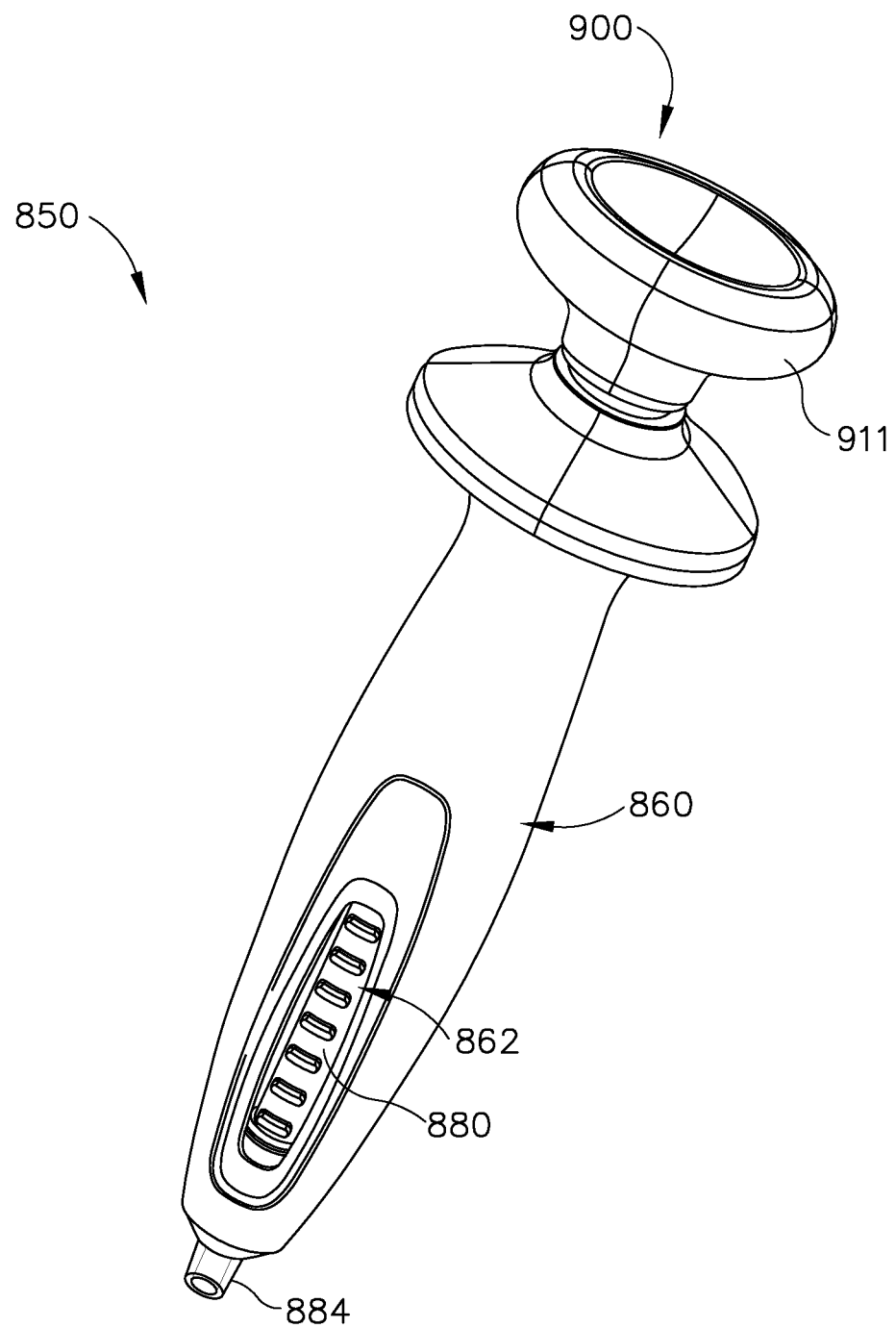
FIG. 16 depicts a perspective view of another exemplary inflator suited for use with the dilator catheter system of FIG. 1.
Figure 17:
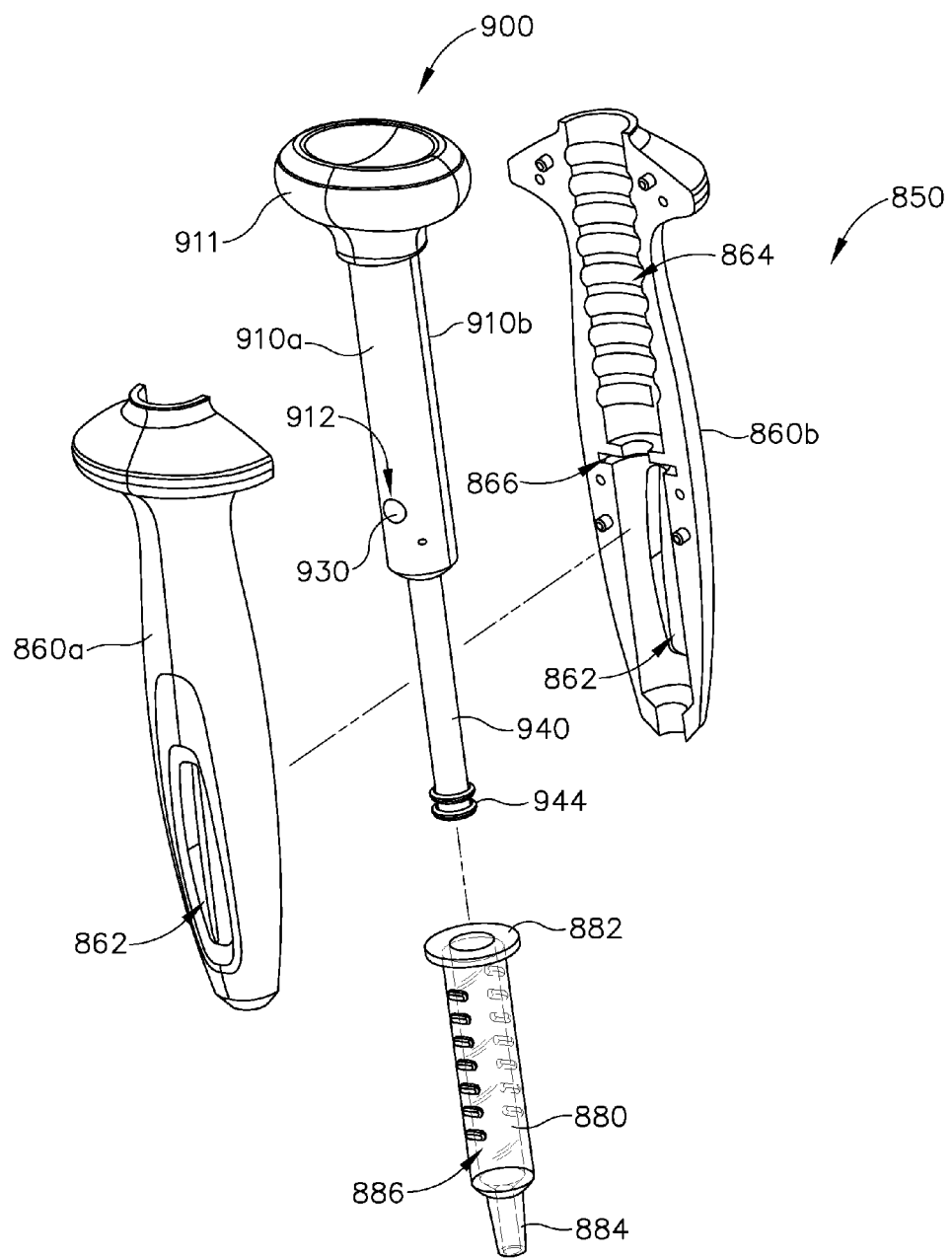
FIG. 17 depicts an exploded view of the inflator of FIG. 16.
Figure 18:
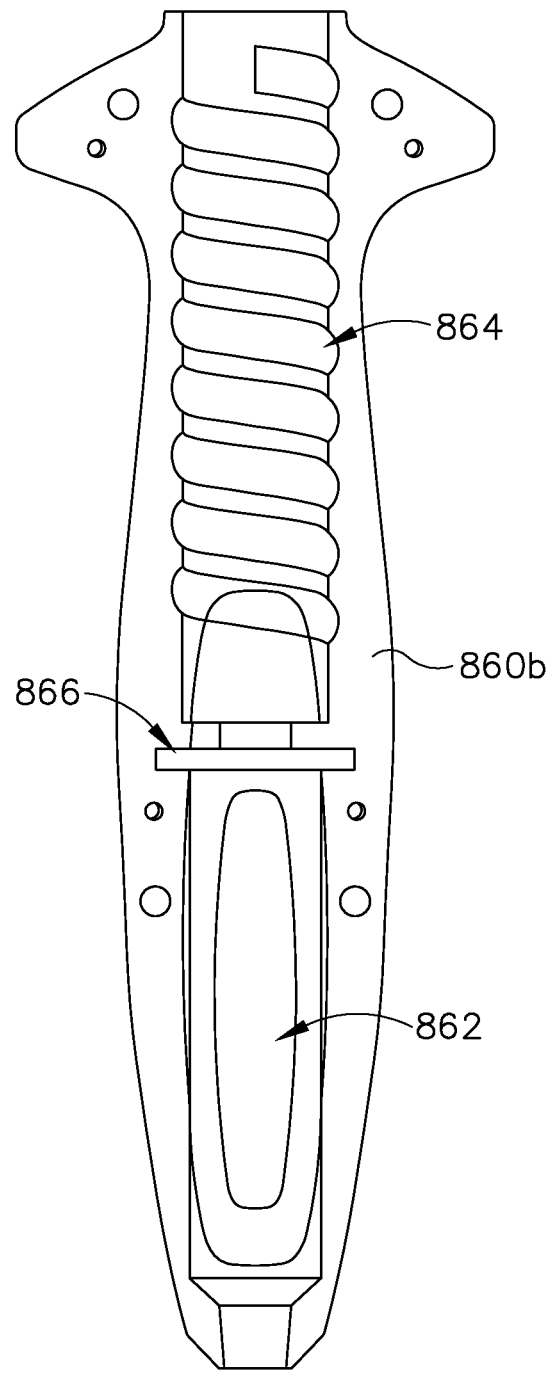
FIG. 18 depicts a side elevational view of a housing half of the inflator of FIG. 16.

FIGS. 16-20C depict another exemplary inflator (850). Inflator (850) of this example includes a housing (860), a syringe barrel (880), and a plunger actuation assembly (900). Housing (860) is formed by two halves (860a, 860b) that are joined together to contain syringe barrel (880) and plunger actuation assembly (900). As best seen in FIGS. 16-18, each half (860a, 860b) includes a window (862) that permits viewing of syringe barrel (880). In particular, a operator of inflator (850) may see how much fluid is in syringe barrel (880) by viewing syringe barrel (880) through window (862). As best seen in FIG. 18, each half (860a, 860b) also includes a respective helically oriented groove (864) and flange recess (866). Grooves (864) of halves (860a, 860b) are configured to align with each other when halves (860a, 860b) are joined, to form a continuous helical thread in housing (860). Flange recesses (866) of halves (860a, 860b) are configured to align with each other when halves (860a, 860b) are joined, to capture and retain the upper flange (882) of syringe barrel (880). The distal port (884) of syringe barrel (880) protrudes from housing (860). Distal port (884) is configured to communicate fluid to and from the reservoir (886) defined by syringe barrel (880).

Figure 19:
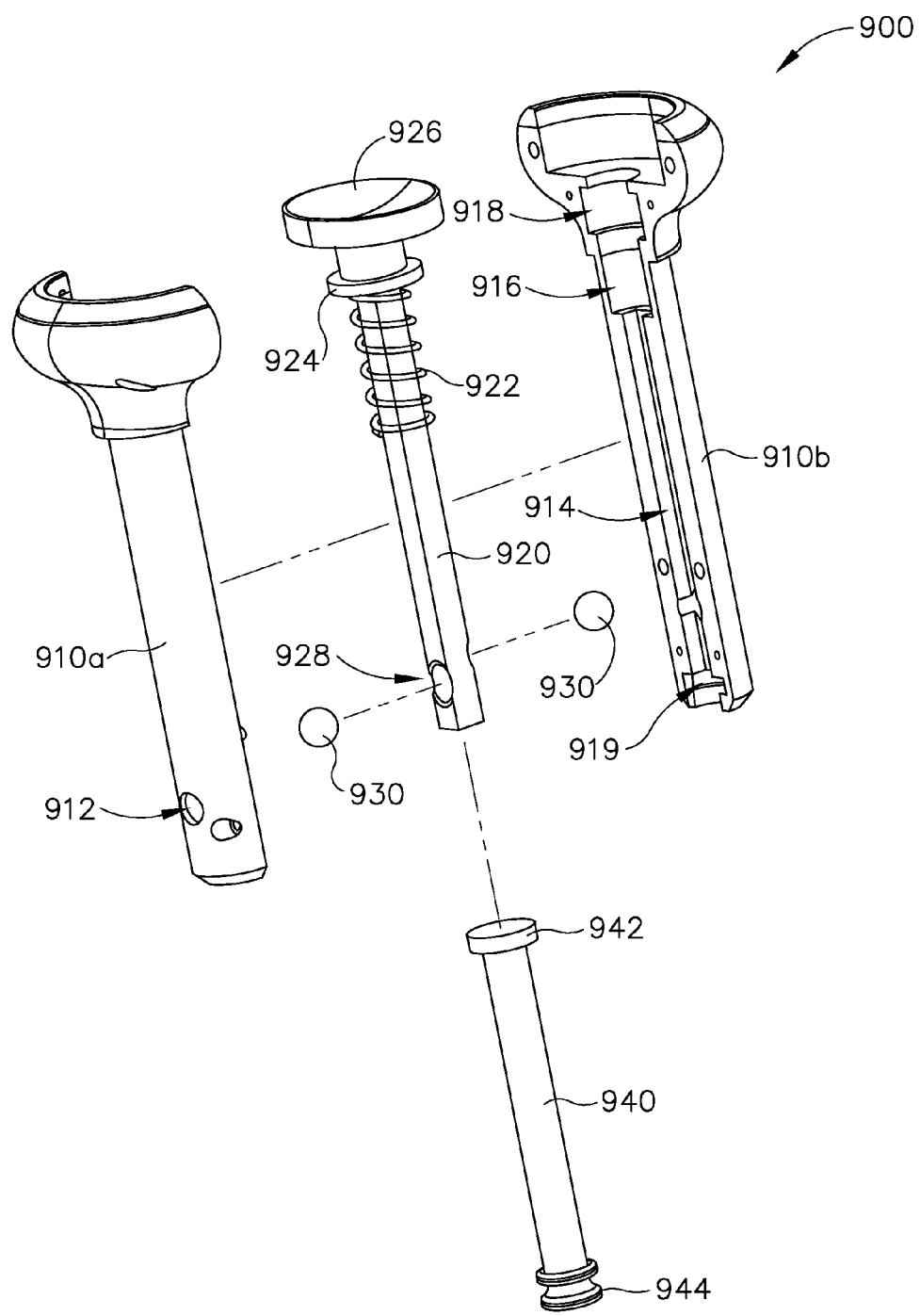
FIG. 19 depicts an exploded view of a plunger actuation assembly of the inflator of FIG. 16.

As shown in FIGS. 17 and 19, plunger actuation assembly (900) of this example comprises a pair of rotary actuator halves (910a, 910b), a translating rod (920), a pair of ball bearings (930), and a plunger (940). Rotary actuator halves (910a, 910b) cooperate to define a knob (911) when halves (910a, 910b) are assembled together. Each half (910a, 910b) has a respective bearing aperture (912), rod recess (914), spring recess (916), and a rod flange recess (918). Bearing apertures (912) are configured to enable portions of bearings (930) to protrude through apertures (912) without letting bearings (930) pass fully through apertures (912) when plunger actuation assembly (900) is assembled. When halves (910a, 910b) are assembled together, rod recesses (914) cooperate to slidingly receive rod (920), enabling rod to translate longitudinally relative to assembled halves (910a, 910b). Spring recesses (916) align with each other to capture the distal end of a spring (922), which is configured to resiliently bias rod (920) upwardly relative to assembled halves (910a, 910b). Rod flange recesses (918) together encompass a flange (924) of rod (920) and thereby constrain longitudinal movement of rod (920) relative to assembled halves (910a, 910b) while still permitting some degree of longitudinal movement of rod (920) relative to assembled halves (910a, 910b). As will be described in greater detail below, such translation of rod (920) selectively unlocks engagement between bearings (930) and grooves (864).

Each rotary actuator half (910a, 910b) also includes a plunger flange recess (919). Plunger flange recesses (919) cooperate to capture a proximal flange (942) of plunger (940). Plunger (940) thus translates unitarily with assembled halves (910a, 910b) relative to housing (860) and relative to syringe barrel (880). A piston (944) at the distal end of plunger (940) is positioned within syringe barrel (880). As also noted above, syringe barrel (880) is secured by housing (860). It should therefore be understood that plunger (940) is configured to reciprocate within syringe barrel (880) to selectively vary the volume of reservoir (886) in syringe barrel (880), to thereby draw fluid into or expel fluid from reservoir (886).

Figure 20A:
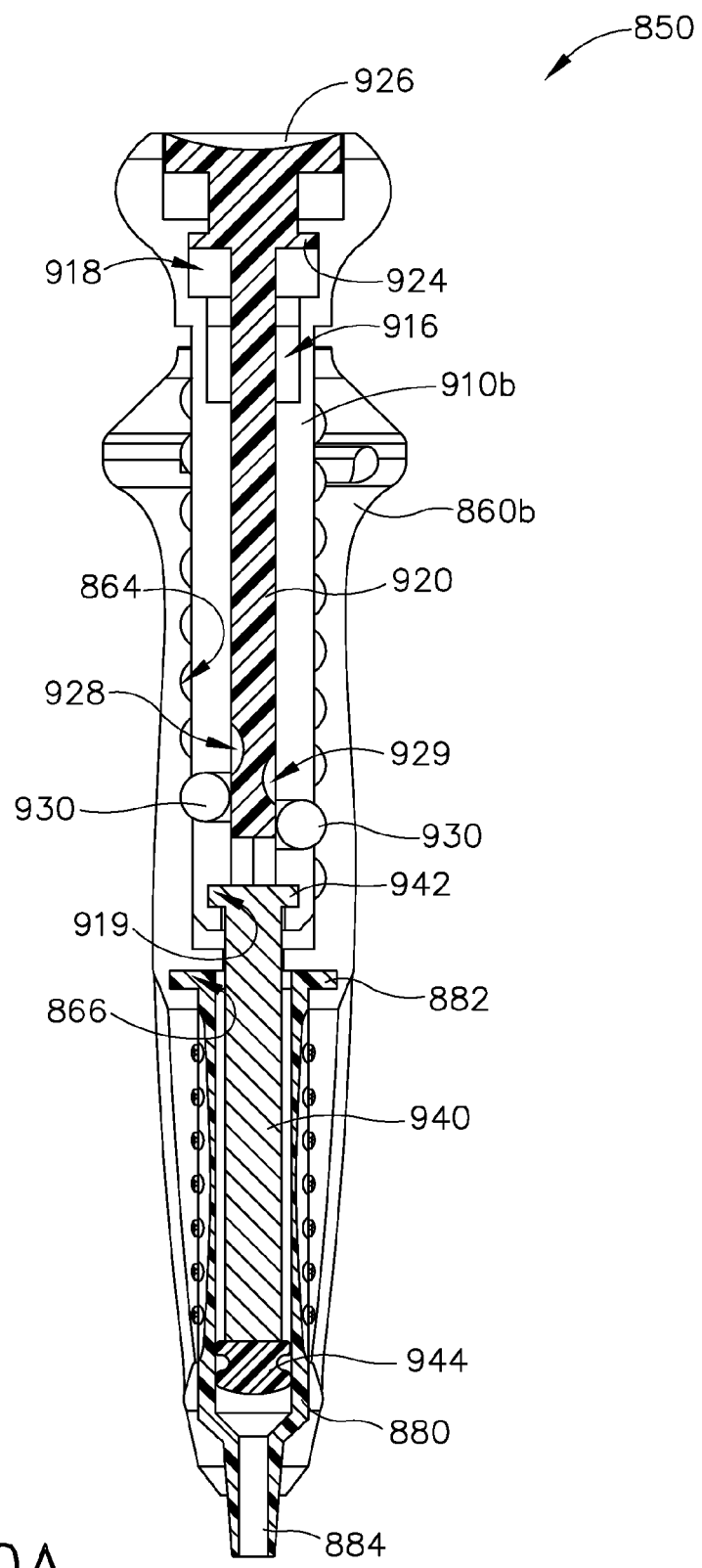
FIG. 20A depicts a cross-sectional side view of the inflator of FIG. 16, with the plunger actuation assembly in a distal and locked position.
Figure 20B:
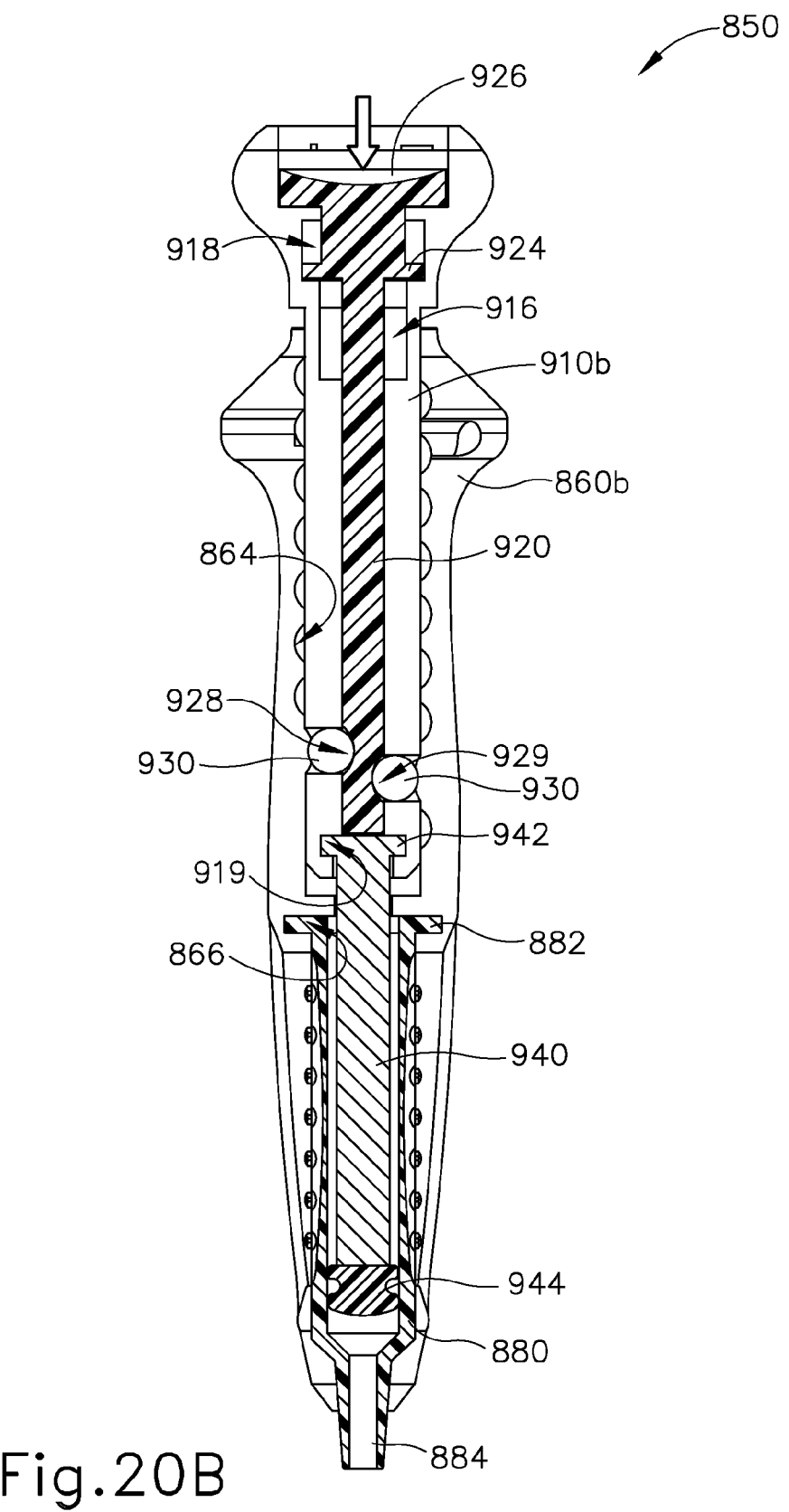
FIG. 20B depicts a cross-sectional side view of the inflator of FIG. 16, with the plunger actuation assembly in a distal and unlocked position.

As noted above, translating rod (920) of the present example comprises a spring (922) and a flange (924). While spring (922) of the present example comprises a coil spring, it should be understood that any other suitable type of resilient member may be used to resiliently bias rod (920). Rod (920) of the present example further includes a pushbutton (926), a first lateral recess (928), and a second lateral recess (929). Lateral recesses (928, 929) are positioned just proximal to the distal end of rod (920), and are sized to receive portions of bearings (930) when rod (920) is translated to a distal position as shown in FIG. 20B. Rod (920) is configured such that rod (920) drives bearings (930) outwardly when rod (920) is in a proximal position as shown in FIG. 20A (in which spring (922) is omitted). When bearings (930) are in this position, bearings (930) protrude through apertures (912) and engage grooves (864). When bearings (930) are engaged with grooves (864), bearings (930) prevent plunger actuation assembly (900) from translating freely relative to housing (860). However, the relationship between bearings (930) and the helical threading formed by grooves (864) will provide translation of plunger actuation assembly (900) when plunger actuation assembly (900) is rotated relative to housing (860). When rod (920) is translated to the distal position shown in FIG. 20B, bearings (930) retract into recesses (928, 929), disengaging grooves (864). When bearings (930) are disengaged from grooves (864), plunger actuation assembly (900) translates freely relative to housing (860). While grooves (928, 929) are longitudinally offset relative to each other in the present example, it should be understood that grooves (928, 929) may alternatively be located at a common longitudinal position.

Figure 20C:
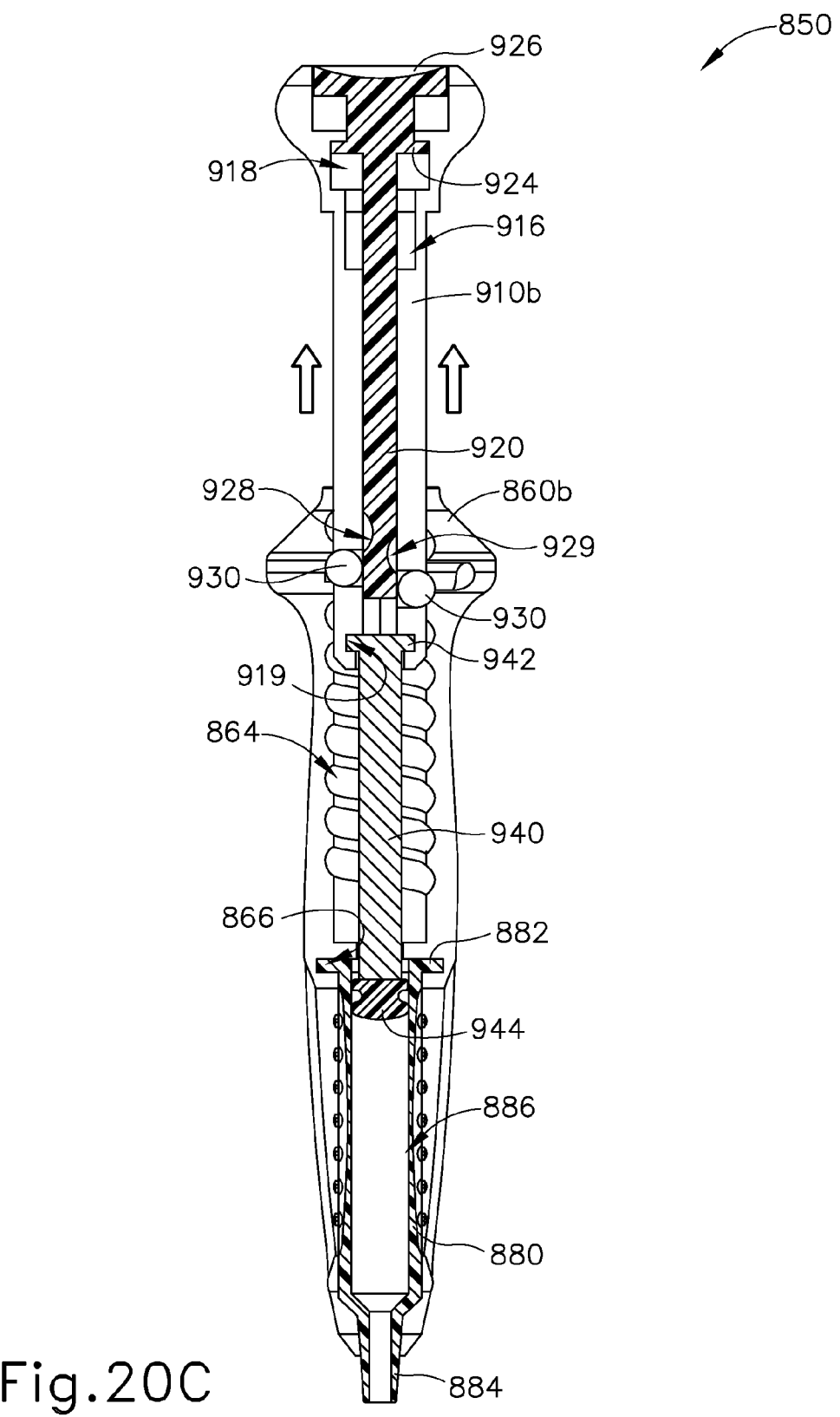
FIG. 20C depicts a cross-sectional side view of the inflator of FIG. 16, with the plunger actuation assembly in a proximal and locked position.
Figure 21:
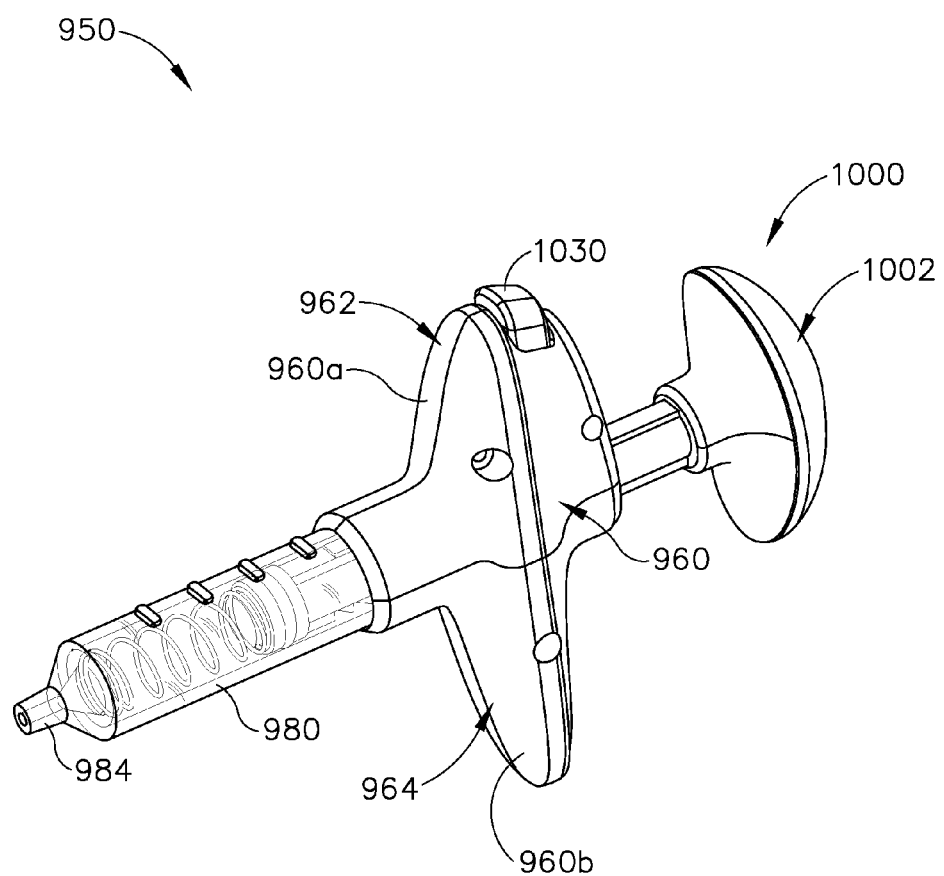
FIG. 21 depicts a perspective view of another exemplary inflator suited for use with the dilator catheter system of FIG. 1.

In an exemplary use of inflator (850), a operator may start with plunger (940) advanced to a distal position as shown in FIG. 20A. The operator may then position port (884) in a bowl or other container of saline to draw fluid from. In instances where port (884) is coupled with one end of flexible tube (46), the operator may position the other end of flexible tube (46) in the saline. In either case, the operator may then advance rod (920) distally by pushing on pushbutton (926), thereby disengaging bearings (930) from grooves (864) as shown in FIG. 20B. Next, the operator may pull plunger actuation assembly (900) proximally relative to housing (860), which will in turn retract plunger (940) relative to syringe barrel (880) to draw the saline (or other fluid) into reservoir (886). The operator may then remove port (884) or flexible tube (46) from the saline container and release pushbutton (926). This will enable spring (922) to drive rod (920) upwardly relative to halves (910a, 910b), which will result in rod (920) driving bearings (930) outwardly into engagement with grooves (864) as shown in FIG. 20C.

At this stage, the operator may advance plunger (940) distally in order to purge air from reservoir (886). For instance, the operator may orient inflator (850) such that port (884) is positioned upwardly to gather air at the top of reservoir (886) before advancing plunger (940) distally in order to purge air from reservoir (886). To purge air from reservoir (886), the operator may depress pushbutton (926) again to disengage bearings (930) from grooves (864), then push plunger actuation assembly (900) distally relative to housing (860) to advance plunger (940) within syringe barrel (880). Alternatively, the operator may refrain from depressing pushbutton (926), and may instead rotate knob (911) relative to housing (860). Due to the engagement between bearings (930) and grooves (864) this rotation of knob (911) relative to housing (860) will drive plunger actuation assembly (900) distally relative to housing (860), thereby advancing plunger (940) within syringe barrel (880).

Once reservoir (886) has been sufficiently filled with fluid and air has been purged, the operator may couple inflator (850) with dilation catheter (20), such as by coupling port (884) with lateral port (26) via a flexible tube (46). In some instances, a conventional fluid pressure gauge (not shown) may be coupled in the fluid path between port (884) and lateral port (26) (e.g., via a "T" fitting, etc.). Of course, inflator (850) may alternatively include an integral pressure gauge. With dilator (22) being suitably positioned within an anatomical passageway (e.g., an ostium (O), etc.), the operator may then advance plunger actuation assembly (900) distally relative to housing (860) to advance plunger (940) within syringe barrel (880), thereby transferring fluid from reservoir (886) to dilator (22). The operator may observe the pressure reading at the pressure gauge while advancing plunger actuation assembly (900) distally in order to determine when the appropriate fluid pressure level has been reached.

In some instances, the advancement of plunger actuation assembly (900) occurs in two stages. In the first stage, the operator may depress pushbutton (926) again to disengage bearings (930) from grooves (864), then push plunger actuation assembly (900) distally relative to housing (860) to advance plunger (940) within syringe barrel (880) through a first range of motion that approaches but does not quite reach the desired fluid pressure. In the second stage, the operator may release pushbutton (926) to re-engage bearings (930) with grooves (864), then rotate knob (911) relative to housing (860) to drive plunger actuation assembly (900) distally relative to housing (860), thereby advancing plunger (940) within syringe barrel (880) through a second range of motion in a more precisely controlled fashion until reaching the desired fluid pressure.

Once the operator has attained the desired level of pressure in dilator (22) within the anatomical passageway to dilate the anatomical passageway, the operator may pause for an approximate, predetermined period of time (e.g., approximately three seconds, etc.). The operator may then depress pushbutton (926) to once again disengage bearings (930) from grooves (864), then pull plunger actuation assembly (900) proximally relative to housing (860). This will retract plunger (940) relative to syringe barrel (880), thereby drawing fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (886) may be used repeatedly to dilate a plurality of anatomical passageways, without having to withdraw dilator (22) from the patient, and without having to decouple inflator (850) from the rest of dilator catheter system (10), until all of the desired dilations have been completed. Other suitable variations of inflator (850) will be apparent to those of ordinary skill in the art in view of the teachings herein. Similarly, other suitable ways in which inflator (850) may be used will be apparent to those of ordinary skill in the art in view of the teachings herein.

I. Exemplary Alternative Inflator with Ratcheting Drive and Button Release

FIGS. 21-24E depict another exemplary inflator (950). Inflator (950) of this example includes a housing (960), a syringe barrel (980), and a plunger actuator (1000). Housing (960) is formed by two halves (960a, 960b) that are joined together to contain syringe barrel (980) and plunger actuator (1000). Housing (960) defines two finger grip features (962, 964) while the proximal end of plunger actuator (1000) includes a palm grip feature (1002). These grip features (962, 964, 1002) are configured to enable an operator to grasp and manipulate inflator (950) with a single hand by wrapping their fingers about finger grip features (962, 964) while positioning palm grip feature (1002) in the palm of the same hand. As will be described in greater detail below, inflator (950) may be selectively actuated by the operator squeezing their hand to drive plunger actuator (1000) distally relative to housing (960); or by releasing their grip to enable plunger actuator (1000) to retract proximally relative to housing (960).

Figure 22:
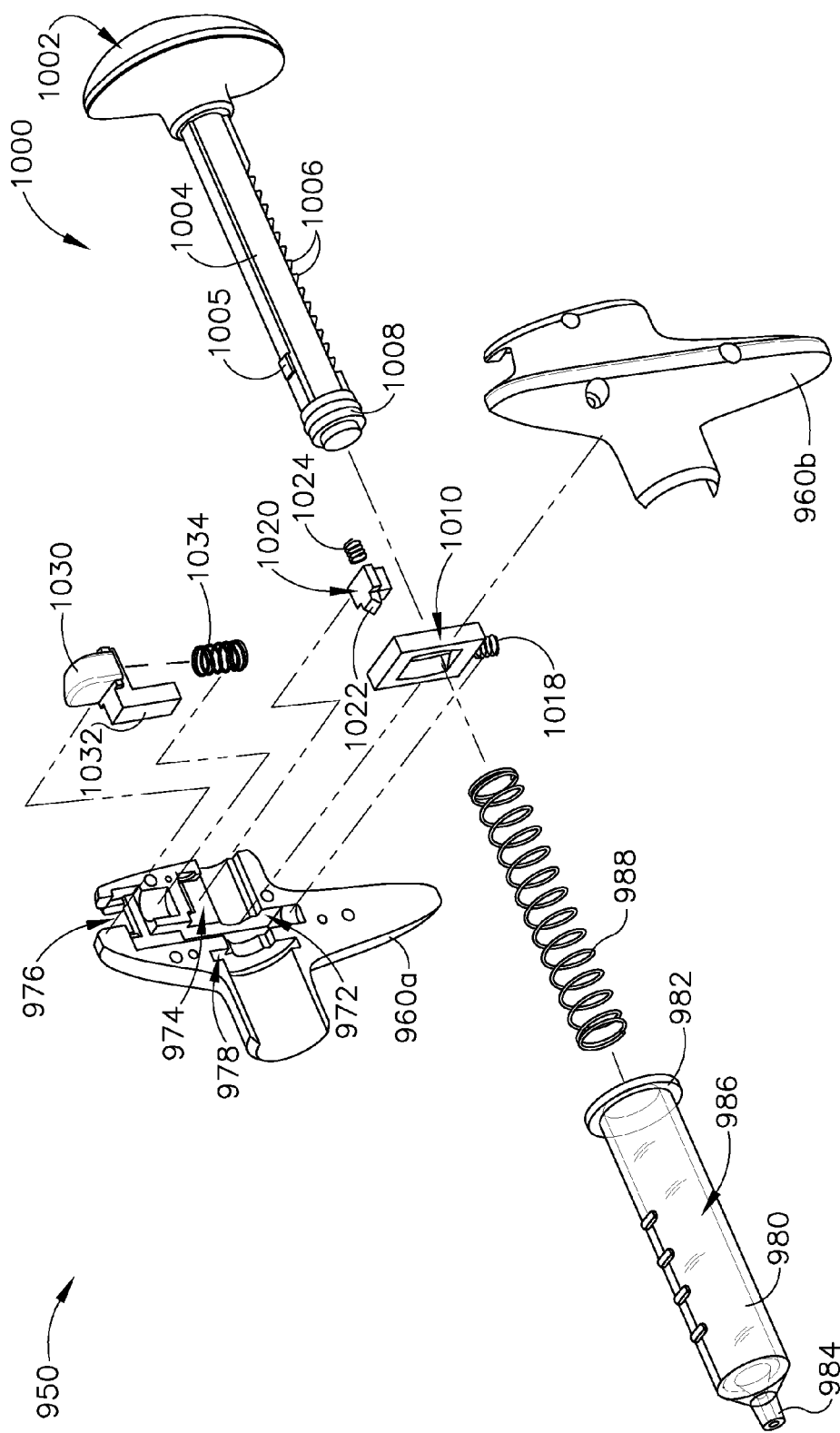
FIG. 22 depicts an exploded view of the inflator of FIG. 21.

As best seen in FIG. 22, each housing half (960a, 960b) defines a corresponding ratcheting block recess (972), a block latch recess (974), a pushbutton recess (976), and a flange recess (978). Ratcheting block recesses (972) cooperate to receive a ratcheting block (1010) and associated spring (1018). Spring (1018) biases ratcheting block (1010) upwardly within recess (972). Block latch recesses (974) cooperate to receive a block latch (1020) and associated spring (1024). Spring (1024) biases block latch (1020) distally within recess (974). Pushbutton recesses (976) cooperate to receive a pushbutton (1030) and associated spring (1034). Spring (1034) biases pushbutton (1030) upwardly within recess (972). While springs (1018, 1024, 1034) all comprise coil springs in the present example, it should be understood that any other suitable types of resilient components or features may be used. Flange recesses (978) cooperate to receive upper flange (982) of syringe barrel (980), thereby fixedly securing syringe barrel (980) to housing (960). Other suitable features and configurations for housing (960) will be apparent to those of ordinary skill in the art in view of the teachings herein.

FIG. 22 also shows additional features of plunger actuator (1000). In particular, plunger actuator (1000) of this example comprises a shaft (1004) extending distally from palm grip feature (1002), with a set of sawteeth (1006) on the underside of shaft (1004). Shaft (1004) also includes a latch engagement feature (1005) projecting from the upper side of shaft (1004). Latch engagement feature (1005) is configured to interact with latch (1020) as will be described in greater detail below. Shaft terminates in a piston (944), which is positioned within syringe barrel (980). Plunger actuator (1000) is operable to translate relative to housing (960), to thereby reciprocate piston (944) within syringe barrel (980). It should be understood that such reciprocation will selectively vary the volume of reservoir (986) in syringe barrel (980), to thereby draw fluid into or expel fluid from reservoir (986). As shown in FIGS. 22 and 24A-24E, a spring (988) is positioned inside reservoir (986), between the distal face of piston (1008) and the distal interior wall of reservoir (986), to bias plunger actuator (1000) proximally relative to syringe barrel (980). While spring (988) comprises a coil spring in the present example, any other suitable type of resilient member may be used. Furthermore, spring (988) may be positioned elsewhere in inflator (950).

Figure 23:
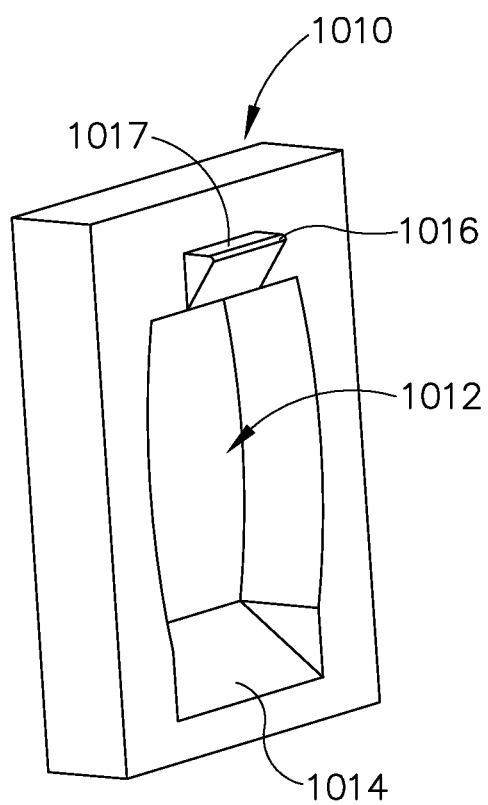
FIG. 23 depicts a perspective view of a ratchet block of the inflator of FIG. 21.

FIG. 23 shows the proximal side of ratcheting block (1010). As shown, ratcheting block (1010) defines an aperture (1012) that is sized and configured to receive shaft (1004) of plunger actuator (1000). A pawl feature (1014) is located at the bottom of aperture (1012) and is shaped to complement sawteeth (1006) of shaft (1004). A latch cam feature (1016) is located at the top of aperture (1012) and is shaped to complement a cam feature (1022) of block latch (1020). As will be described in greater detail below, ratcheting block (1010) is operable to permit plunger actuator (1000) to freely translate from a proximal position to a distal position; while preventing plunger actuator (1000) from retracting proximally when plunger actuator (1000) is released during translation from the proximal position to the distal position. As will also be described in greater detail below, block latch (1020) is configured to keep ratcheting block (1010) disengaged from plunger actuator (1000) after pushbutton (1030) is actuated, until plunger actuator (1000) reaches a proximal home position.

Figure 24A:
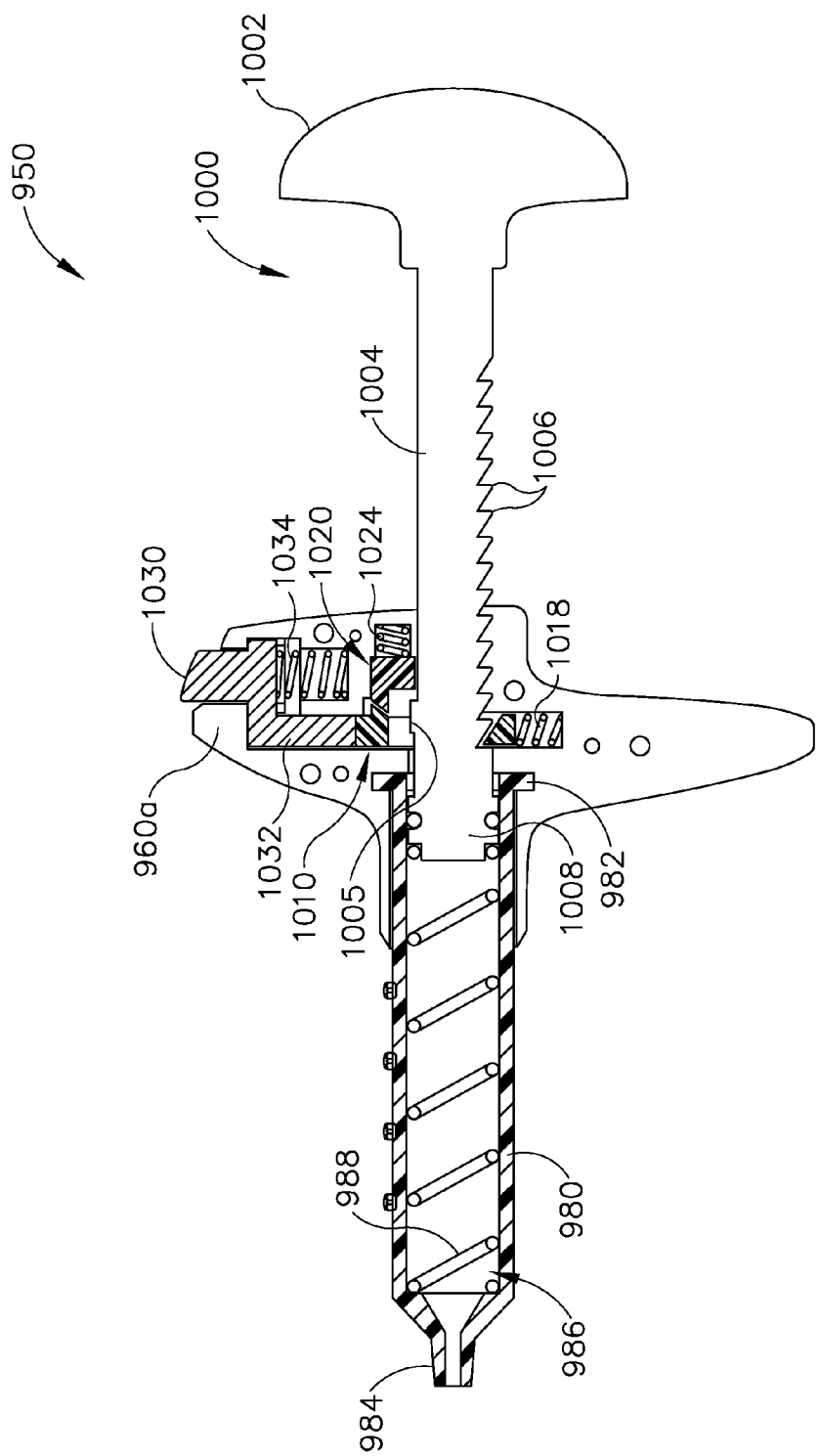
FIG. 24A depicts a cross-sectional side view of the inflator of FIG. 21, with the plunger in a proximal position.
Figure 24B:
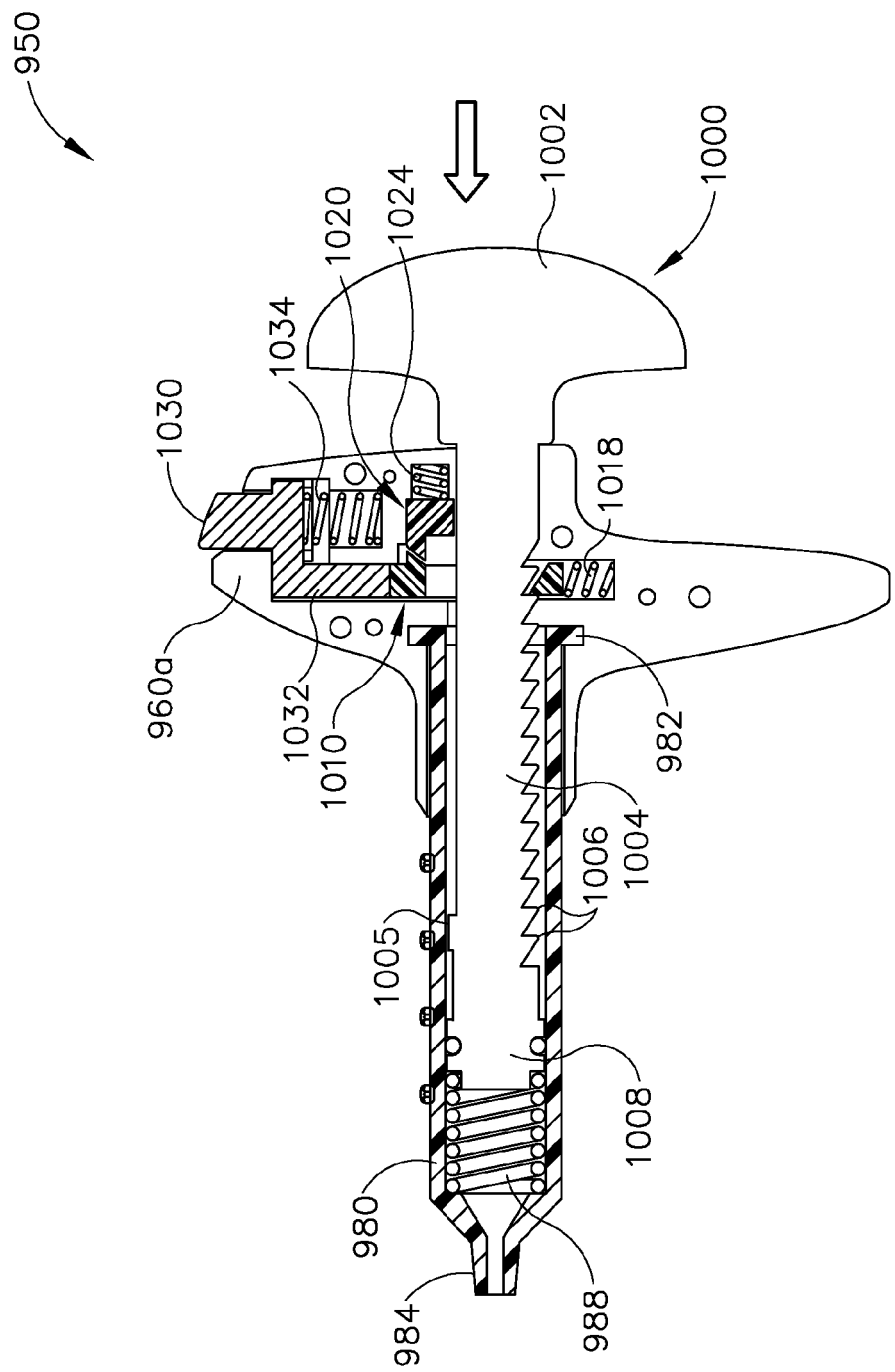
FIG. 24B depicts a cross-sectional side view of the inflator of FIG. 21, with the plunger in a distal position.

FIGS. 24A-24E depict a series showing interactions between the above-described components during operation of inflator (950). In particular, FIG. 24A shows plunger actuator (1000) in a proximal position. Ratcheting block (1010) is in an upper position and pushbutton (1030) is also in an upper position. Block latch (1020) is in a distal position. FIG. 24B shows plunger actuator (1000) advanced to a distal position. Ratcheting block (1010) remains in an upper position, pushbutton (1030) remains in an upper position, and block latch (1020) remains in a distal position. During the advancement of plunger actuator (1000) from the proximal position (FIG. 24A) to the distal position (FIG. 24B), pawl feature (1014) ratchets along sawteeth (1006) due to the resilient bias of spring (1018). If the operator were to relax their grip on grip features (962, 964, 1002) during advancement of plunger actuator (1000), engagement between pawl feature (1014) and sawteeth (1006) would prevent plunger actuator (1000) from moving proximally, despite the proximally directed bias from spring (988). Plunger actuator (1000) would thus maintain its longitudinal position relative to housing (960) and also maintain its position after reaching the stage shown in FIG. 24B, until the operator depresses pushbutton (1030).

Figure 24C:
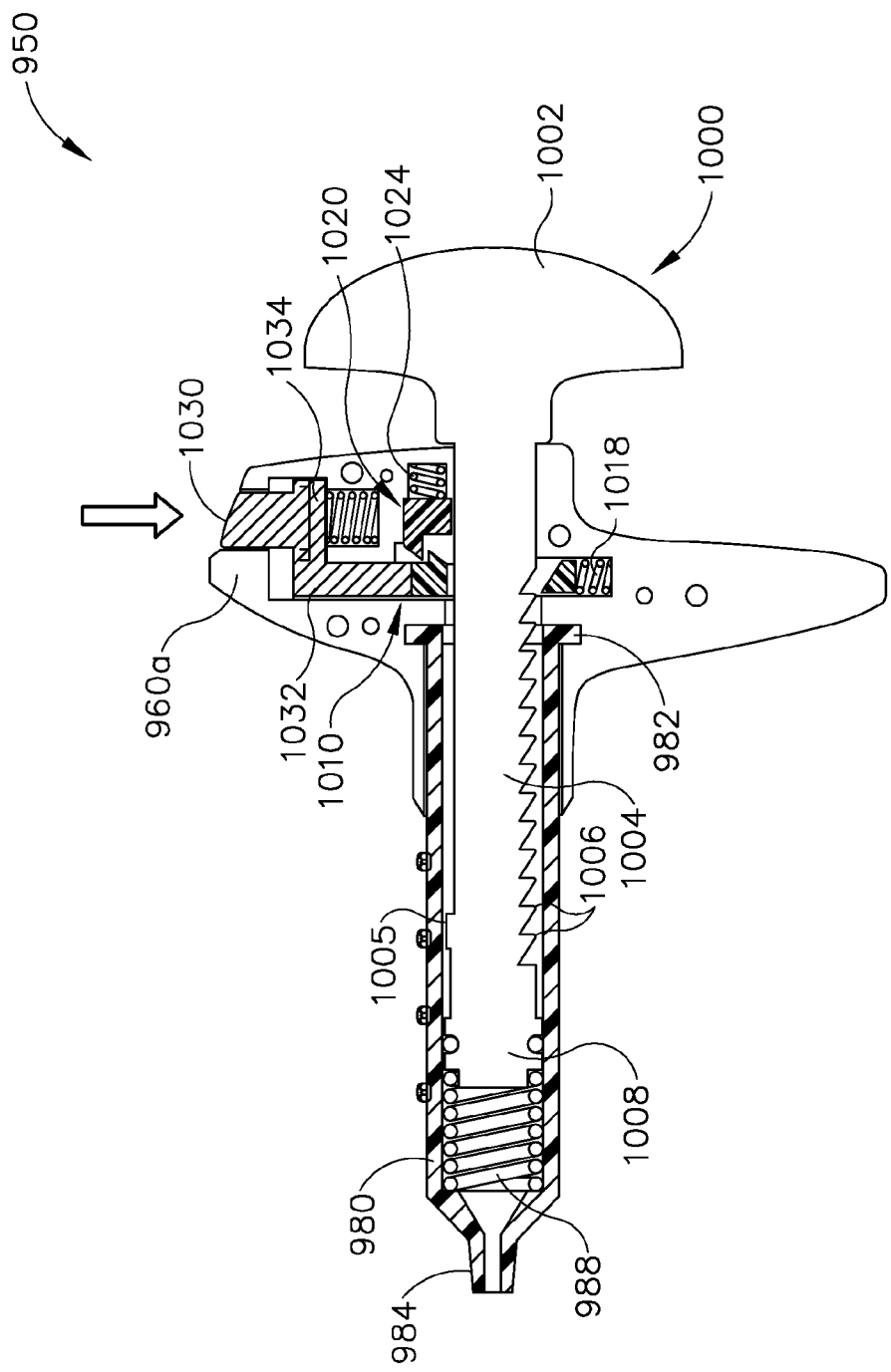
FIG. 24C depicts a cross-sectional side view of the inflator of FIG. 21, with the plunger in a distal position, and with a button actuated to release the ratchet block from the plunger driver.
Figure 24D:
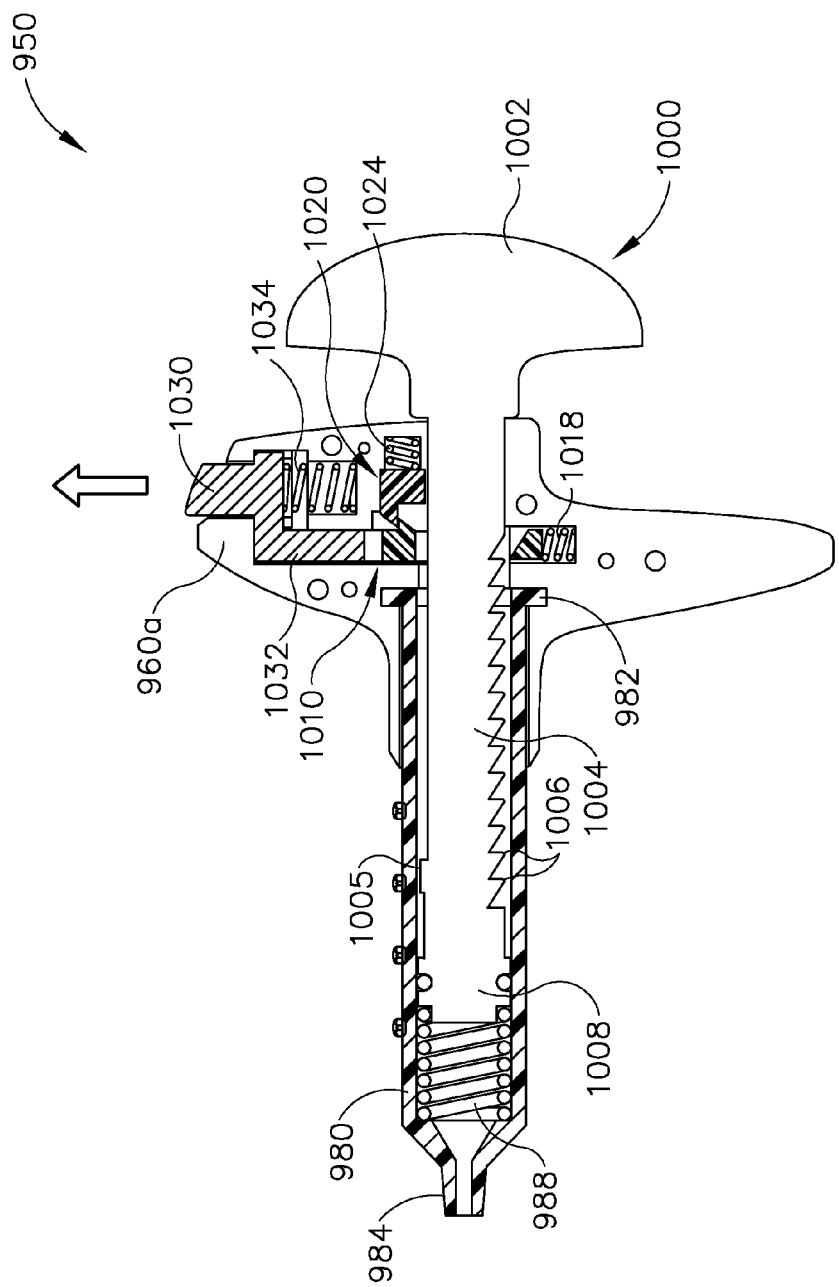
FIG. 24D depicts a cross-sectional side view of the inflator of FIG. 21, with the plunger in a distal position, with the button released, and with a latch holding the ratchet block in a position where the ratchet block remains disengaged from the plunger driver.

Pushbutton (1030) includes an integral, downwardly oriented projection (1032) that is operable to drive ratcheting block (1010) downwardly when pushbutton (1030) is pushed downwardly. As shown in FIG. 24C, the resulting downward movement of ratcheting block (1010) disengages pawl feature (1014) from sawteeth (1006). In addition, the downward movement of ratcheting block (1010) results in camming interaction between cam features (1016, 1022). This camming interaction drives block latch (1020) proximally until cam feature (1016) moves downwardly past cam feature (1022). As soon as cam feature (1016) passes cam feature (1022), spring (1024) drives block latch (1020) distally such that cam feature (1022) is positioned over an upper shelf (1017) of cam feature (1016). This resulting arrangement prevents ratcheting block (1010) from moving upwardly, such that block latch (1020) effectively locks ratcheting block (1010) in the downward position where pawl feature (1014) is disengaged from sawteeth (1006). This lock is maintained even after pushbutton (1030) is released as shown in FIG. 24D. It should be understood that, at this stage, the only thing maintaining the longitudinal position of plunger actuator (1000) relative to housing (960) is the operator's grip on grip features (962, 964, 1002).

Figure 24E:
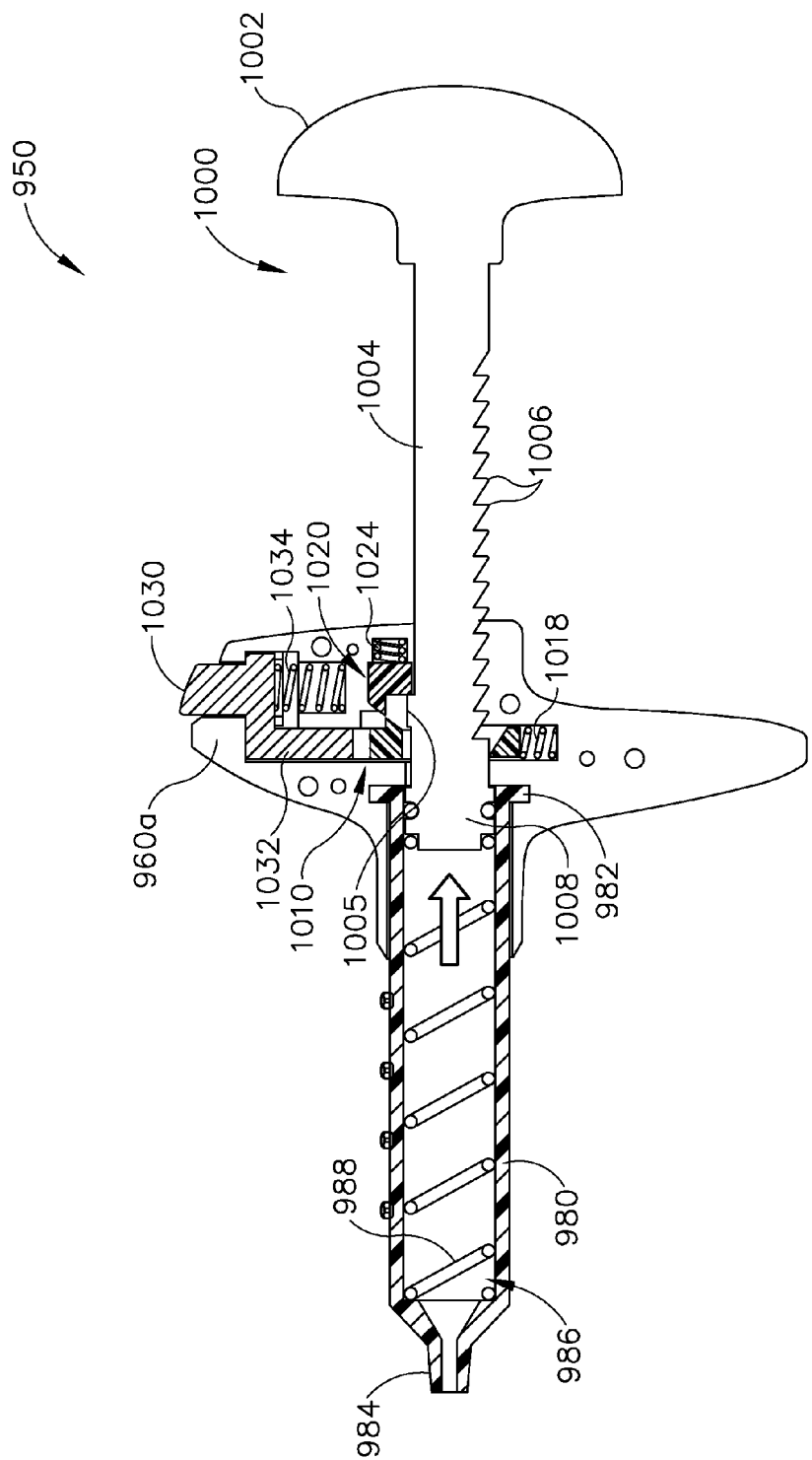
FIG. 24E depicts a cross-sectional side view of the inflator of FIG. 21, with the plunger in a proximal position, and with a latch disengagement feature of the plunger driver disengaging the latch from the ratchet block.
Figure 25:
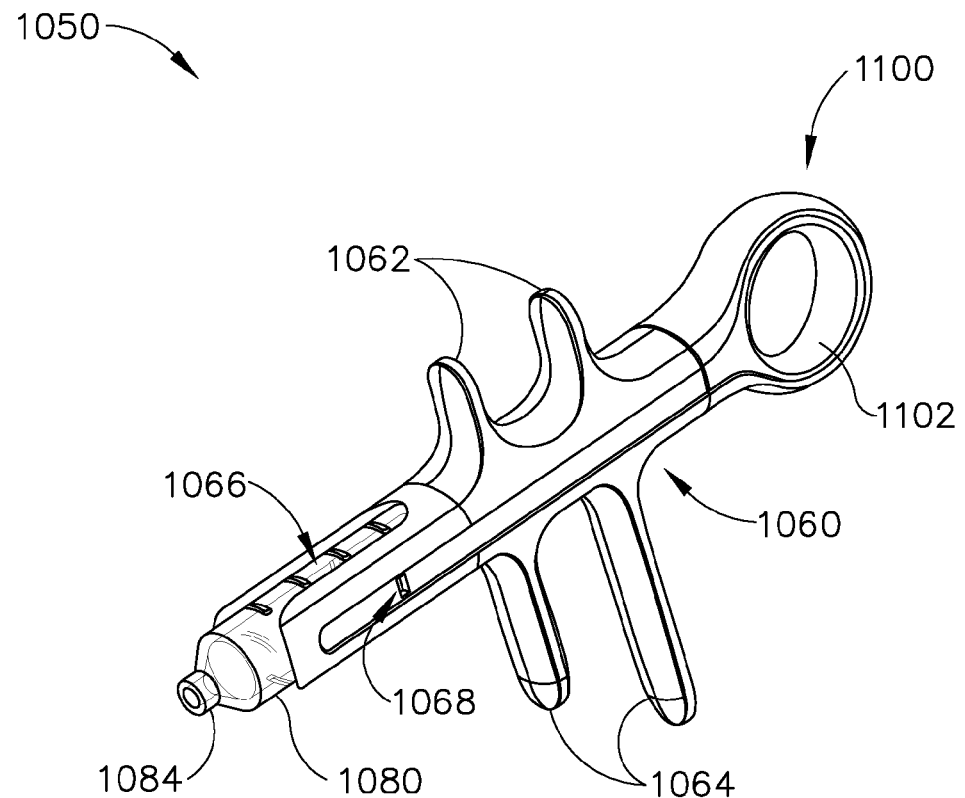
FIG. 25 depicts a perspective view of another exemplary inflator suited for use with the dilator catheter system of FIG. 1.
Figure 26:
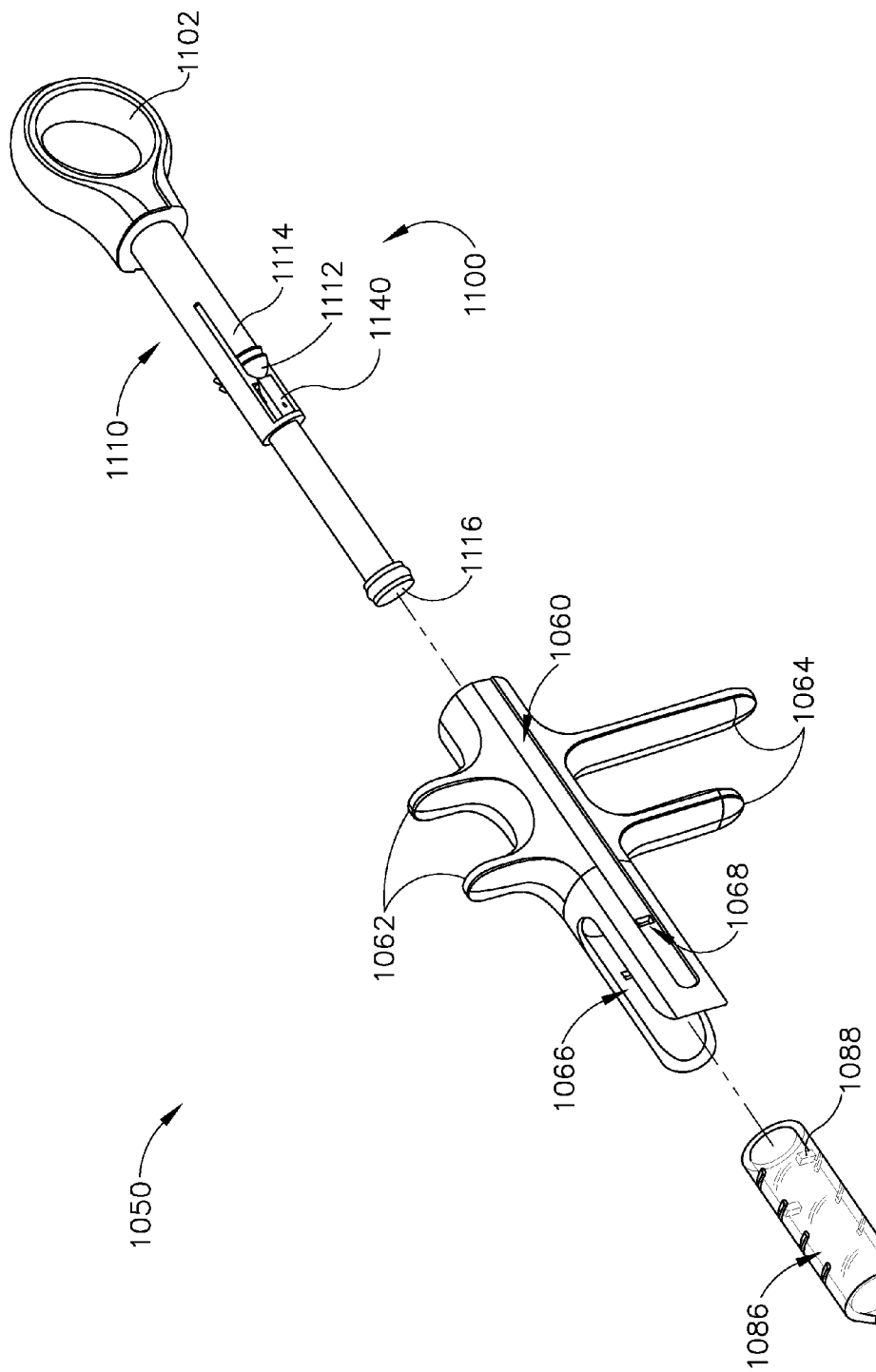
FIG. 26 depicts an exploded view of the inflator of FIG. 25.

When the operator relaxes their grip on grip features (962, 964, 1002), spring (988) drives plunger actuator (1000) proximally, as shown in the transition from FIG. 24D to FIG. 24E. Once plunger actuator (1000) reaches the proximal position shown in FIG. 24E, latch engagement feature (1005) drives block latch (1020) proximally, which disengages cam feature (1022) from upper shelf (1017) of cam feature (1016). This disengagement of cam feature (1016) enables spring (1018) to drive ratcheting block (1010) upwardly. In some versions, ratcheting block (1010) does not actually travel upwardly until the operator advances plunger actuator (1000) distally just enough to enable pawl feature (1014) to seat within a valley preceding the first sawtooth (1006), as shown in FIG. 24A. The above components may be configured such that block latch (1020) does not travel distally (under the influence of spring (1024)) enough to engage ratcheting block (1010) until ratcheting block has first traveled upwardly far enough for upper shelf (1017) to clear cam feature (1022). In other words, block latch (1020) does not impede upward movement of ratcheting block (1010) during the transition from the arrangement shown in FIG. 24E back to the arrangement shown in FIG. 24A.

In an exemplary use of inflator (950), a operator may start with plunger actuator (1000) advanced to a distal position as shown in FIG. 24B. The operator may then position port (984) in a bowl or other container of saline to draw fluid from. In instances where port (984) is coupled with one end of flexible tube (46), the operator may position the other end of flexible tube (46) in the saline. In either case, the operator may then depress pushbutton (1030) to disengage ratcheting block (1010) from shaft (1040) as shown in FIG. 24C. While maintaining a grip on grip features (962, 964, 1002), the operator may release pushbutton (1030) as shown in FIG. 24D. Next, the operator may relax their grip on grip features (962, 964, 1002), allowing spring (988) to drive plunger actuator (1000) proximally toward the position shown in FIG. 24E. This will in turn translate piston (1008) proximally within syringe barrel (980), thereby drawing the saline (or other fluid) into reservoir (986). The operator may then remove port (984) or flexible tube (46) from the saline container.

At this stage, the operator may advance plunger actuator (1000) distally in order to purge air from reservoir (986). For instance, the operator may orient inflator (950) such that port (984) is positioned upwardly to gather air at the top of reservoir (986) before squeezing on grip features (962, 964, 1002) to advance plunger actuator (1000) distally in order to purge air from reservoir (986). As the operator advances plunger actuator (1000) distally, pawl feature (1014) will ratchet along sawteeth (1006) to prevent plunger actuator (1000) from retracting proximally if and when the operator relaxes their grip on grip features (962, 964, 1002).

Once reservoir (986) has been sufficiently filled with fluid and air has been purged, the operator may couple inflator (950) with dilation catheter (20), such as by coupling port (984) with lateral port (26) via a flexible tube (46). In some instances, a conventional fluid pressure gauge (not shown) may be coupled in the fluid path between port (984) and lateral port (26) (e.g., via a "T" fitting, etc.). Of course, inflator (950) may alternatively include an integral pressure gauge. With dilator (22) being suitably positioned within an anatomical passageway (e.g., an ostium (O), etc.), the operator may then advance plunger actuator (1000) distally relative to housing (960) to advance piston (1008) within syringe barrel (980), thereby transferring fluid from reservoir (986) to dilator (22). The operator may observe the pressure reading at the pressure gauge while advancing plunger actuator (1000) distally in order to determine when the appropriate fluid pressure level has been reached. Again, pawl feature (1014) will ratchet along sawteeth (1006) as the operator advances plunger actuator (1000) distally, to prevent plunger actuator (1000) from retracting proximally if and when the operator relaxes their grip on grip features (962, 964, 1002).

Once the operator has attained the desired level of pressure in dilator (22) within the anatomical passageway to dilate the anatomical passageway, the operator may pause for an approximate, predetermined period of time (e.g., approximately three seconds, etc.). The operator may then depress pushbutton (1030) to once again disengage ratcheting block (1010) from sawteeth (1006), then relax their grip on grip features (962, 964, 1002). This will allow spring (988) to drive plunger actuator (1000) proximally, thereby drawing fluid from dilator (22) back into reservoir (986). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (986) may be used repeatedly to dilate a plurality of anatomical passageways, without having to withdraw dilator (22) from the patient, and without having to decouple inflator (950) from the rest of dilator catheter system (10), until all of the desired dilations have been completed. Other suitable variations of inflator (950) will be apparent to those of ordinary skill in the art in view of the teachings herein. Similarly, other suitable ways in which inflator (950) may be used will be apparent to those of ordinary skill in the art in view of the teachings herein.

J. Exemplary Alternative Inflator with Ratcheting Drive and Thumb Ring Release

FIGS. 25-28C depict another exemplary inflator (1050). Inflator (1050) of this example includes a housing (1060), a syringe barrel (1080), and a plunger actuator assembly (1100). Housing (1060) of this example is formed as a single piece that defines a pair of upper finger grip features (1062) and a pair of lower finger grip features (1064). During use of inflator (1050), a operator may place their index finger between the upper grip features (1062) and their other three fingers between the lower grip features (1064). The proximal end of plunger actuator assembly (1100) defines a thumb ring (1102). Grip features (1062, 1064) and thumb ring (1102) are configured to enable a operator to grasp and manipulate inflator (1050) with a single hand by engaging their fingers with finger grip features (1062, 1064) and inserting their thumb of the same hand through thumb ring (1102). As will be described in greater detail below, inflator (1050) may be selectively actuated by the operator advancing their thumb distally to drive plunger actuator assembly (1100) distally relative to housing (1060); or by retracting their thumb proximally to pull plunger actuator assembly (1100) proximally relative to housing (1060).

Figure 27:
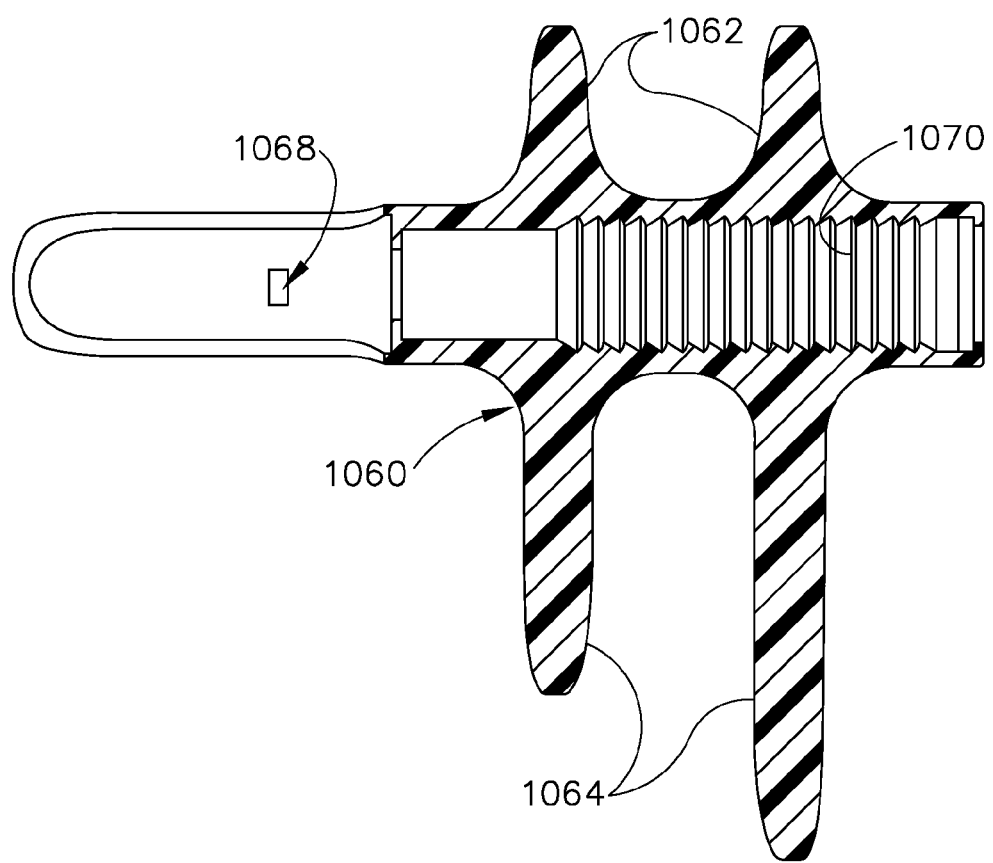
FIG. 27 depicts a cross-sectional side view of the housing of the inflator of FIG. 25.

As best seen in FIGS. 25-28, housing (1060) of the present example defines a pair of notches (1068) that are configured to receive complementary tabs (1088) of syringe barrel (1080) to provide a secure snap-fit engagement between housing (1060) and syringe barrel (1080). Housing (1060) also defines a syringe barrel viewing recess (1066) that permits visualization of the amount of fluid within syringe barrel (1080) during use of inflator (1050). As best seen in FIG. 27, the interior of housing (1060) includes a longitudinal array of annular interior ribs (1070). Ribs (1070) each have a sawtooth profile. Other suitable features and configurations for housing (1060) will be apparent to those of ordinary skill in the art in view of the teachings herein.

Figure 28:
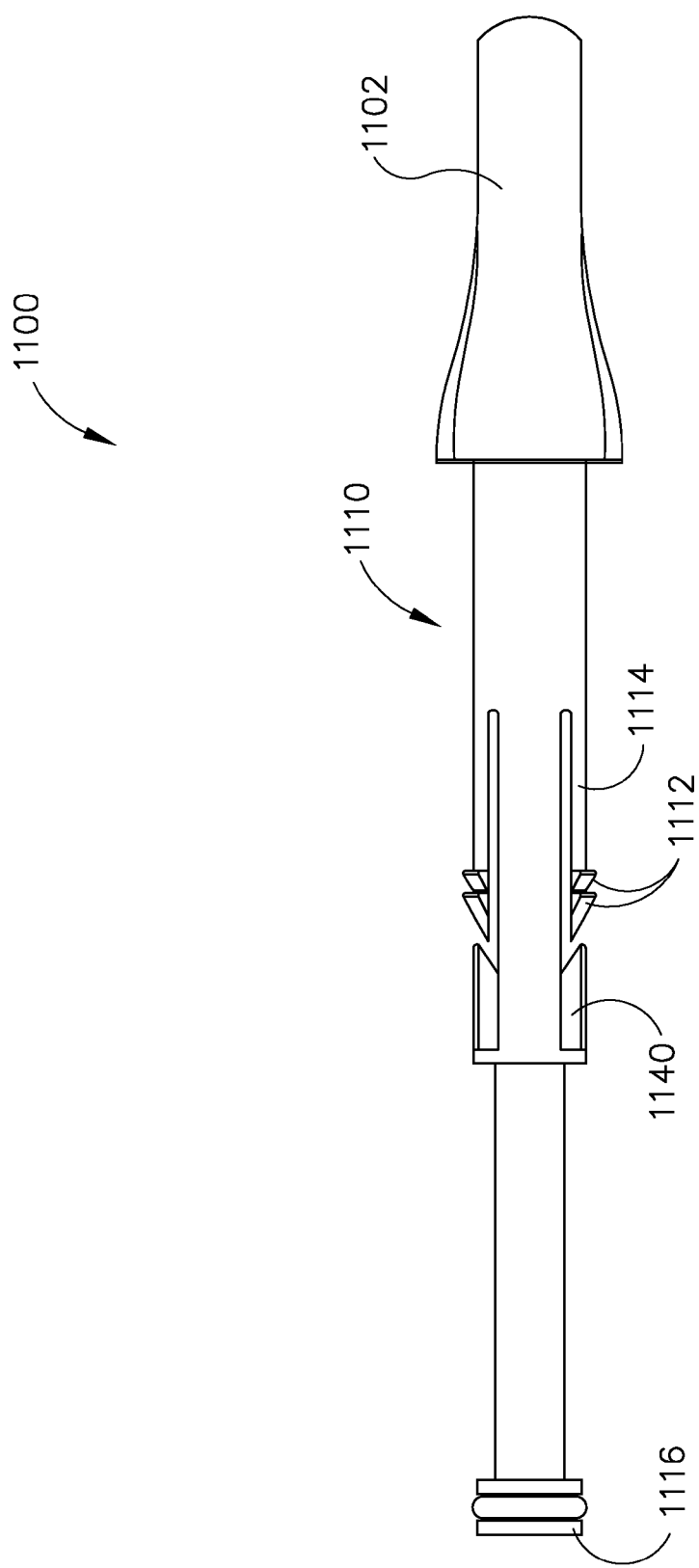
FIG. 28 depicts a top plan view of the plunger actuation assembly of the inflator of FIG. 25.
Figure 29:
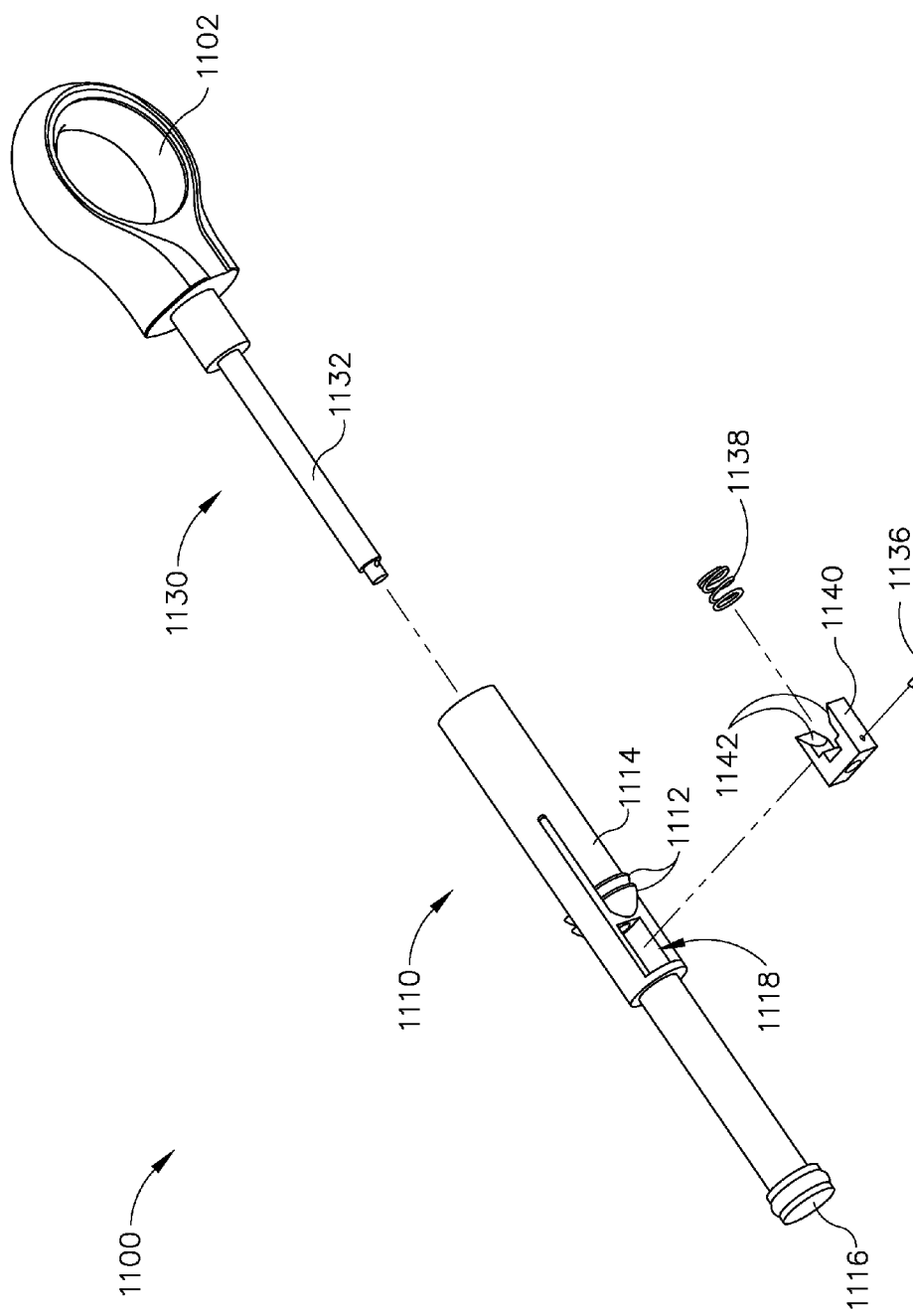
FIG. 29 depicts an exploded view of the plunger actuation assembly of FIG. 28.

As best seen in FIGS. 28-29, plunger actuator assembly (1100) of the present example comprises a plunger driver (1110) and a cam driver (1130). Plunger driver includes a pair of lateral ratchet features (1112) positioned at the distal ends of respective resilient arms (1114). Resilient arms (1114) extend parallel to the longitudinal axis defined by plunger driver (1110), yet are capable of deflecting inwardly toward the longitudinal axis defined by plunger driver (1110) as will be described in greater detail below. The distal end of plunger driver (1110) includes a piston (1116), which is positioned within syringe barrel (1080). Plunger actuator assembly (1100) is operable to translate relative to housing (1060), to thereby reciprocate piston (1116) within syringe barrel (1080). It should be understood that such reciprocation will selectively vary the volume of reservoir (1086) in syringe barrel (1080), to thereby draw fluid into or expel fluid from reservoir (1086).

Cam driver (1130) includes a rod (1132) that is integral with thumb ring (1102). Rod (1132) is slidably disposed within a bore in plunger driver (1110), such that cam driver (1130) and plunger driver (1110) are coaxially aligned. A cam feature (1140) is secured to the distal end of rod (1132) by a pin (1136). Cam feature (1140) is positioned within a transverse channel (1118) of plunger driver (1110) and projects laterally from channel (1118). Cam feature (1140) includes a pair of proximally presented cam surfaces (1142) that are positioned to selectively engage of lateral ratchet features (1112) of plunger driver (1110) as will be described in greater detail below. A spring (1138) is positioned about rod (1132) and is configured to bias cam driver (1130) distally relative to plunger driver (1110). While spring (1138) comprises a coil spring in the present example, any other suitable type of resilient member may be used. Furthermore, spring (1138) may be positioned elsewhere in inflator (1050).

Figure 30A:
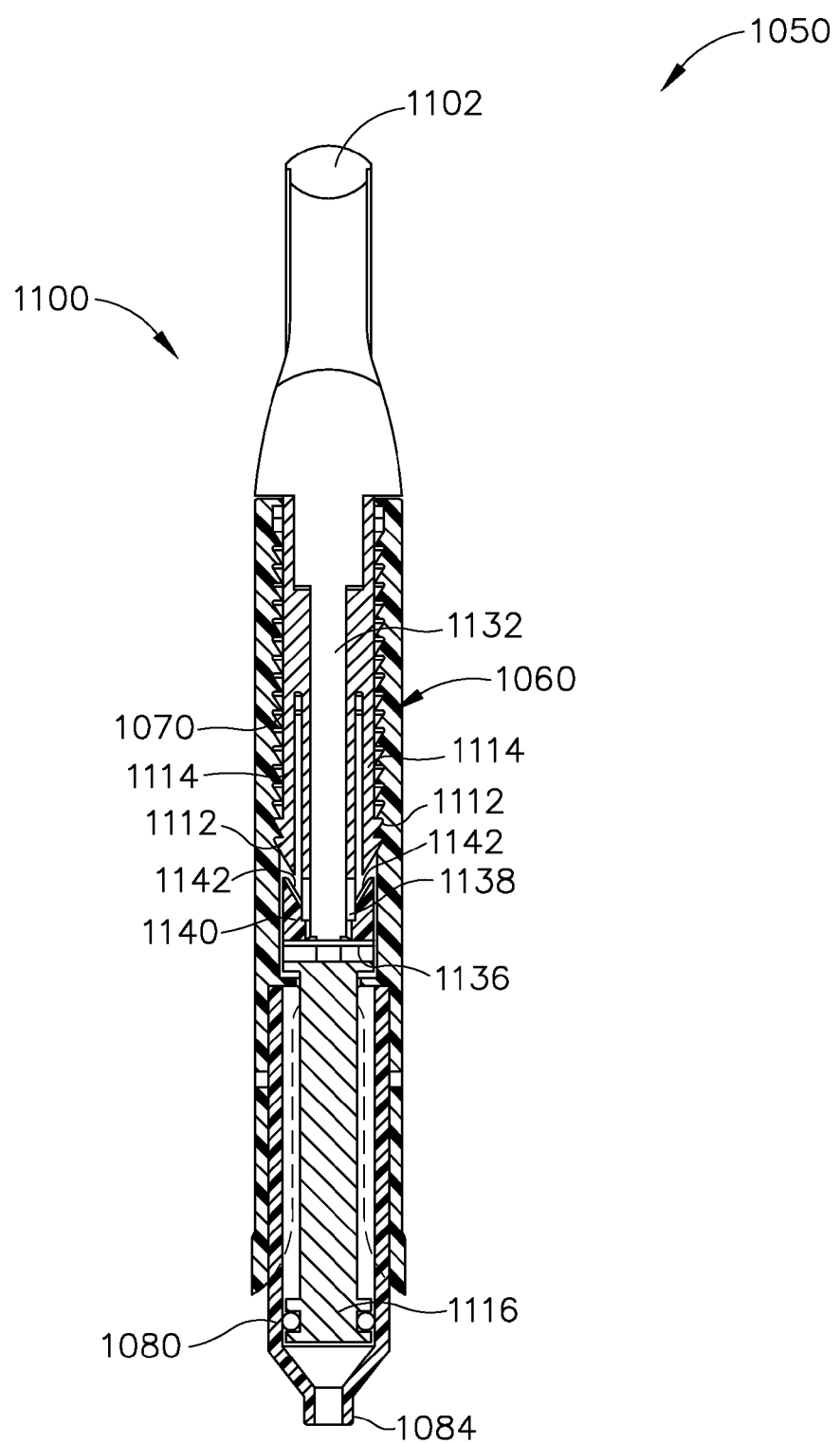
FIG. 30A depicts a cross-sectional top view of the inflator of FIG. 25, with the plunger in a distal position and with the plunger actuation assembly in a locked configuration.
Figure 30B:
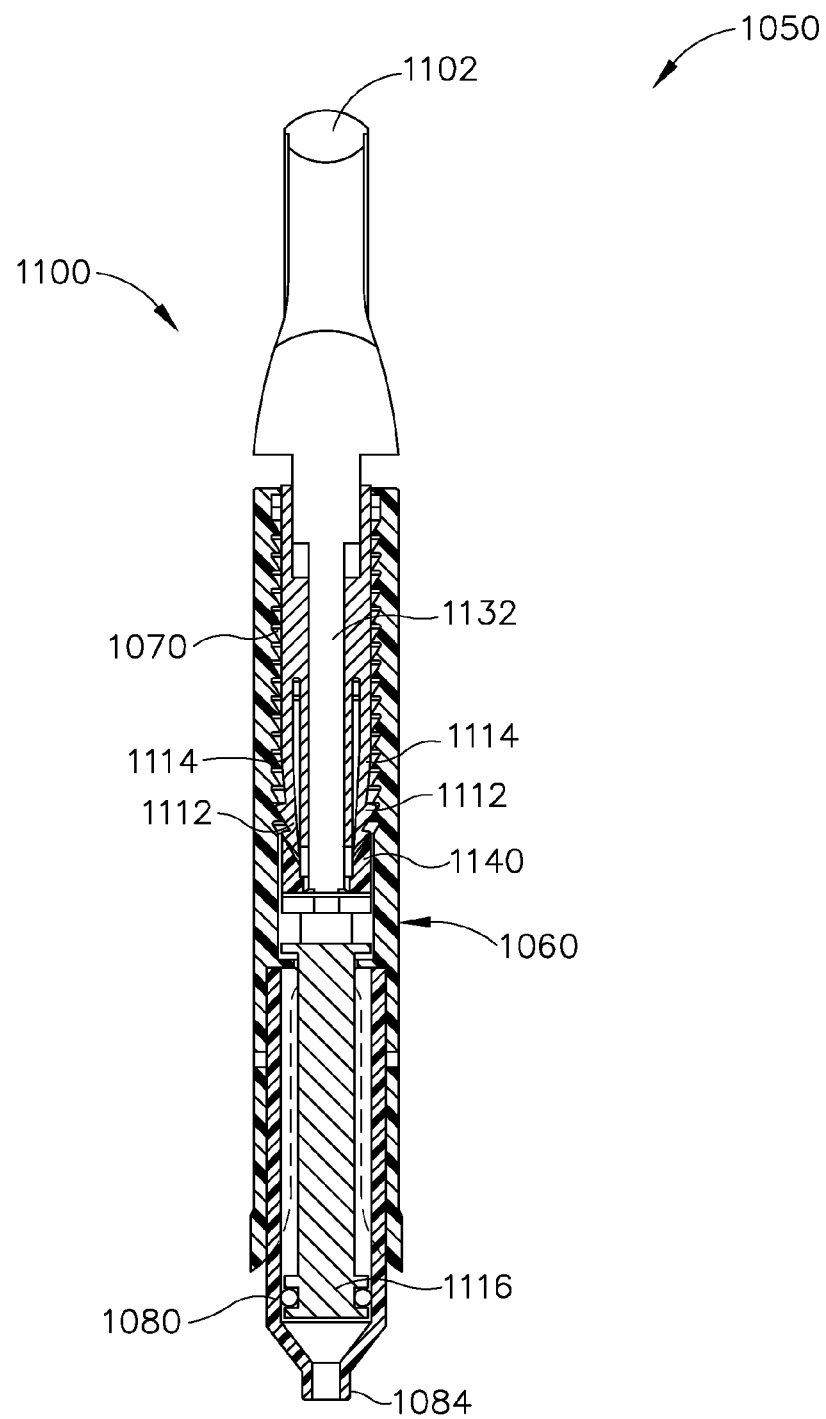
FIG. 30B depicts a cross-sectional top view of the inflator of FIG. 25, with the plunger in a distal position and with the plunger actuation assembly in an unlocked configuration.
Figure 30C:
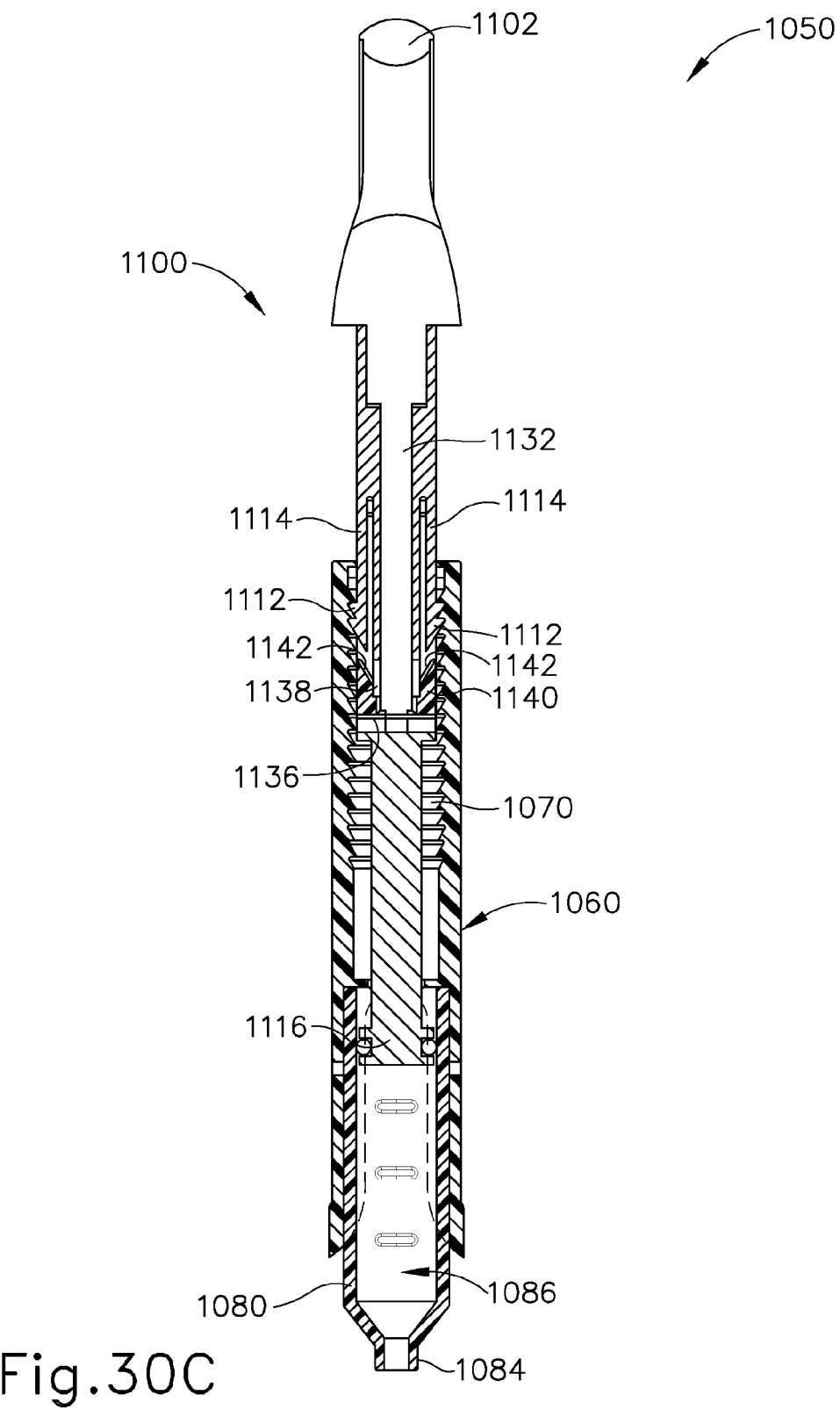
FIG. 30C depicts a cross-sectional top view of the inflator of FIG. 25, with the plunger in a proximal position and with the plunger actuation assembly in a locked configuration.

FIGS. 30A-30C depict a series showing interactions between the above-described components during operation of inflator (1050). In particular, FIG. 30A shows plunger actuation assembly (1100) in a distal position. Lateral ratchet features (1112) are engaged with ribs (1070) of housing (1060), preventing plunger driver (1110) from translating proximally relative to housing (1060). When the operator pulls proximally on thumb ring (1102), this translates cam driver (1130) proximally relative to plunger driver (1100), which remains longitudinally fixed relative to housing (1060). As shown in FIG. 30B, this retraction of cam driver (1130) drives cam feature (1140) into lateral ratchet features (1112). Cam surfaces (1142) drive lateral ratchet features (1112) inwardly, causing arms (1114) to bend. This disengages ratchet features (1112) from ribs (1070). With ratchet features (1112) disengaged from ribs (1070), plunger driver (1110) is free to translate proximally relative to housing (1060) as the operator continues to pull proximally on thumb ring (1102). Once plunger driver (1110) reaches a proximal position as shown in FIG. 30C, the operator may substantially release thumb ring (1102). This will enable spring (1138) to drive cam driver (1130) distally relative to plunger driver (1110). With cam driver (1130) driven distally relative to plunger driver (1110), cam feature (1140) disengages ratchet features (1112), which deflect back outwardly under the resilient bias of arms (1114). The outwardly deflected ratchet features (1112) once again engage ribs (1070). As plunger actuator assembly (1100) is thereafter advanced distally relative to housing (1060), ratchet features (1112) ratchet along ribs (1070) and prevent plunger driver (1110) from translating proximally when thumb ring (1102) is released.

In an exemplary use of inflator (1050), a operator may start with plunger actuator assembly (1100) advanced to a distal position as shown in FIG. 30A. The operator may then position port (1084) of syringe barrel (1080) in a bowl or other container of saline to draw fluid from. In instances where port (1084) is coupled with one end of flexible tube (46), the operator may position the other end of flexible tube (46) in the saline. In either case, the operator may then pull thumb ring (1102) proximally to drive cam feature (1140) proximally, to thereby disengage ratchet features (1112) from ribs (1070) as shown in FIG. 30B. The operator may continue to pull thumb ring (1102) proximally to retract plunger actuation assembly (1100) proximally toward the position shown in FIG. 30C. This will in turn translate piston (1116) proximally within syringe barrel (1080), thereby drawing the saline (or other fluid) into reservoir (1086). The operator may then remove port (1084) or flexible tube (46) from the saline container.

At this stage, the operator may advance plunger actuator assembly (1100) distally in order to purge air from reservoir (1086). For instance, the operator may orient inflator (1050) such that port (1084) is positioned upwardly to gather air at the top of reservoir (1086) before pushing thumb ring (1102) distally to advance plunger actuator assembly (1100) distally in order to purge air from reservoir (1086). As the operator advances plunger actuator assembly (1100) distally, ratchet features (1112) will ratchet along ribs (1070) to prevent plunger actuator (1000) from retracting proximally if and when the operator releases thumb ring (1102).

Once reservoir (1086) has been sufficiently filled with fluid and air has been purged, the operator may couple inflator (1050) with dilation catheter (20), such as by coupling port (1084) with lateral port (26) via a flexible tube (46). In some instances, a conventional fluid pressure gauge (not shown) may be coupled in the fluid path between port (1084) and lateral port (26) (e.g., via a "T" fitting, etc.). Of course, inflator (1050) may alternatively include an integral pressure gauge. With dilator (22) being suitably positioned within an anatomical passageway (e.g., an ostium (O), etc.), the operator may then advance plunger actuator assembly (1100) distally relative to housing (1060) to advance piston (1116) within syringe barrel (1080), thereby transferring fluid from reservoir (1086) to dilator (22). The operator may observe the pressure reading at the pressure gauge while advancing plunger actuator assembly (1100) distally in order to determine when the appropriate fluid pressure level has been reached. Again, ratchet features (1112) will ratchet along ribs (1070) as the operator advances plunger actuator assembly (1100) distally, to prevent plunger actuator assembly (1100) from retracting proximally if and when the operator releases thumb ring (1102).

Once the operator has attained the desired level of pressure in dilator (22) within the anatomical passageway to dilate the anatomical passageway, the operator may pause for an approximate, predetermined period of time (e.g., approximately three seconds, etc.). The operator may then pull thumb ring (1102) proximally to drive cam feature (1140) proximally, to thereby disengage ratchet features (1112) from ribs (1070). This will allow plunger driver (1110) to translate proximally relative to housing (1060). The operator may continue to pull thumb ring (1102) proximally to retract plunger actuation assembly (1100) proximally toward the position shown in FIG. 30C. This will in turn translate piston (1116) proximally within syringe barrel (1080), thereby drawing the saline (or other fluid) from dilator (22) back into reservoir (1086). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (1086) may be used repeatedly to dilate a plurality of anatomical passageways, without having to withdraw dilator (22) from the patient, and without having to decouple inflator (1050) from the rest of dilator catheter system (10), until all of the desired dilations have been completed. Other suitable variations of inflator (1050) will be apparent to those of ordinary skill in the art in view of the teachings herein. Similarly, other suitable ways in which inflator (1050) may be used will be apparent to those of ordinary skill in the art in view of the teachings herein.

Figure 31:
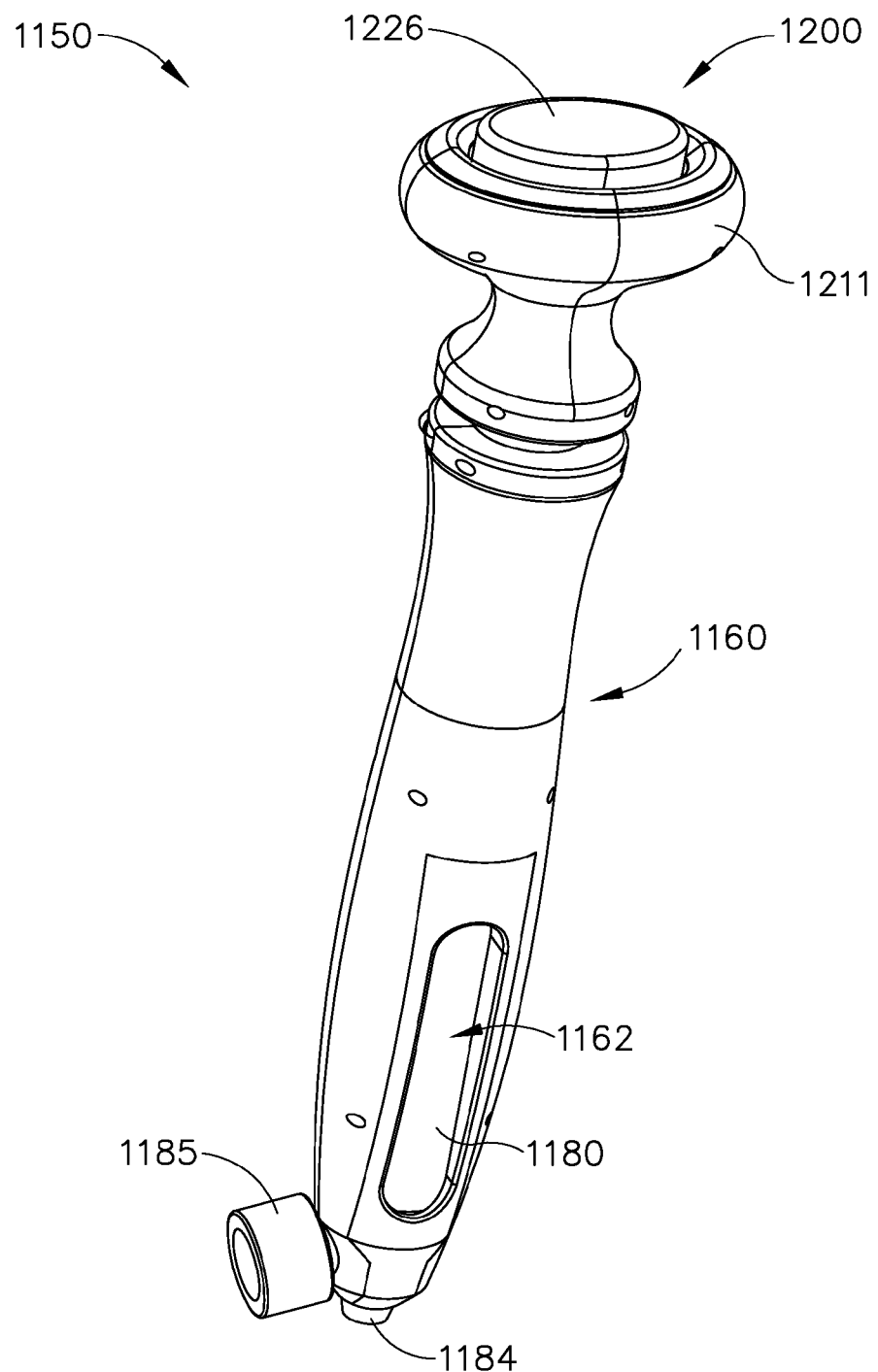
FIG. 31 depicts a perspective view of another exemplary inflator suited for use with the dilator catheter system of FIG. 1.
Figure 32:
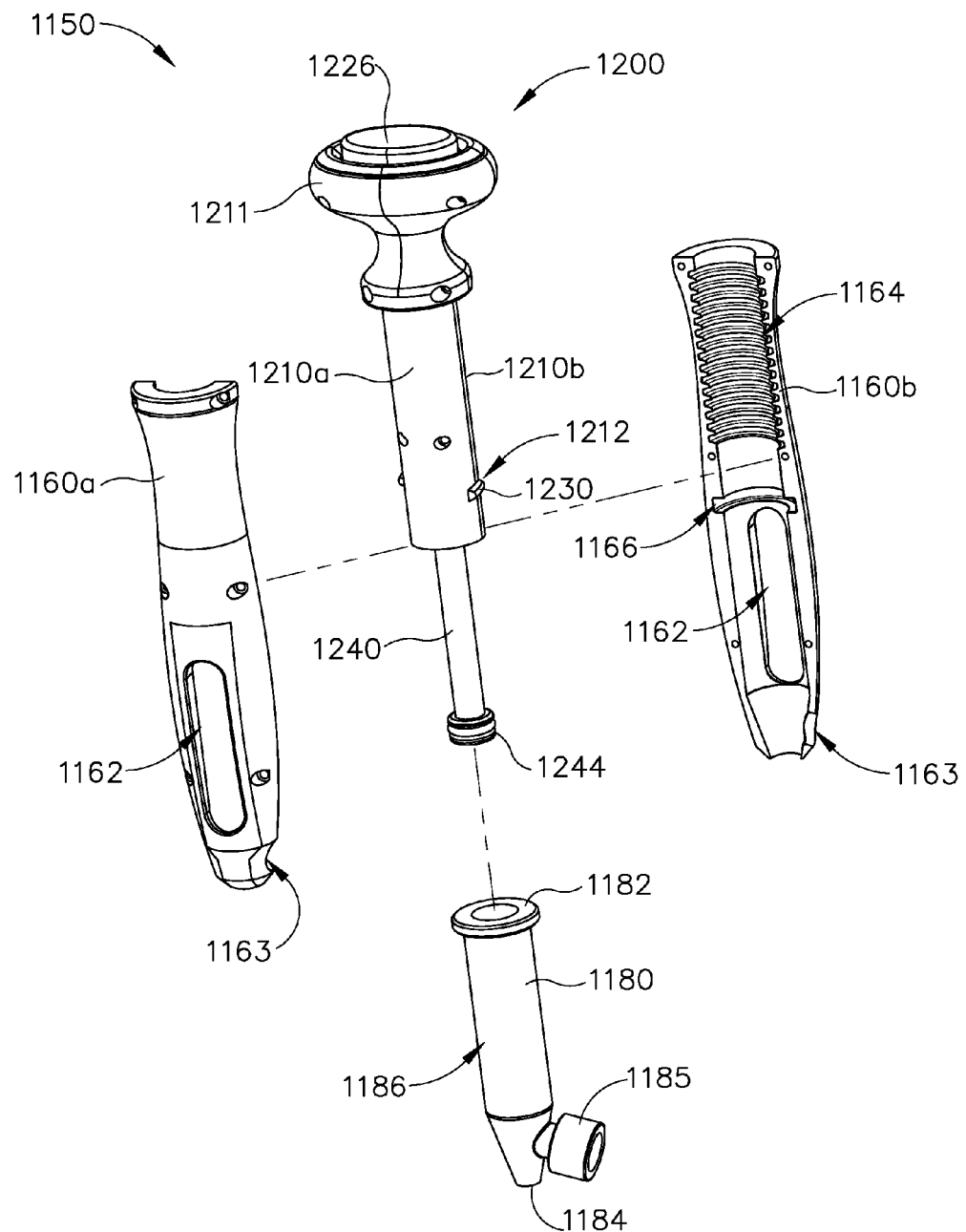
FIG. 32 depicts an exploded view of the inflator of FIG. 31.
Figure 33:
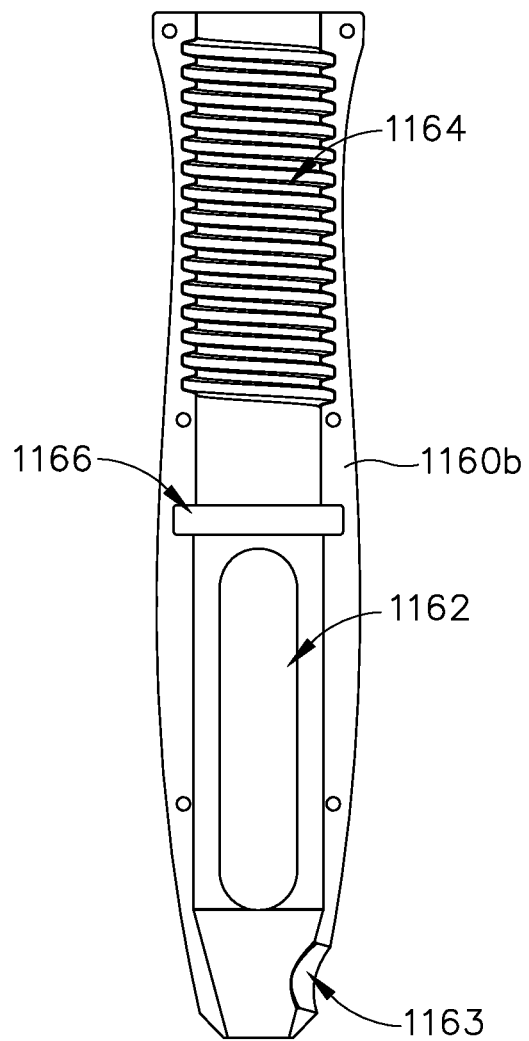
FIG. 33 depicts a side elevational view of a housing half of the inflator of FIG. 31.

K. Exemplary Alternative Inflator with Rotary Drive and Button Release of Sliding Locking Features FIGS. 31-37C depict another exemplary inflator (1150). Inflator (1150) of this example includes a housing (1160), a syringe barrel (1180), and a plunger actuation assembly (1200). Housing (1160) is formed by two halves (1160a, 1160b) that are joined together to contain syringe barrel (1180) and plunger actuation assembly (1200). As best seen in FIGS. 31-33, each half (1160a, 1160b) includes a window (1162) that permits viewing of syringe barrel (1180). In particular, a operator of inflator (1150) may see how much fluid is in syringe barrel (1180) by viewing syringe barrel (1180) through window (1162).

As best seen in FIG. 33, each half (1160a, 1160b) also includes a respective helically oriented groove (1164) and flange recess (1166). Grooves (1164) of halves (1160a, 1160b) are configured to align with each other when halves (1160a, 1160b) are joined, to form a continuous helical thread in housing (1160). Flange recesses (1166) of halves (1160a, 1160b) are configured to align with each other when halves (1160a, 1160b) are joined, to capture and retain the upper flange (1182) of syringe barrel (1180). The distal port (1184) of syringe barrel (1180) protrudes distally from housing (1160). Distal port (1184) is configured to communicate fluid to and from the reservoir (1186) defined by syringe barrel (1180). Each housing half (1160a, 1160b) also includes a respective lateral notch (1163). When halves (1160a, 1160b) are assembled together, notches (1163) together provide clearance for a laterally protruding portion of a pressure gauge (1185), which is an integral feature of syringe barrel (1180) in this example. Pressure gauge (1185) may be configured and operable like any other pressure gauge (162, 262, 362, 462, 472, 482, 562, 662, 762) described herein; or may be configured and operable in any other suitable fashion. Alternatively, pressure gauge (1185) and notches (1163) may simply be omitted if desired.

Figure 34:
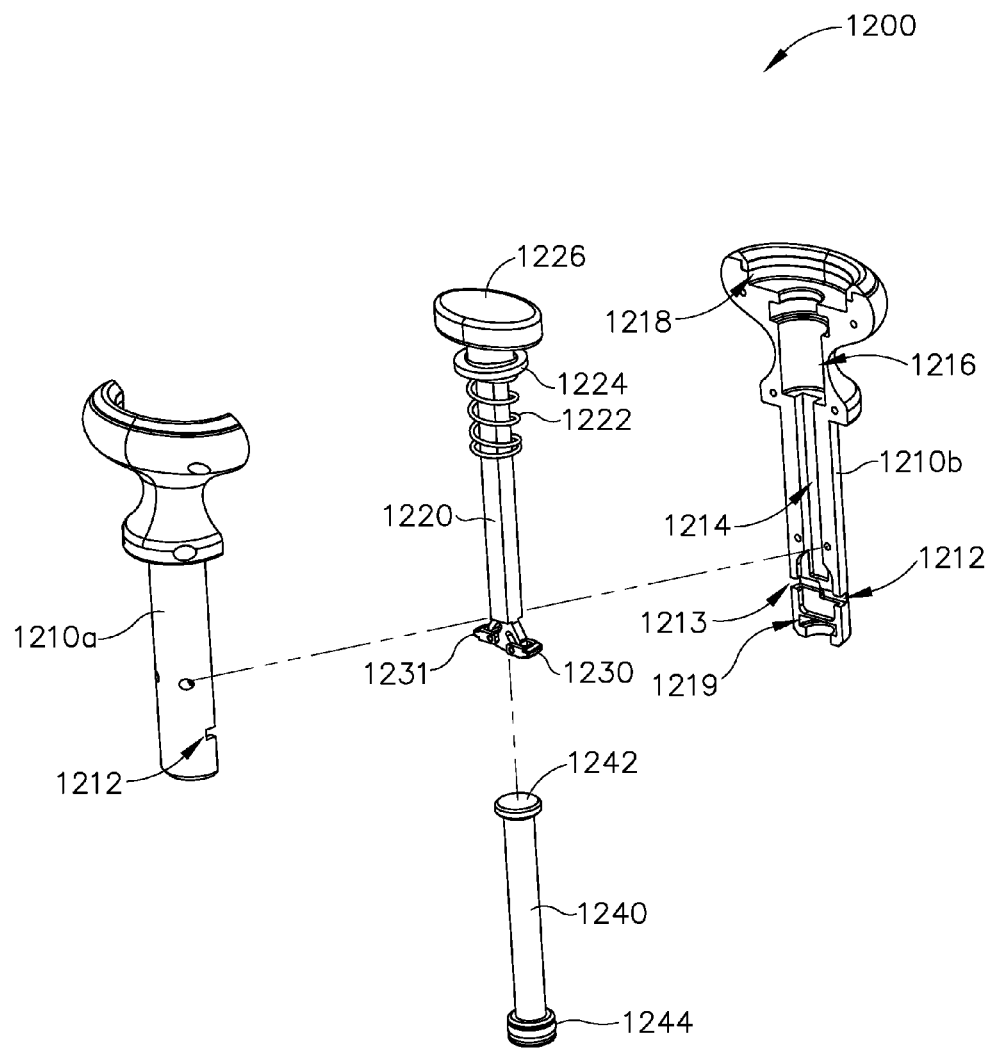
FIG. 34 depicts an exploded view of a plunger actuation assembly of the inflator of FIG. 31.
Figure 35:
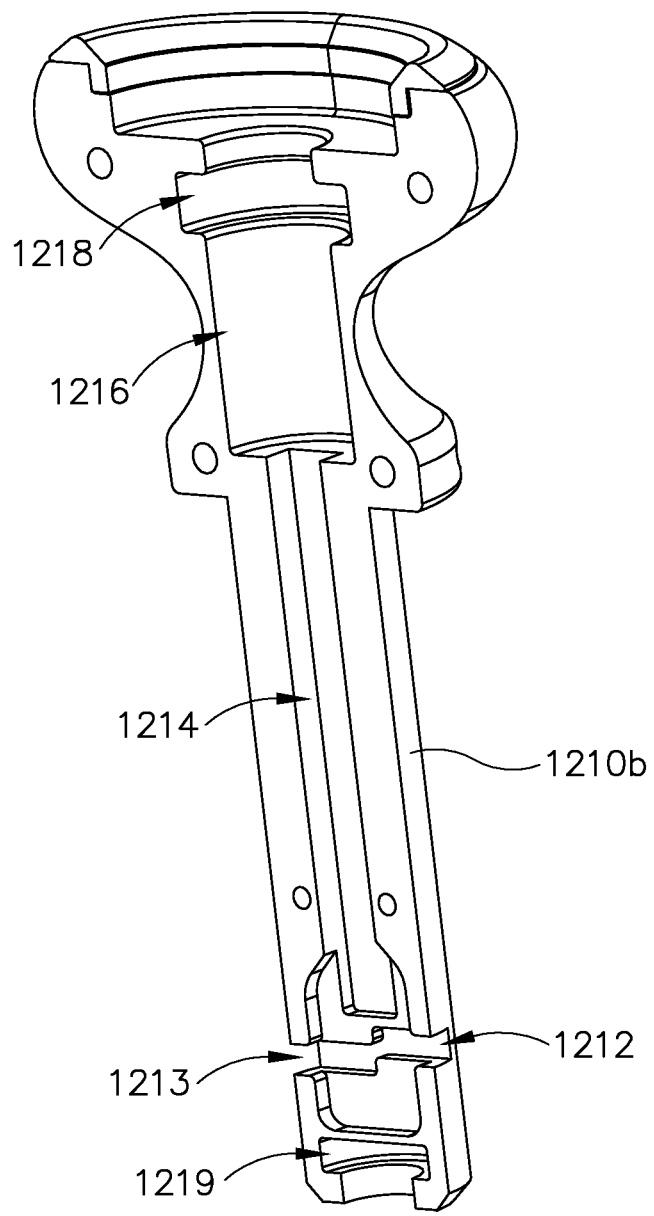
FIG. 35 depicts a perspective view of an actuator half of the plunger actuation assembly of FIG. 34.
Figure 36:
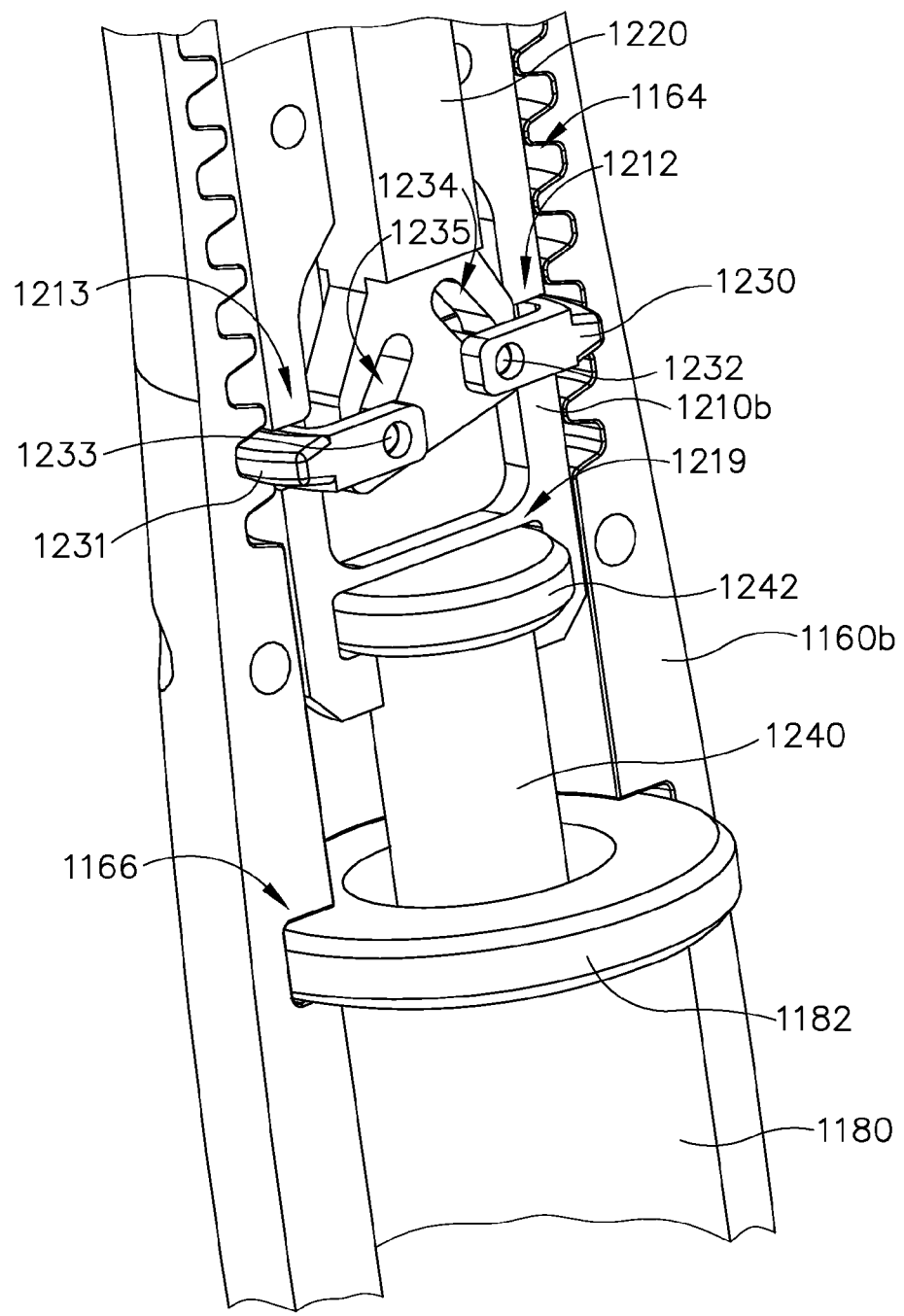
FIG. 36 depicts an enlarged perspective view of components of the plunger actuation assembly of FIG. 34 engaging the housing half of FIG. 33.

As shown in FIGS. 34-36, plunger actuation assembly (1200) of this example comprises a pair of rotary actuator halves (1210a, 1210b), a longitudinally translating rod (1220), a pair of retractable thread members (1230, 1231), and a plunger (1240). Rotary actuator halves (1210a, 1210b) cooperate to define a knob (1211) when halves (1210a, 1210b) are assembled together. Each half (1210a, 1210b) has a respective pair of thread channels (1212, 1213), a rod recess (1214), a spring recess (1216), and a rod flange recess (1218). When halves (1210a, 1210b) are assembled together, thread channels (1212, 1213) cooperate to enable thread members (1230, 1231) to selectively translate laterally relative to rod (1220) and thereby selectively protrude outwardly from the assembly of halves (1210a, 1210b) as will be described in greater detail below. In addition, rod recesses (1214) cooperate to slidingly receive rod (1220), enabling rod to translate longitudinally relative to assembled halves (1210a, 1210b). Spring recesses (1216) align with each other to capture the distal end of a spring (1222), which is configured to resiliently bias rod (1220) upwardly relative to assembled halves (1210a, 1210b). Rod flange recesses (1218) together encompass a flange (1224) of rod (1220) and thereby constrain longitudinal movement of rod (1220) relative to assembled halves (1210a, 1210b) while still permitting some degree of longitudinal movement of rod (1220) relative to assembled halves (1210a, 1210b). As will be described in greater detail below, such translation of rod (1220) selectively unlocks engagement between thread members (1230, 1231) and grooves (1164).

Each rotary actuator half (1210a, 1210b) also includes a plunger flange recess (1219). Plunger flange recesses (1219) cooperate to capture a proximal flange (1242) of plunger (1240). Plunger (1240) thus translates unitarily with assembled halves (1210a, 1210b) relative to housing (1160) and relative to syringe barrel (1180). A piston (1244) at the distal end of plunger (1240) is positioned within syringe barrel (1180). As also noted above, syringe barrel (1180) is secured by housing (1160). It should therefore be understood that plunger (1240) is configured to reciprocate within syringe barrel (1180) to selectively vary the volume of reservoir (1186) in syringe barrel (1180), to thereby draw fluid into or expel fluid from reservoir (1186), in response to longitudinal movement of plunger actuation assembly (1200) relative to housing (1160).

As noted above, translating rod (1220) of the present example comprises a spring (1222) and a flange (1224). Spring (1222) bears proximally against flange (1224). While spring (1222) of the present example comprises a coil spring, it should be understood that any other suitable type of resilient member may be used to resiliently bias rod (1220). Rod (1220) of the present example further includes a pushbutton (1226) and a pair of slots (1234, 1235) formed near the distal end of rod (1220). As best seen in FIG. 36, each slot (1234, 1235) is obliquely oriented relative to the longitudinal axis of rod (1220). In addition, slot (1234) is at a vertical position that is offset from the vertical position of slot (1235), such that slot (1235) is positioned distally in relation to slot (1234). Thread member (1230) is secured to a pin (1232), which is slidably disposed in slot (1234). Similarly, thread member (1231) is secured to a pin (1233), which is slidably disposed in slot (1235). Referring back to FIG. 35, thread member (1230) is configured to slidably fit in thread channel (1212), while thread member (1231) is configured to slidably fit in thread channel (1213). Thread channels (1212, 1213) prevent thread members (1230, 1231) from moving along the length of rotary actuator halves (1210a, 1210b); yet permit thread members (1230, 1231) to move laterally relative to rotary actuator halves (1210a, 1210b).

Figure 37A:
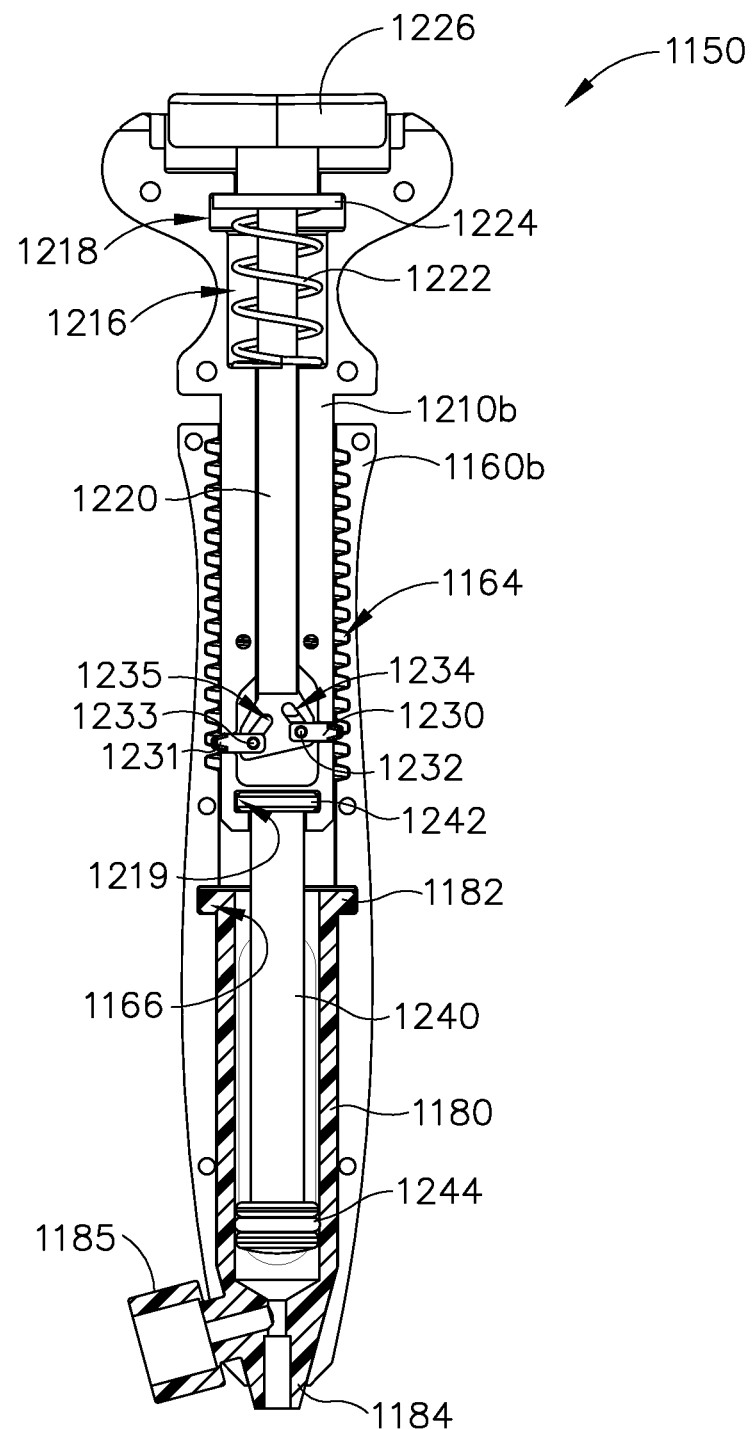
FIG. 37A depicts a cross-sectional side view of the inflator of FIG. 31, with the plunger actuation assembly in a distal and locked position.

Due to the configuration of thread channels (1212, 1213) and a camming action provided through cooperation between slots (1234, 1235) and pins (1232, 1233), thread members (1230, 1231) are configured to move between an inwardly retracted position (when rod (1220) is in a distal position relative to halves (1210a, 1210b)) and an outwardly extended position (when rod (1220) is in a proximal position relative to halves (1210a, 1210b)). In particular, FIG. 37A shows rod (1220) in a proximal position relative to halves (1210a, 1210b). As shown, thread members (1230, 1231) are in outwardly extended positions, such that the outer ends of thread members (1230, 1231) protrude outwardly from halves (1210a, 1210b) and engage grooves (1164) of housing (1160). When thread members (1230, 1231) are engaged with grooves (1164) of housing (1160) as shown in FIG. 37A, plunger actuation assembly (1200) will act like a lead screw such that rotation of knob (1211) relative to housing (1160) will advance or retract plunger actuation assembly (1200) relative to housing (1160), thereby advancing or retracting plunger (1240) relative to syringe barrel (1180), depending on the direction in which knob (1211) is rotated.

It should also be understood that the configuration of thread members (1230, 1231) and grooves (1164) may provide a self-locking functionality. In particular, the pressure of fluid within syringe barrel (1180) and/or the proximal bias provided by spring (1222) will not cause plunger actuation assembly (1200) to rotate and thereby "backdrive" plunger actuation assembly (1200) proximally while thread members (1230, 1231) are engaged with grooves (1164). When thread members (1230, 1231) are engaged with grooves (1164), plunger actuation assembly (1200) will only translate relative to housing (1160) when plunger actuation assembly (1200) is rotated relative to housing (1160) by an operator grasping knob (1211) and actively rotating knob (1211) relative to housing (1160).

Figure 37B:
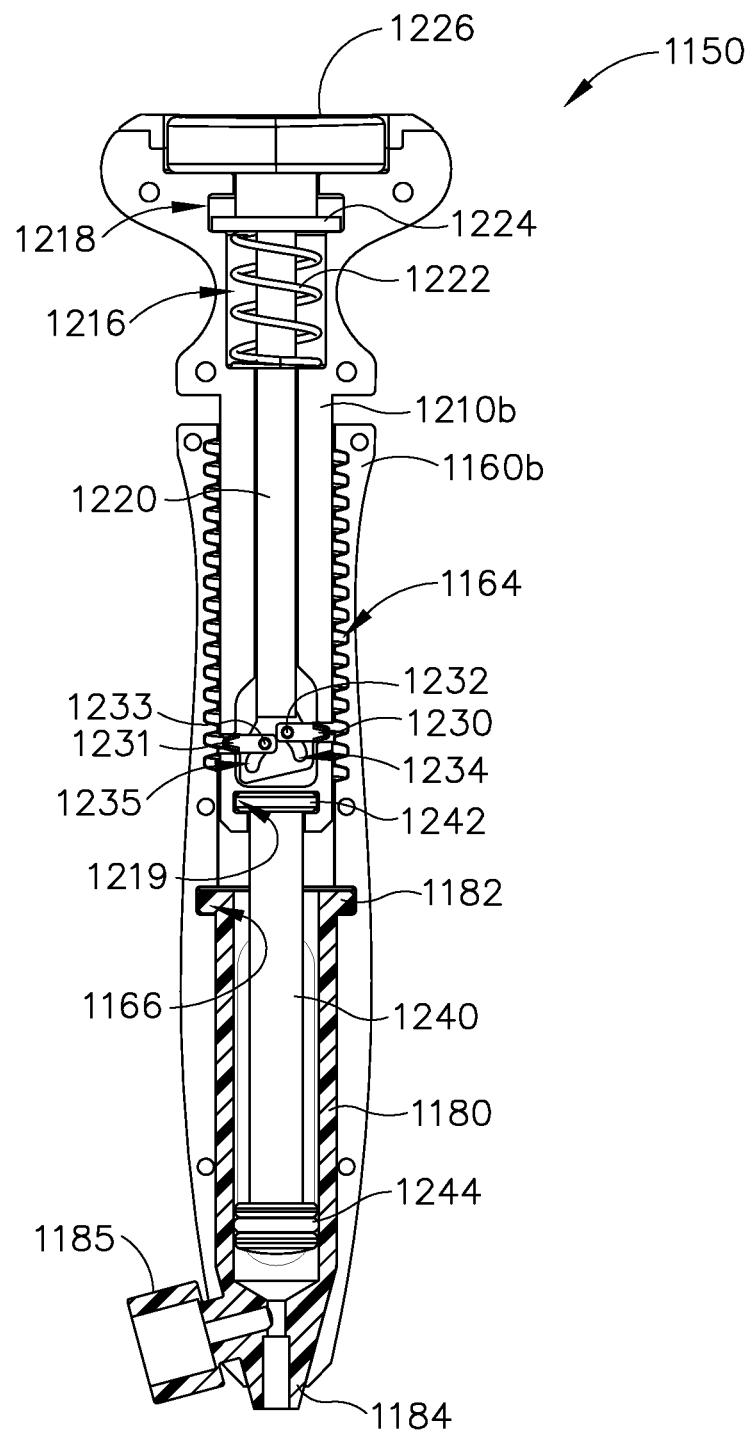
FIG. 37B depicts a cross-sectional side view of the inflator of FIG. 31, with the plunger actuation assembly in a distal and unlocked position.

When rod (1220) is translated to a distal position (e.g., by an operator pressing pushbutton (1226) while gripping housing (1160) and/or knob (1211)) as shown in FIG. 37B, the camming action between slots (1234, 1235) and pins (1232, 1233) simultaneously drives thread members (1230, 1231) inwardly, such that the outer ends of thread members (1230, 1231) disengage grooves (1164) of housing (1160) and retract within halves (1210a, 1210b). With thread members (1230, 1231) disengaged from grooves (1164), plunger actuation assembly (1200) may be freely advanced distally or retracted proximally relative to housing (1160). Due to the presence of spring (1222), the operator must hold pushbutton (1226) in a depressed position in order to keep thread members (1230, 1231) disengaged from grooves (1164). Once the operator releases pushbutton (1226), the resilient bias of spring (1222) will drive rod (1220) proximally relative to halves (1210a, 1210b). Due to the camming action between slots (1234, 1235) and pins (1232, 1233), the proximal movement of rod (1220) relative to halves (1210a, 1210b) will drive thread members (1230, 1231) simultaneously outwardly again and into engagement with grooves (1164).

Figure 37C:
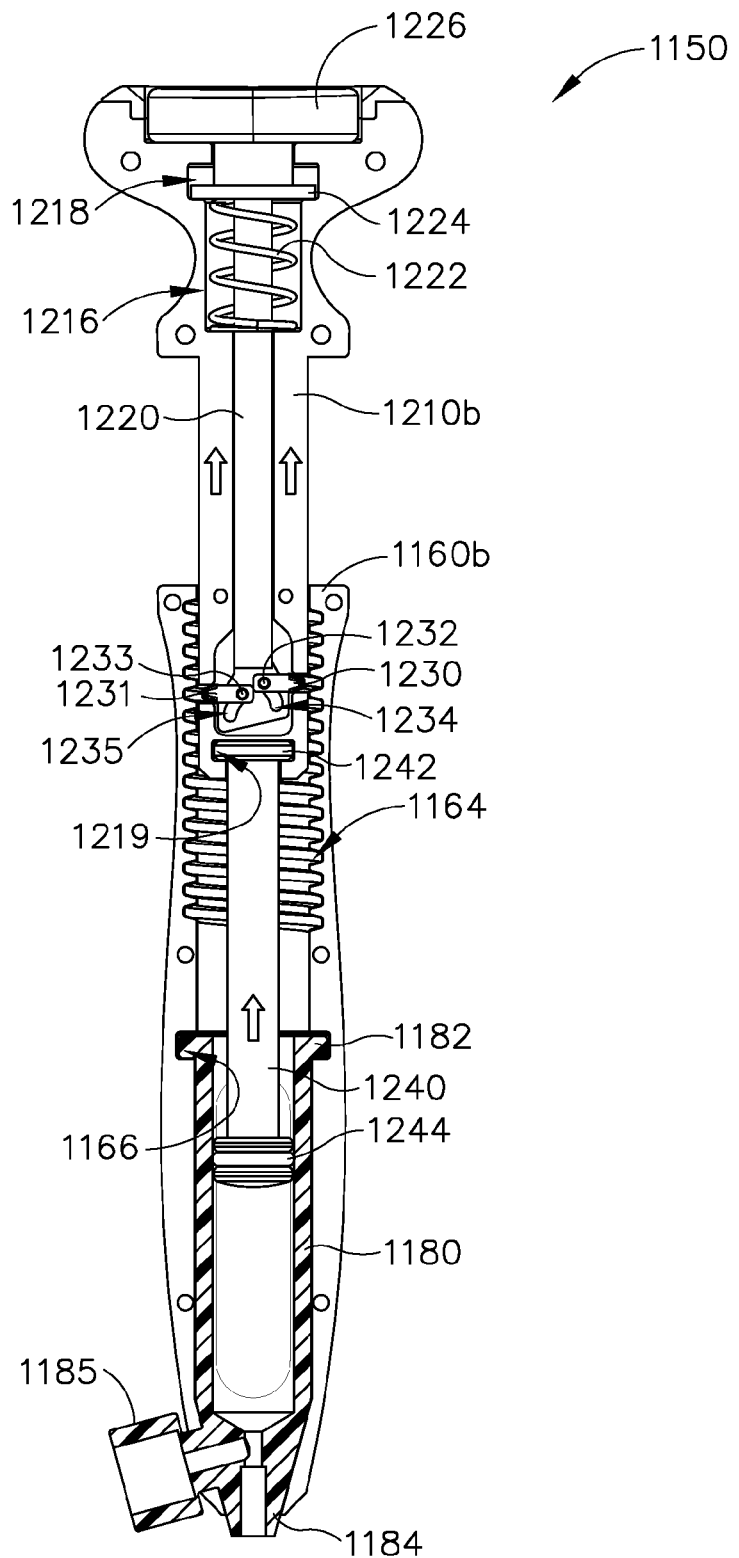
FIG. 37C depicts a cross-sectional side view of the inflator of FIG. 31, with the plunger actuation assembly in a proximal and unlocked position.

In an exemplary use of inflator (1150), a operator may start with plunger actuation assembly (1200) advanced to a distal position as shown in FIG. 37B. The operator may then position port (1184) in a bowl or other container of saline to draw fluid from. In instances where port (1184) is coupled with one end of flexible tube (46), the operator may position the other end of flexible tube (46) in the saline. In either case, the operator may then advance rod (1220) distally by pushing on pushbutton (1226), thereby disengaging thread members (1230, 1231) from grooves (1164) as shown in FIG. 37B. Next, the operator may pull plunger actuation assembly (1200) proximally relative to housing (1160) as shown in FIG. 37C, which will in turn retract plunger (1240) relative to syringe barrel (1180) to draw the saline (or other fluid) into reservoir (1186). The operator may then remove port (1184) or flexible tube (46) from the saline container and release pushbutton (1226). This will enable spring (1222) to drive rod (1220) proximally relative to halves (1210a, 1210b), which will result in rod (1220) driving thread members (1230, 1231) outwardly and back into engagement with grooves (1164).

At this stage, the operator may advance plunger (1240) distally in order to purge air from reservoir (1186). For instance, the operator may orient inflator (1150) such that port (1184) is positioned upwardly to gather air at the top of reservoir (1186) before advancing plunger (1240) distally in order to purge air from reservoir (1186). To purge air from reservoir (1186), the operator may depress pushbutton (1226) again to disengage thread members (1230, 1231) from grooves (1164), then push plunger actuation assembly (1200) distally relative to housing (1160) to advance plunger (1240) within syringe barrel (1180). Alternatively, the operator may refrain from depressing pushbutton (1226), and may instead rotate knob (1211) relative to housing (1160). Due to the engagement between thread members (1230, 1231) and grooves (1164) this rotation of knob (1211) relative to housing (1160) will drive plunger actuation assembly (1200)

distally relative to housing (1160), thereby advancing plunger (1240) within syringe barrel (1180).

Once reservoir (1186) has been sufficiently filled with fluid and air has been purged, the operator may couple inflator (1150) with dilation catheter (20), such as by coupling port (1184) with lateral port (26) via a flexible tube (46). With dilator (22) being suitably positioned within an anatomical passageway (e.g., an ostium (O), etc.), the operator may then advance plunger actuation assembly (1200) distally relative to housing (1160) to advance plunger (1240) within syringe barrel (1180), thereby transferring fluid from reservoir (1186) to dilator (22). The operator may observe the pressure reading at pressure gauge (1185) while advancing plunger actuation assembly (1200) distally in order to determine when the appropriate fluid pressure level has been reached.

In some instances, the advancement of plunger actuation assembly (1200) occurs in two stages. In the first stage, the operator may depress pushbutton (1226) again to disengage thread members (1230, 1231) from grooves (1164), then push plunger actuation assembly (1200) distally relative to housing (1160) to advance plunger (1240) within syringe barrel (1180) through a first range of motion that approaches but does not quite reach the desired fluid pressure. In the second stage, the operator may release pushbutton (1226) to re-engage thread members (1230, 1231) with grooves (1164), then rotate knob (1211) relative to housing (1160) to drive plunger actuation assembly (1200) distally relative to housing (1160), thereby advancing plunger (1240) within syringe barrel (1180) through a second range of motion in a more precisely controlled fashion until reaching the desired fluid pressure. When the operator stops rotating knob (1211) relative to housing (1160), the longitudinal position of plunger actuation assembly (1200) relative to housing (1160) will remain fixed (due to the self-locking nature of thread members (1230, 1231), etc.) until the operator either rotates knob (1211) again or depresses pushbutton (1226) to disengage thread members (1230, 1231) from grooves (1164).

Once the operator has attained the desired level of pressure in dilator (22) within the anatomical passageway to dilate the anatomical passageway, the operator may pause for an approximate, predetermined period of time (e.g., approximately three seconds, etc.). The operator may then depress pushbutton (1226) to once again disengage thread members (1230, 1231) from grooves (1164), then pull plunger actuation assembly (1200) proximally relative to housing (1160). This will retract plunger (1240) relative to syringe barrel (1180), thereby drawing fluid from dilator (22). With dilator (22) now deflated, the operator may re-inflate and deflate dilator (22) several times if desired in the same anatomical passageway, and dilator (22) may eventually be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (1186) may be used repeatedly to dilate a plurality of anatomical passageways, without having to withdraw dilator (22) from the patient, and without having to decouple inflator (1150) from the rest of dilator catheter system (10), until all of the desired dilations have been completed. Other suitable variations of inflator (1150) will be apparent to those of ordinary skill in the art in view of the teachings herein. Similarly, other suitable ways in which inflator (1150) may be used will be apparent to those of ordinary skill in the art in view of the teachings herein.

L. Exemplary Alternative Inflator with Lateral Recess and Tubing Grip

Figure 38:
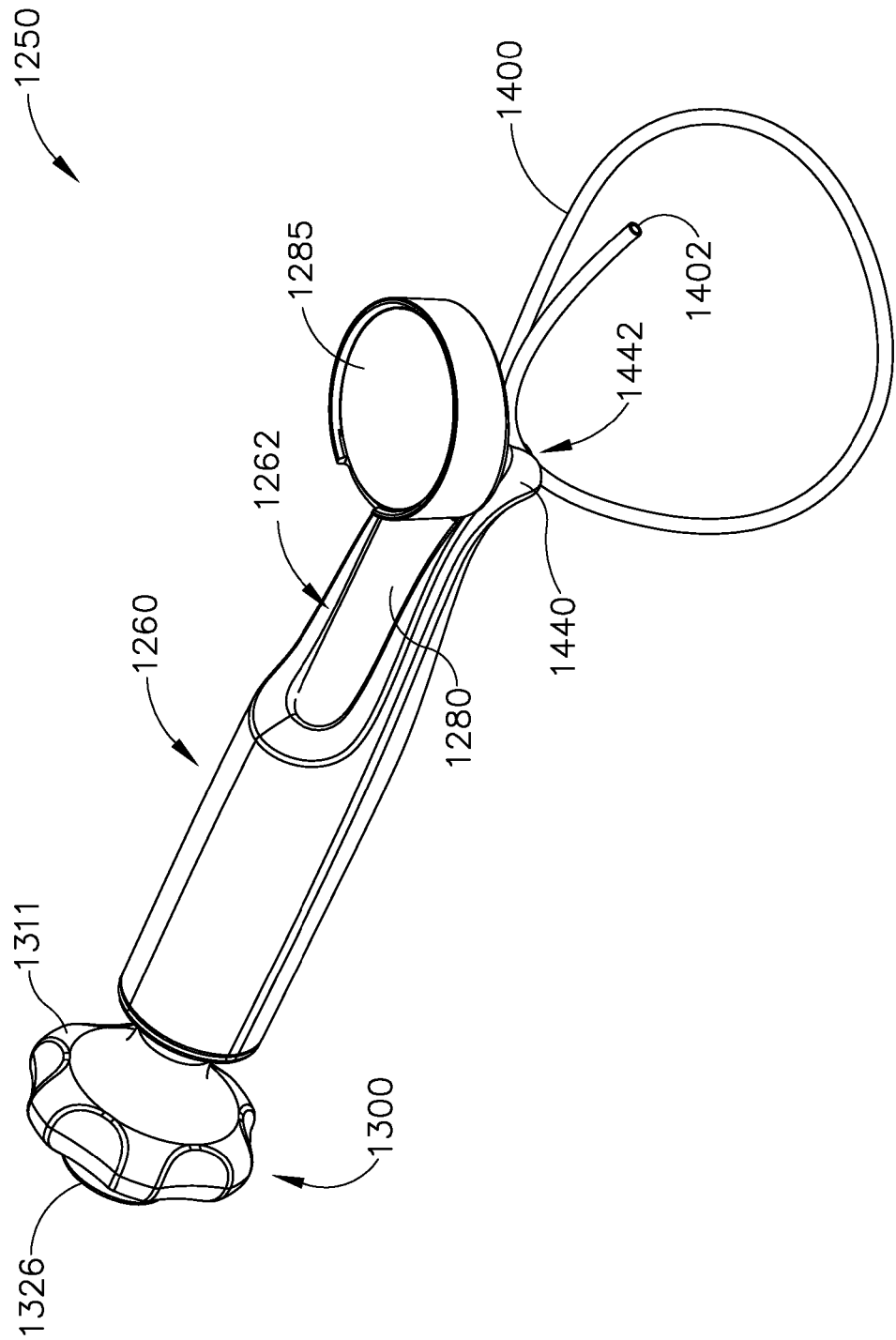
FIG. 38 depicts a perspective view of another exemplary inflator suited for use with the dilator catheter system of FIG. 1.
Figure 39:
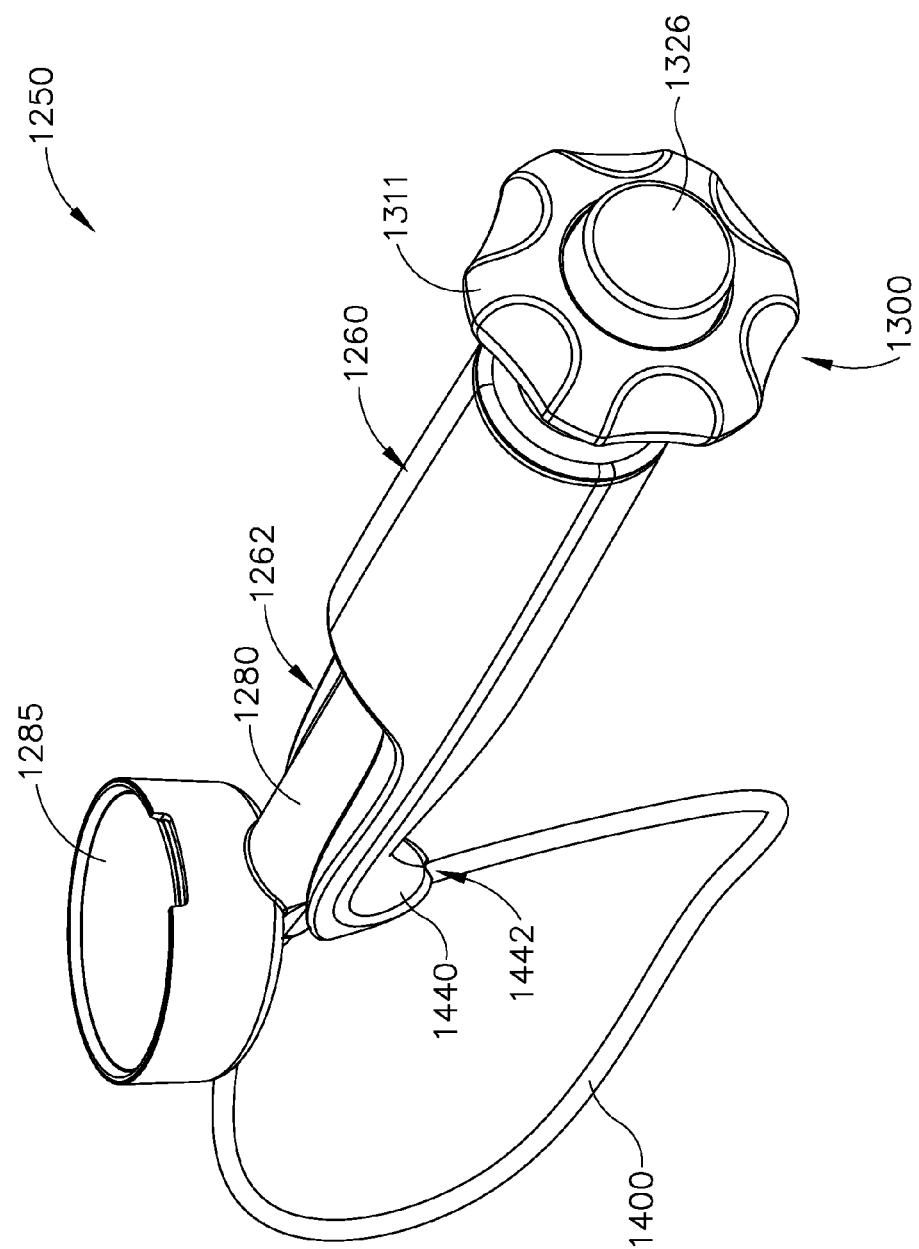
FIG. 39 depicts another perspective view of the inflator of FIG. 38.
Figure 40:
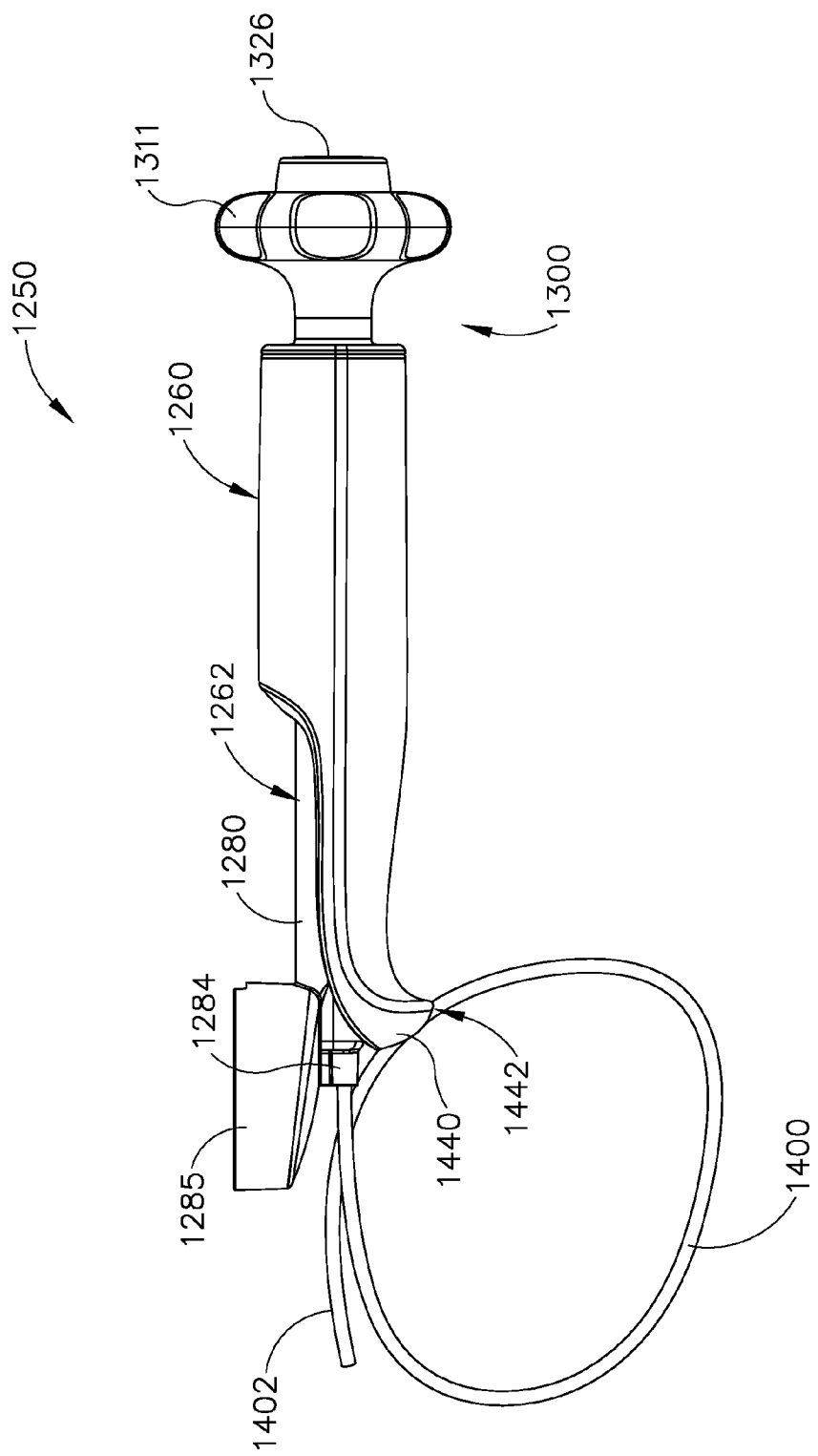
FIG. 40 depicts a side elevational view of the inflator of FIG. 38.
Figure 41:
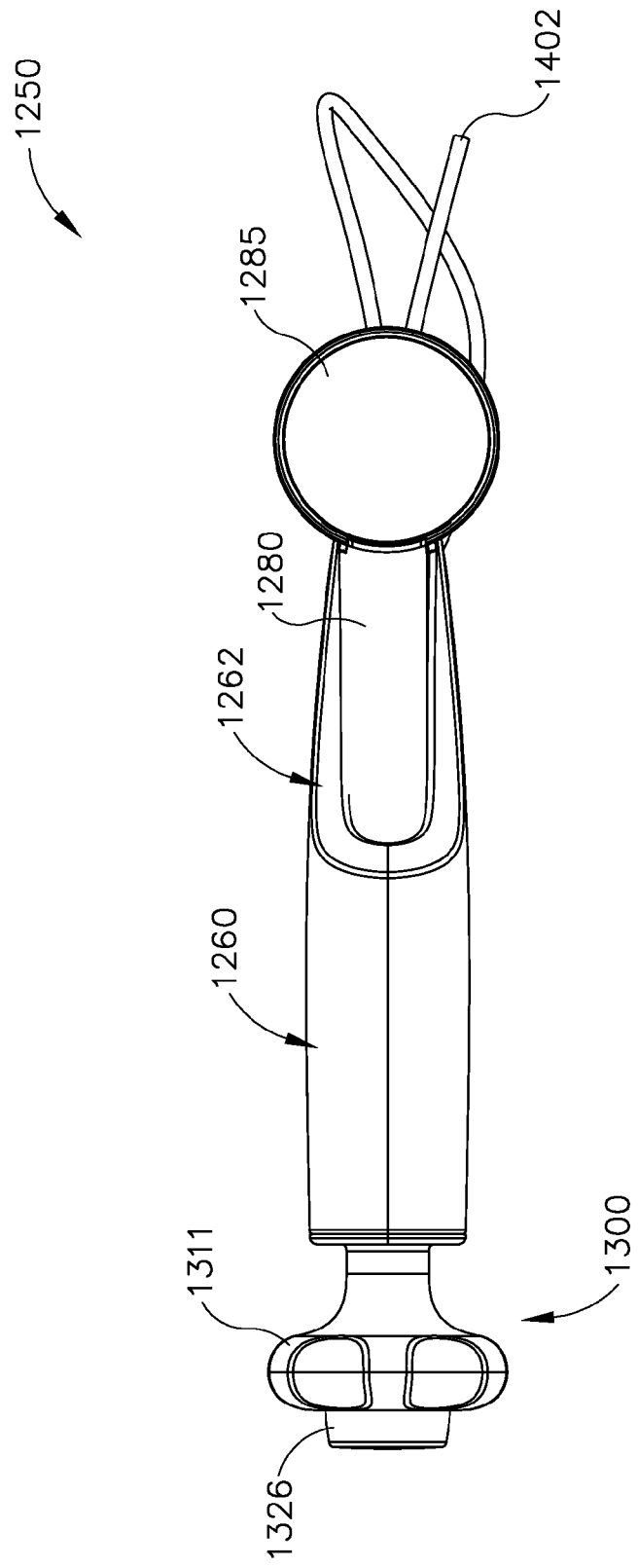
FIG. 41 depicts a top plan view of the inflator of FIG. 38.
Figure 42:
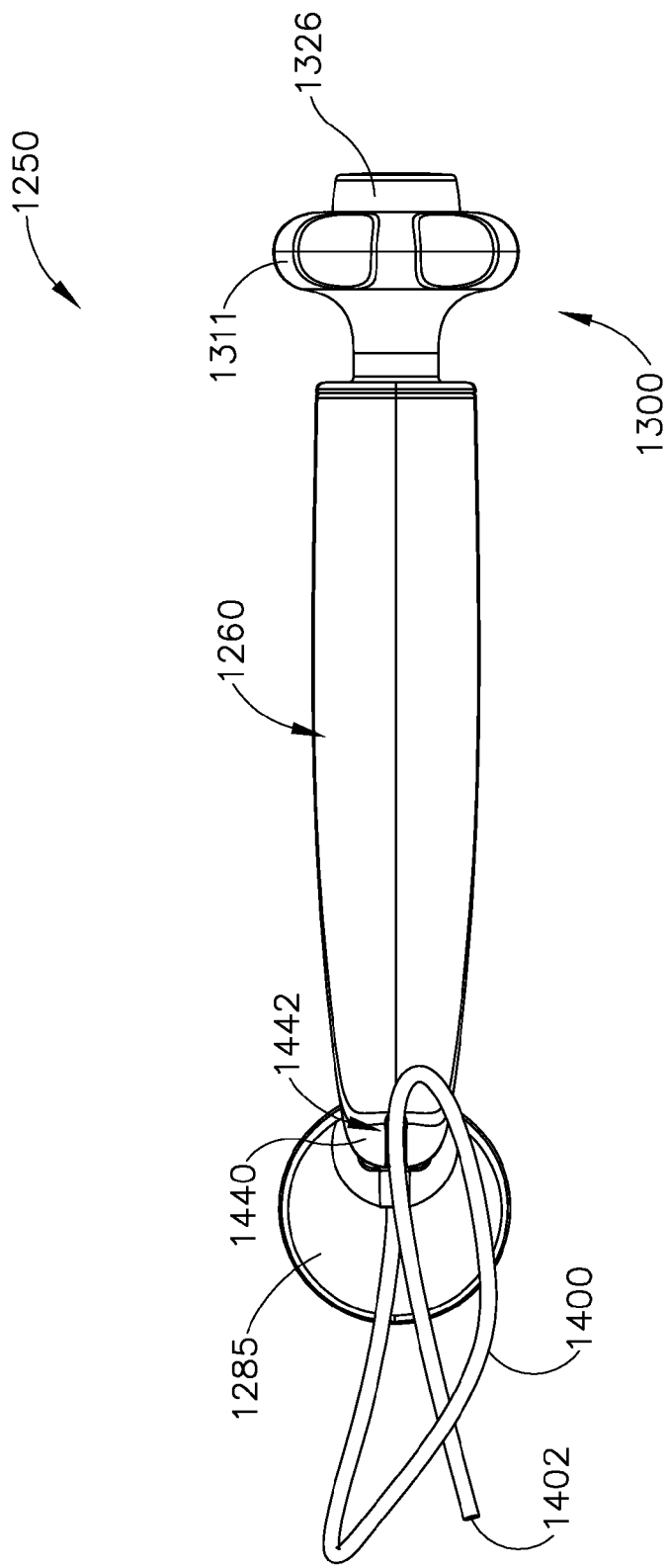
FIG. 42 depicts a bottom plan view of the inflator of FIG. 38.
Figure 43:
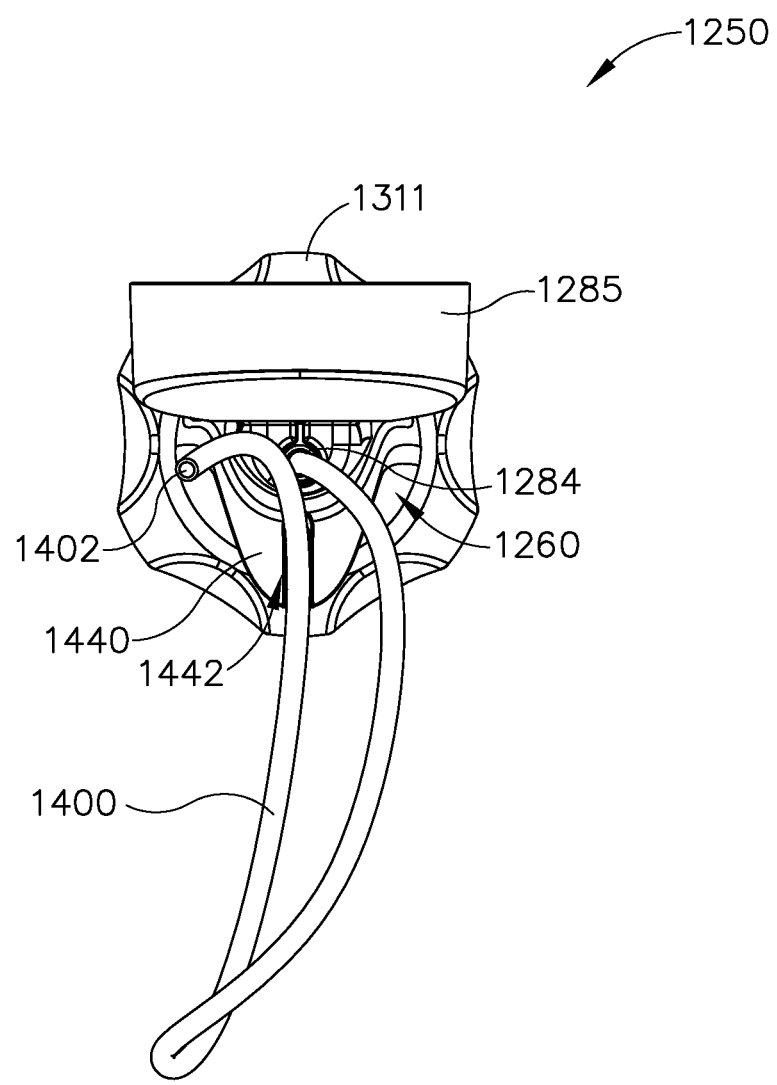
FIG. 43 depicts a front elevational view of the inflator of FIG. 38.
Figure 44:
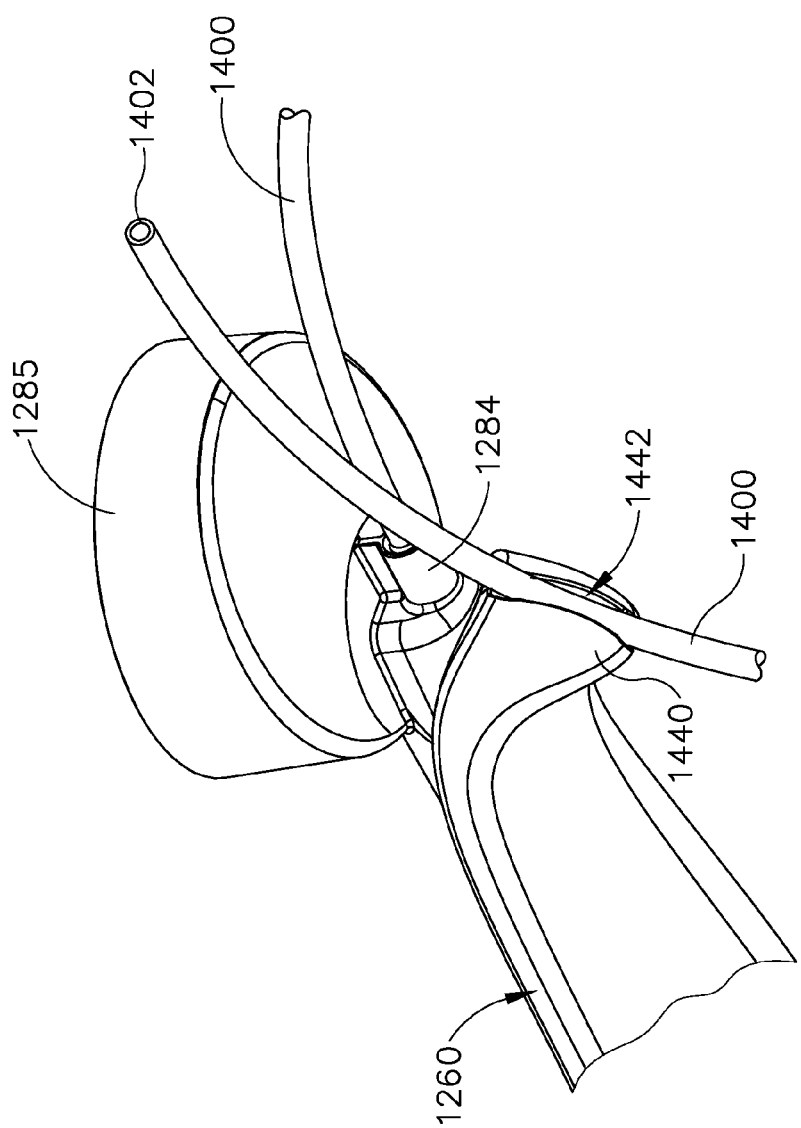
FIG. 44 depicts a partial perspective view of a distal portion of the inflator of FIG. 38.

FIGS. 38-44 depict another exemplary inflator (1250). Inflator (1250) of this example includes a housing (1260), a syringe barrel (1280), and a plunger actuation assembly (1300). Housing (1260) includes a window (1262) that permits viewing of syringe barrel (1280). As can be seen in FIGS. 38-40, window (1262) of this example is open along an angular extent of approximately 180°, though it should be understood that window (1262) may instead be open along any other suitable angular extent. In addition, as best seen in FIGS. 40 and 44, window (1262) extends to the distal end of housing (1260), wrapping under the distal port (1284) of syringe barrel (1280) in the present example. Housing (1260) of the present example further includes a tubing retention feature (1440) at the distal end of housing (1260). In particular, tubing retention feature (1440) defines a notch (1442) that is configured to receive and releasably retain tubing (1400) that is coupled with distal port (1284) of syringe barrel (1280). By way of example only, notch (1442) may define a gap width that is slightly less than the outer diameter of tubing (1400) such that tubing (1400) deforms to fit in notch (1442) with a slight interference to releasably retain tubing (1400) in notch (1442).

As shown, the configuration and positioning of notch (1442) enables tubing (1400) to form a loop, with the free end (1402) of tubing being located distal to inflator (1250). In some uses of inflator (1250), tubing (1400) is engaged with notch (1442) only before inflator (1250) is actually used. When actual use of inflator (1250) begins (e.g., filling syringe barrel (1280) with saline, actuating inflator (1250) to expand a dilator (22), etc.), tubing (1400) may be removed from notch (1442) to facilitate positioning of free end (1402) in relation to a saline source and/or in relation to a dilation catheter system (10), etc. Alternatively, tubing (1400) may remain disposed in notch (1442) when free end (1402) is positioned in a saline source to fill syringe barrel (1280). The operator may wish to selectively adjust the positioning of tubing (1400) in notch (1442) before inserting free end (1402) in the saline source, such as by sliding tubing (1400) within notch (1442) or removing tubing (1400) from notch (1442) then re-inserting tubing (1400) in notch, etc. Having tubing (1400) in notch (1442) while filling syringe barrel (1280) with saline may free up an operator's hand. In addition or in the alternative, the retention of tubing (1400) in notch (1442) may prevent tubing (1400) from undesirably flopping around or otherwise assuming an undesired orientation/configuration while syringe barrel (1280) is being filled. Other suitable ways in which notch (1442) may be used will be apparent to those of ordinary skill in the art in view of the teachings herein. It should also be understood that notch (1442) is merely optional.

Aside from the different configuration of window (1262) and the presence of tubing retention feature (1440), housing (1260) of the present example is substantially identical to housing (1160) described above. In particular, the interior of housing (1260) includes a groove similar to groove (1164); and a flange recess similar to flange recess (1166). Plunger actuation assembly (1300) of this example is substantially identical to plunger actuation assembly (1200) described above, and includes a knob (1311) and a pushbutton (1326). Unlike knob (1311) described above, knob (1311) of this example includes an angular array of curved recesses. Otherwise, plunger actuation assembly (1300) has all of the same features that plunger actuation assembly (1200) has, including selectively retractable thread members like thread members (1230, 1231), which selectively retract relative to housing (1260) when pushbutton (1326) is depressed. The operation of inflator (1250) is thus identical to the operation of inflator (1150) as described above. It should also be noted that syringe barrel (1280) includes an integral pressure gauge (1285) that is substantially identical to pressure gauge (1185) described above, though pressure gauge (1285) is of course merely optional. Other suitable features and operabilities that may be incorporated into inflator (1250) will be apparent to those of ordinary skill in the art in view of the teachings herein.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body, wherein the body includes a first locking feature;
   (b) a reservoir having a variable fluid capacity;
   (c) a plunger assembly, wherein the plunger assembly is movable relative to the body to selectively vary the fluid capacity of the reservoir, wherein the plunger assembly includes:
   (i) a housing member,
   (ii) a reciprocating member configured to translate relative to the housing member in response to manual actuation of the reciprocating member, and
   (iii) a second locking member configured to selectively engage the first locking feature in response to manual actuation of the reciprocating member to selectively maintain a location of the plunger assembly at a plurality of selected longitudinal positions in relation to the body, wherein the second locking member is configured to selectively disengage the first locking feature at the plurality of selected longitudinal positions in relation to the body in order to selectively allow linear translation of the plunger assembly relative to the body to selectively vary the fluid capacity of the reservoir,
   wherein the first locking feature and the second locking member are configured to selectively engage each other by one of the first locking feature or the second locking member moving linearly along a path that is transverse to a longitudinal axis defined by the plunger assembly, wherein the reciprocating member is resiliently biased to drive the second locking member into engagement with the first locking feature.

2. The apparatus of claim 1, wherein the body defines a handpiece.

3. The apparatus of claim 2, wherein the body further comprises a syringe body disposed within the handpiece, wherein the plunger assembly includes a piston slidably disposed in the syringe body, wherein the piston and the syringe body cooperate to define the reservoir.

4. The apparatus of claim 3, wherein the syringe body includes an integral pressure sensor.

5. The apparatus of claim 1, wherein the plunger assembly is rotatable relative to the body to selectively vary the fluid capacity.

6. The apparatus of claim 5, wherein the first locking feature and the second locking member are configured to provide translation of the plunger assembly relative to the body in response to rotation of the plunger assembly relative to the body.

7. The apparatus of claim 5, wherein the first locking feature comprises a helical groove defined by the body.

8. The apparatus of claim 7, wherein the second locking member comprises a first retractable thread member configured to selectively engage the helical groove, wherein the first retractable thread member is configured to travel linearly along a path that is transverse to a longitudinal axis defined by the plunger assembly to selectively engage the helical groove.

9. The apparatus of claim 1, wherein the second locking member further comprises a second retractable thread member configured to selectively engage the helical groove.

10. The apparatus of claim 9, wherein the reciprocating member is operable to simultaneously drive the first and second retractable thread members in opposite directions transverse to a longitudinal axis defined by the reciprocating member.

11. The apparatus of claim 9, wherein the first retractable thread member is located at a first longitudinal position along a length of the reciprocating member, wherein the second retractable thread member is located at a second longitudinal position along the length of the reciprocating member, wherein the first longitudinal position is proximal to the second longitudinal position.

12. The apparatus of claim 1, wherein the reciprocating member defines an oblique slot, wherein the second locking member is secured to a pin disposed in the oblique slot.

13. The apparatus of claim 1, wherein the housing member defines a channel and a longitudinal axis, wherein the channel is oriented transverse to the longitudinal axis, wherein the second locking member is slidably disposed in the channel.

14. The apparatus of claim 1, wherein the reservoir is contained within the body.

15. The apparatus of claim 14, wherein the body defines a window configured to enable viewing of at least a portion of the reservoir.

16. The apparatus of claim 1, wherein the plunger assembly is configured to translate freely relative to the body when the second locking member is disengaged from the first locking feature.

17. An apparatus, comprising:
(a) a handpiece, wherein the handpiece comprises:
   (i) a fluid reservoir, and
   (ii) a helical groove; and
(b) a plunger assembly slidable relative to the handpiece, wherein the plunger assembly is operable to define a variable capacity with the fluid reservoir, wherein the plunger assembly comprises:
   (i) a housing member defining a channel and a longitudinal axis, wherein the channel is oriented transverse to the longitudinal axis,
   (ii) a thread member configured to selectively engage the helical groove, wherein the thread member is slidably disposed in the channel,
   (iii) a rod slidable relative to the housing member, wherein the rod is operable to selectively engage and disengage the thread member with the helical groove, and
   (iv) an actuator configured to slide the rod relative to the housing member in order to selectively engage and disengage the thread member with the helical groove, wherein the actuator is configured to slide the rod relative to the housing member in response to manual actuation of the actuator;
wherein the plunger assembly is rotatable relative to the handpiece to vary the capacity defined by the plunger assembly and the fluid reservoir when the thread member is engaged with the helical groove,
wherein the plunger assembly is translatable relative to the handpiece to vary the capacity defined by the plunger assembly and the fluid reservoir when the thread member is disengaged from the helical groove.

18. An apparatus, comprising:
(a) a handpiece, wherein the handpiece comprises:
   (i) a fluid reservoir, and
   (ii) a helical groove;
(b) a plunger slidable relative to the handpiece, wherein the plunger is operable to define a variable capacity with the fluid reservoir;
(c) a pair of thread members configured to selectively engage the helical groove, wherein the pair of thread members are configured to actuate with the plunger relative to the handpiece; and
(d) a rod, wherein the rod is configured to actuate with the plunger relative to the handpiece, wherein the rod is slidable relative to the plunger in response to manual actuation of the rod, wherein the rod is operable to extend and retract the thread members in opposing transverse directions to thereby selectively engage and disengage the thread members with the helical groove in response to manual actuation of the rod, wherein the rod is resiliently biased to drive the pair of thread members into engagement with the helical groove.

\* \* \* \* \*